US012781278B2

(12) United States Patent
Astier et al.

(10) Patent No.: US 12,781,278 B2
(45) Date of Patent: Nov. 3, 2026

(54) METHODS OF SEQUENCING BY SYNTHESIS USING A CONSECUTIVE LABELING SCHEME

(71) Applicant: Roche Sequencing Solutions, Inc., Pleasanton, CA (US)

(72) Inventors: Yann Astier, Livermore, CA (US); Frank Bergmann, Iffeldorf (DE); Dieter Heindl, Munich (DE)

(73) Assignee: Roche Sequencing Solutions, Inc., Pleasanton, CA (US)

(*) Notice: Subject to any disclaimer, the term of this patent is extended or adjusted under 35 U.S.C. 154(b) by 1119 days.

(21) Appl. No.: 17/757,527

(22) PCT Filed: Dec. 17, 2020

(86) PCT No.: PCT/EP2020/086902
§ 371 (c)(1),
(2) Date: Jun. 16, 2022

(87) PCT Pub. No.: WO2021/123074
PCT Pub. Date: Jun. 24, 2021

(65) Prior Publication Data
US 2023/0061438 A1 Mar. 2, 2023

Related U.S. Application Data

(60) Provisional application No. 62/949,461, filed on Dec. 18, 2019.

(51) Int. Cl.
*C12Q 1/68* (2018.01)
*C07H 19/24* (2006.01)
*C12Q 1/6837* (2018.01)
*C12Q 1/6874* (2018.01)

(52) U.S. Cl.
CPC .......... *C12Q 1/6874* (2013.01); *C07H 19/24* (2013.01); *C12Q 1/6837* (2013.01)

(58) Field of Classification Search
CPC ..... C12Q 1/6874; C12Q 1/6837; C07H 19/24
See application file for complete search history.

(56) References Cited

U.S. PATENT DOCUMENTS

| | | | |
|---|---|---|---|
| 2003/0099950 | A1 | 5/2003 | Hanna |
| 2007/0166705 | A1 | 7/2007 | Milton et al. |

FOREIGN PATENT DOCUMENTS

| | | | | | |
|---|---|---|---|---|---|
| CN | 102180924 | A | 9/2011 | | |
| JP | 2002-360247 | A | 12/2002 | | |
| WO | 2002/029003 | A2 | 10/2001 | | |
| WO | 2003/048387 | A2 | 6/2003 | | |
| WO | 2003/066895 | A2 | 8/2003 | | |
| WO | 2007053719 | | 5/2007 | | |
| WO | 2015/148402 | A1 | 10/2015 | | |
| WO | 2018/129214 | A1 | 7/2018 | | |
| WO | 2019178393 | A1 | 9/2019 | | |
| WO | WO-2020257797 | A1 * | 12/2020 | ............. | C40B 50/06 |

OTHER PUBLICATIONS

Winkler, Johannes, Oligonucleotide conjugates for therapeutic applications, Therapeutic Delivery, vol. 4 , No. 7, pp. 791-809, 2013.
International Search Report for PCT/EP2020/086902, Filed Dec. 17, 2020, Issued Apr. 14, 2021.

* cited by examiner

*Primary Examiner* — Jezia Riley
(74) *Attorney, Agent, or Firm* — Matthew Flinders

(57) ABSTRACT

The present disclosure provides a method for sequencing target polynucleotide molecules. In some embodiments, the present disclosure provides a method of sequencing by synthesis where different subsets of nucleotide-conjugate complexes are sequentially formed and detected during each iterative extension of a plurality of nascent nucleic acid copy strands, where each nascent nucleic acid copy strand is complementary to one of a plurality of target polynucleotide molecules. In some embodiments, the plurality of target polynucleotide molecules are arrayed on a solid support.

10 Claims, 7 Drawing Sheets

Specification includes a Sequence Listing.

METHODS OF SEQUENCING BY SYNTHESIS USING A CONSECUTIVE LABELING SCHEME

CROSS-REFERENCE TO RELATED APPLICATIONS

The present patent application is a US National Stage Application filed under 35 U.S.C. § 371 of PCT/EP2020/086902, filed Dec. 17, 2020, which claims priority to U.S. Provisional Patent Application 62/949,461 filed Dec. 18, 2019. The entire contents of each of these applications are incorporated herein by reference for all purposes.

BACKGROUND OF THE DISCLOSURE

The importance of DNA sequencing has increased dramatically from its inception four decades ago. It is recognized as a crucial technology for most areas of biology and medicine and as the underpinning for the new paradigm of personalized and precision medicine. Information on individuals' genomes and epigenomes can help reveal their propensity for disease, clinical prognosis, and response to therapeutics; but the routine application of genome sequencing in medicine requires comprehensive data delivered in a timely and cost-effective manner.

A well-known sequencing method is the Sequencing-by-Synthesis (SBS) method first described by R. Tsien (WO 91/06678). This method utilizes reversible terminator nucleotides which are protected at their 3'-OH groups. Current sequencing systems utilize reversible terminator nucleotides including a fluorescent label. On addition of a mixture of different reversible terminator nucleotides to a flow cell, a DNA polymerase incorporates the modified nucleotides into the DNA strand being synthesized, the strands are imaged, and then the incorporated nucleotides are de-protected at their 3'-OH group, allowing another cycle of nucleotide incorporation.

More specifically, each cycle in sequencing by reversible termination consists of three steps: (i) incorporation of the complementary reversible terminator nucleotide by a mutant DNA polymerase into the DNA strand attached to the flow cell, (ii) detection of the different fluorescence signal for the four bases of the different reversible terminator nucleotides, and (iii) restoration of the free 3'-OH group by cleaving the terminating moiety and fluorescent label. In some embodiments, the fluorescent dye is identified through laser excitation and imaging. Repetition of this cycle leads to sequencing of the DNA template.

BRIEF SUMMARY OF THE DISCLOSURE

Applicant has developed an improved method of Sequencing-by-Synthesis utilizing magnetic sensor arrays and reagents incorporating detectable magnetic labels. Applicant has discovered that performing Sequencing-by-Synthesis using such magnetic sensor arrays and reagents including detectable magnetic labels dramatically increases sequencing throughput and reduces the cost of sequencing, while eliminating the need for high-power lasers and high-resolution optics in sequencing systems.

In one aspect of the present disclosure is a method of sequencing a plurality of target polynucleotides arrayed on a solid support including: (a) incorporating one of four different nucleotides into nascent nucleic acid copy strands complementary to each of the plurality of target polynucleotides, wherein each of the four different nucleotides comprise (i) a 3'-hydroxyl protecting group, and (ii) a first reactive group coupled to a nucleobase through a cleavable linker, and where each different nucleotide of the four different nucleotides includes a different nucleobase and a different first reactive group; (b) sequentially forming different subsets of nucleotide-conjugate complexes, where each nucleotide-conjugate complex within each different subset of formed nucleotide-conjugate complexes is derived from only one of the different nucleotides incorporated into the nascent nucleic acid copy strands, wherein the sequential formation of each different subset of nucleotide-conjugate complexes includes: (i) introducing a conjugate including a detectable label and which is orthogonally reactive with only one of the four different nucleotides incorporated into the nascent nucleic acid copy strands; (ii) detecting the formation of each nucleotide-conjugate complex within the subset by detecting the label of each introduced conjugate; (iii) determining a position within the solid support of each detected nucleotide-conjugate complex within the subset; and (iv) optionally cleaving at least the detectable label from each of the formed detectable nucleotide-conjugate complexes within the subset.

In some embodiments, the different first reactive groups of each of the four different nucleotides are independently selected from a first member of a pair of reactive functional groups capable of participating in a "click chemistry" reaction, a first member of a pair of specifying binding entities, a first oligonucleotide, and a first member of a pair of host/guest molecules. In some embodiments, the introduced conjugate includes a second reactive group selected from a second member of the pair of reactive functional groups capable of participating in a "click chemistry" reaction, a second member of the pair of specifying binding entities, a second oligonucleotide capable of hybridizing with the first oligonucleotide, and a second member of the pair of host/guest molecules. In some embodiments, the first and second reactive groups include first and second oligonucleotides capable of hybridizing with one another.

In some embodiments, the different first reactive groups of each of the four different nucleotides comprise a different first oligonucleotide. In some embodiments, the different first oligonucleotides may be selected from any one of SEQ ID NOS: 1-58. In some embodiments, each different first oligonucleotide includes a first LNA-modified oligonucleotide. In some embodiments, a first LNA-modified oligonucleotide includes a sequence selected from any one of SEQ ID NOS: 1-22 and 29-50.

In some embodiments, the second reactive group of the introduced conjugate includes a second oligonucleotide capable of hybridizing with the first oligonucleotide. In some embodiments, the second oligonucleotide capable of hybridizing with the first oligonucleotide is selected from any one of SEQ ID NOS: 1-58. In some embodiments, the second oligonucleotide capable of hybridizing with the first oligonucleotide includes a second LNA-modified oligonucleotide. In some embodiments, the second LNA-modified oligonucleotide includes between 3 and 12 mer. In some embodiments, the second LNA-modified oligonucleotide includes between 5 and 10 mer. In some embodiments, the second LNA-modified oligonucleotide includes a sequence selected any one of SEQ ID NOS: 1-22 and 29-50. In some embodiments, the second oligonucleotide capable of hybridizing with the first oligonucleotide includes an L-configured oligonucleotide. In some embodiments, the second oligonucleotide capable of hybridizing with the first oligonucleotide includes a beta-L-LNA oligonucleotide.

In some embodiments, the cleavable linker includes at least one cleavable group selected from the group consisting of a disulfide group, an alpha-azidoether, a nitrobenzyl-based group, and a phenacyl group. In some embodiments, the incorporation of the different nucleotides into the nascent nucleic acid copy strands complementary to each of the plurality of target polynucleotides present on the solid support includes introducing a mixture of the four different nucleotides to the solid support. In some embodiments, the sequential formation of the different subsets of nucleotide-conjugate complexes is performed three times such that three different subsets of detectable nucleotide-conjugate complexes are formed and detected.

In some embodiments, the method further includes removing each of the 3-hydroxyl protecting groups from the different nucleotides incorporated into the nascent nucleic acid copy strands complementary to each of the plurality of target polynucleotides. In some embodiments, the 3-hydroxyl protecting groups comprise azidomethyl groups. In some embodiments, the method further includes introducing a mixture of the four different nucleotides to the solid support to extend each of the nascent nucleic acid strands complementary to each of the plurality of target polynucleotides on the solid support.

In some embodiments, the four different nucleotides have the structures of any one of Formulas (IC), (ID), (IE), and (IF):

(IC)

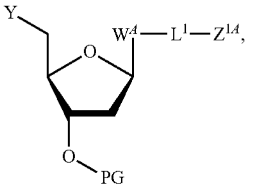

(ID)

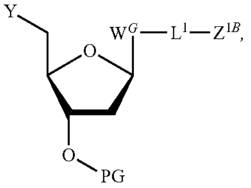

(IE)

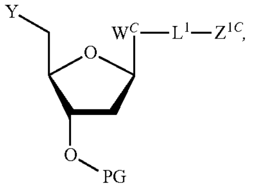

and (IF)

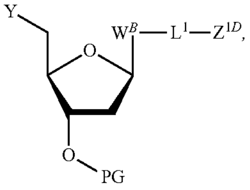

wherein $W^A$ is an adenine nucleobase, $W^G$ is a guanine nucleobase; $W^C$ is a cytosine nucleobase; $W^R$ is one of a thymine nucleobase or an uracil nucleobase;

$Z^{1A}$, $Z^{1B}$, $Z^{1C}$, and $Z^{1D}$ are each different first reactive groups;

Y is —O—P(O)(OH)[—O—P(O)(OH)]$_z$—OH, wherein z ranges from 2 to about 5;

PG is a protecting group; and each $L^1$ is independently a straight chain or branched, substituted or unsubstituted, saturated or unsaturated, aliphatic or aromatic moiety having between 1 and about 60 carbon atoms and optionally substituted with one or more heteroatoms, provided that $L^1$ includes one or more cleavable groups.

In some embodiments, z is 2.

In some embodiments, the detectable label of each introduced conjugate includes a magnetic nanoparticle. In some embodiments, the magnetic nanoparticle includes a material selected from the group consisting of FeO, $Fe_3O_4$, FePt, FePd, and CoPt. In some embodiments, the magnetic nanoparticles are detected using a magnetic sensor array.

In some embodiments, the introduced conjugate has the structure of any one of Formulas (IIA) and (IIB):

$$D—L^2—Z^2, \quad \text{(IIA)}$$

$$D—[L^2—Z^2]_p, \quad \text{(IIB)}$$

wherein

D is a detectable label or a conjugate including a detectable label;

$L^2$ is a straight chain or branched, substituted or unsubstituted, saturated or unsaturated, aliphatic or aromatic moiety having between 1 and about 60 carbon atoms and optionally including one or more heteroatoms;

$Z^2$ is a second reactive group; and p ranges from 2 to about 1000.

In some embodiments, $L^2$ includes a cleavable group. In some embodiments, $L^2$ includes a moiety derived from biotin.

In some embodiments, the method further includes removing non-incorporated nucleotides prior to the sequential formation of the different subsets of nucleotide-conjugate complexes.

In another aspect of the present disclosure is a method of determining a sequence of a plurality of target polynucleotides arrayed on a solid support including: (a) incorporating one of four different nucleotides into nascent nucleic acid strands complementary to each of the plurality of target polynucleotides, wherein each of the four different nucleotides includes a first reactive group coupled to a nucleobase through a cleavable linker and a 3-hydroxyl protecting group, and where each different nucleotide of the four different nucleotides includes a different nucleobase and a different first reactive group; (b) sequentially labeling each one of the four different nucleotides incorporated into the nascent nucleic acid strands, wherein the sequential labeling includes: (i) introducing a conjugate including a detectable label and which is orthogonally reactive with only one of the four different nucleotides incorporated into the nascent nucleic acid strands to provide one or more labeled nucleotides; (ii) detecting the label of the one or more labeled nucleotides; (iii) based on the detected labels, identifying a position within the solid support of the one or more labeled nucleotides; and (iv) optionally cleaving at least a detectable label from the one or more labeled nucleotides incorporated into the nascent nucleic acid strands.

In some embodiments, the different first reactive groups of each of the four different nucleotides are independently selected from the group consisting of a first member of a pair of reactive functional groups capable of participating in a "click chemistry" reaction, a first member of a pair of specifying binding entities, a first oligonucleotide, and a first member of a pair of host/guest molecules. In some embodiments, the different first reactive groups of each of the four different nucleotides comprise a different first oligonucleotide. In some embodiments, each of the introduced conjugates comprise a second oligonucleotide complementary to one of the first oligonucleotides. In some embodiments, the second oligonucleotide complementary to one of the first oligonucleotides includes an L-configured oligonucleotide. In some embodiments, the second oligonucleotide complementary to one of the first oligonucleotides includes a beta-L-LNA oligonucleotide. In some embodiments, the second oligonucleotide complementary to one of the first oligonucleotides includes one or more LNA monomers. In some embodiments, the second oligonucleotide has a sequence selected from the group consisting of any one of SEQ ID NOS: 1-22 and 29-50. In some embodiments, the second oligonucleotide complementary to one of the first oligonucleotides includes one or more PNA monomers.

In some embodiments, the cleavable linker includes at least one cleavable group selected from the group consisting of a disulfide group, an alpha-azidoether, a nitrobenzyl-based group, and a phenacyl group. In some embodiments, the incorporation of the different nucleotides into the nascent nucleic acid strands complementary to each of the plurality of target polynucleotides present on the solid support includes introducing a mixture of the four different nucleotides to the solid support.

In some embodiments, the sequential labeling is performed three times. In some embodiments, the sequential labeling is performed four times. In some embodiments, the method further includes removing each of the 3-hydroxyl protecting groups from the different nucleotides incorporated into the nascent nucleic acid strands complementary to each of the plurality of target polynucleotides. In some embodiments, the 3-hydroxyl protecting groups comprise azidomethyl groups.

In some embodiments, the method further includes introducing a mixture of the four different nucleotides to the solid support to extend each of the nascent nucleic acid strands complementary to each of the plurality of target polynucleotides on the solid support. In some embodiments, the method further includes removing non-incorporated nucleotides prior to the sequential formation of the different subsets of nucleotide-conjugate complexes. In some embodiments, the method further includes removing any unreacted conjugates between each sequential labeling.

In another aspect of the present disclosure is a compound or a salt thereof having a structure defined by Formula (IA):

(IA)

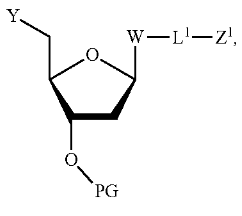

wherein

Y is —O—P(O)(OH)[—O—P(O)(OH)]$_z$—OH or —O—P(O)(OH)-oligonucleotide; where z ranges from between 2 to about 5;

PG is a protecting group;

W is a nucleobase;

$L^1$ is a straight chain or branched, substituted or unsubstituted, saturated or unsaturated, aliphatic or aromatic moiety having between 1 and about 60 carbon atoms and optionally including one or more heteroatoms, provided that $L^1$ includes one or more cleavable groups; and $Z^1$ is an oligonucleotide.

In some embodiments, z is 2.

In some embodiments, $Z^1$ includes an LNA-modified oligonucleotide. In some embodiments, $Z^1$ includes a PNA-modified oligonucleotide. In some embodiments, $Z^1$ includes L-configured monomers, e.g. at least one L-configured monomer. In some embodiments, the L-configured monomers are L-configured LNA monomers. In some embodiments, the L-configured LNA monomers are beta-L-LNA monomers. In some embodiments, the oligonucleotide includes between 4 and 12 mer. In some embodiments, the oligonucleotide includes between 5 and 10 mer. In some embodiments, the oligonucleotide includes a sequence selected from any one of SEQ ID NOS: 1-22 or 29-50. In some embodiments, the at least one cleavable group is selected from the group consisting of a chemically cleavable group, an enzymatically cleavable group, and a photocleavable group.

In another aspect of the present disclosure is a nucleotide including (i) a 3-hydroxyl protecting group, and (ii) a reactive group coupled to a nucleobase through a cleavable linker, wherein the reactive group includes an LNA-modified oligonucleotide or a beta-L-LNA modified oligonucleotide. In some embodiments, the LNA-modified oligonucleotide or the beta-L-LNA modified oligonucleotide includes a sequence having any of SEQ ID NOS: 1-22 or 29-50.

In another aspect of the present disclosure is a kit including one nucleotide of Formula (IC), one nucleotide of Formula (ID), one nucleotide of Formula (IE), and one nucleotide of Formula (IF):

(IC)

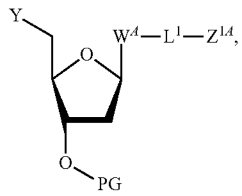

(ID)

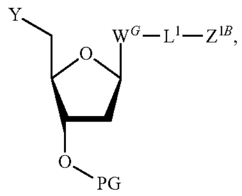

(IE)

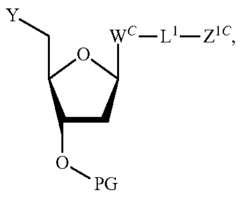

and

-continued (IF)

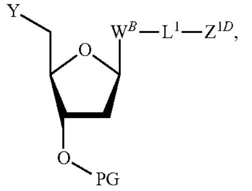

wherein

Y is —O—P(O)(OH)[—O—P(O)(OH)]$_z$—OH, where z is na integer ranging from 2 to about 5;

PG is a protecting group;

$W^A$ is an adenine nucleobase;

$W^G$ is a guanine nucleobase;

$W^C$ is a cytosine nucleobase;

$W^R$ is one of a thymine nucleobase or an uracil nucleobase;

$L^1$ is a straight chain or branched, substituted or unsubstituted, saturated or unsaturated, aliphatic or aromatic moiety having between 1 and about 60 carbon atoms and optionally including one or more heteroatoms, provided that $L^1$ includes one or more cleavable groups; and $Z^{1A}$, $Z^{1B}$, $Z^{1C}$, and $Z^{1D}$ each comprise a different first reactive group.

In some embodiments, z is 2.

In some embodiments, the $Z^{1A}$, $Z^{1B}$, $Z^{1C}$, and $Z^{1D}$ first reactive groups are independently selected from the group consisting of a first member of a pair of reactive functional groups capable of participating in a "click chemistry" reaction, a first member of a pair of specifying binding entities, a first oligonucleotide, and a first member of a pair of host/guest molecules. In some embodiments, the $Z^{1A}$, $Z^{1B}$, $Z^{1C}$, and $Z^{1D}$ first reactive groups each comprise a different first oligonucleotide. In some embodiments, the $Z^{1A}$, $Z^{1B}$, $Z^{1C}$, and $Z^{1D}$ first reactive groups each comprise a different LNA-modified first oligonucleotide. In some embodiments, the $Z^{1A}$, $Z^{1B}$, $Z^{1C}$, and $Z^{1D}$ first reactive groups each comprise a different beta-L-LNA-modified first oligonucleotide.

In some embodiments, the kit further includes at least three different conjugates, where each of the at least three different conjugates includes a different second reactive group which reacts orthogonally with one of $Z^{1A}$, $Z^{1B}$, $Z^{1C}$, and $Z^{1D}$. In some embodiments, each different second reactive group reacts orthogonally with one of the $Z^{1A}$, $Z^{1B}$, $Z^{1C}$, and $Z^{1D}$ first reactive groups. In some embodiments, each different second reactive group includes a different second oligonucleotide. In some embodiments, each different second oligonucleotide includes at least one LNA monomer. In some embodiments, each different second oligonucleotide includes at least one beta-L-LNA monomer.

In another aspect of the present disclosure is a nucleotide-conjugate complex, wherein the nucleotide-conjugate complex is produced by a process including: reacting (i) a nucleotide having the structure of Formula (IA):

(IA)

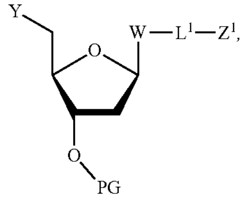

wherein

Y is —O—P(O)(OH)-oligonucleotide;

PG is a protecting group;

W is a nucleobase;

$L^1$ is a straight chain or branched, substituted or unsubstituted, saturated or unsaturated, aliphatic or aromatic moiety having between 1 and about 60 carbon atoms and optionally substituted with one or more heteroatoms, provided that $L^1$ includes one or more cleavable groups; and $Z^1$ is a first reactive group;

with (ii) a conjugate having the structure of any one of Formulas (IIA) or (IIB):

$$D—L^2—Z^2, \quad \text{(IIA)}$$

$$D—[L^2—Z^2]_p, \quad \text{(IIB)}$$

wherein

D is a detectable label or a conjugate including a detectable label;

$L^2$ is a straight chain or branched, substituted or unsubstituted, saturated or unsaturated, aliphatic or aromatic moiety having between 1 and about 60 carbon atoms and optionally including one or more heteroatoms;

$Z^2$ is a second reactive group which is orthogonally reactive with the first reactive group $Z^1$; and p is an integer ranging from 2 to about 1000.

In some embodiments, $L^2$ includes biotin or a moiety derived from biotin.

In some embodiments, the conjugate has the structure of Formula (IIA). In some embodiments, the conjugate has the structure of Formula (IIB), and where p ranges from 2 to about 100.

In some embodiments, the first reactive group includes a first member of a pair of reactive functional groups capable of participating in a "click chemistry" reaction. In some embodiments, the first reactive group includes a first member of a pair of specific binding entities. In some embodiments, the first member of the pair of specific binding entities is a hapten. In some embodiments, the first reactive group includes a first member of a pair of host/guest molecules. In some embodiments, the first reactive group includes a first oligonucleotide. In some embodiments, the first oligonucleotide is an LNA-modified first oligonucleotide. In some embodiments, the LNA-modified first oligonucleotide includes at least one L-configured LNA monomer. In some embodiments, the LNA-modified first oligonucleotide includes a sequence having any one of SEQ ID NOS: 1-22 or 29-50.

In some embodiments, the second reactive group includes a second oligonucleotide which is complementary to the first oligonucleotide. In some embodiments, the second oligonucleotide is an LNA-modified second oligonucleotide or a beta-L-LNA-modified second oligonucleotide. In some embodiments, the LNA-modified second oligonucleotide includes a sequence having any one of SEQ ID NOS: 1-22 or 29-50.

In some embodiments, the detectable label includes a fluorescent molecule. In some embodiments, the detectable label includes a magnetic nanoparticle. In some embodiments, the magnetic nanoparticle includes a ferromagnetic material. In some embodiments, the magnetic nanoparticle includes a material selected from the group consisting of FeO, $Fe_3O_4$, FePt, FePd, and CoPt.

In another aspect of the present disclosure is a solid support including a plurality of nascent nucleic acid copy strands indirectly coupled thereto, wherein the plurality of nascent nucleic acid copy strands each include an incorporated nucleotide having Formula (IA):

(IA)

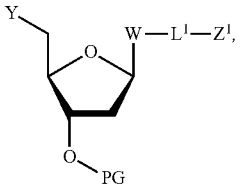

wherein

Y is —O—P(O)(OH)—O-oligonucleotide, where

PG is a protecting group;

W is a nucleobase;

$L^1$ is a straight chain or branched, substituted or unsubstituted, saturated or unsaturated, aliphatic or aromatic moiety having between 1 and about 60 carbon atoms and optionally including one or more heteroatoms, provided that $L^1$ includes one or more cleavable groups; and $Z^1$ is a first oligonucleotide.

In some embodiments, the first oligonucleotide is an LNA-modified first oligonucleotide. In some embodiments, the LNA-modified first oligonucleotide includes at least one L-configured LNA monomer. In some embodiments, the LNA-modified first oligonucleotide includes between 3 mer and 12 mer. In some embodiments, the LNA-first modified oligonucleotide includes a sequence having any of SEQ ID NOS: 1-22 or 29-50.

BRIEF DESCRIPTION OF THE FIGURES

For a general understanding of the features of the disclosure, reference is made to the drawings. In the drawings, like reference numerals have been used throughout to identify identical elements.

DETAILED DESCRIPTION

Figure 1A:
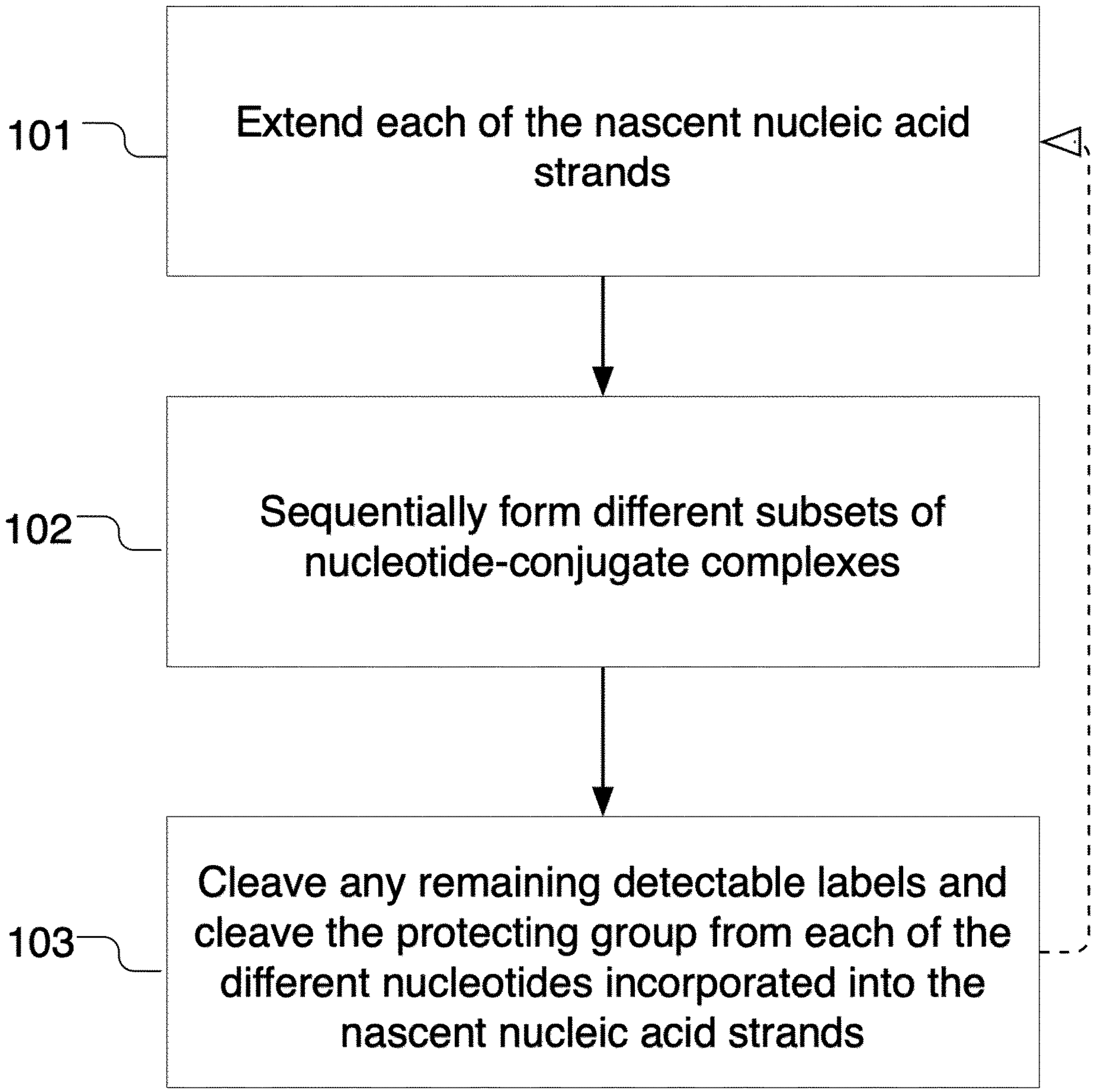
FIG. 1A provides a flowchart setting forth a method of sequencing in accordance with one embodiment of the present disclosure.

It should also be understood that, unless clearly indicated to the contrary, in any methods claimed herein that include more than one step or act, the order of the steps or acts of the method is not necessarily limited to the order in which the steps or acts of the method are recited.

As used herein, the singular terms "a," "an," and "the" include plural referents unless context clearly indicates otherwise. Similarly, the word "or" is intended to include "and" unless the context clearly indicates otherwise. The term "includes" is defined inclusively, such that "includes A or B" means including A, B, or A and B.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of" or "exactly one of." "Consisting essentially of," when used in the claims, shall have its ordinary meaning as used in the field of patent law.

As used herein, the terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used herein, the terms "analog" or "derivative" are used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

As used herein, the term "aliphatic" means a straight or branched hydrocarbon chain, which may be saturated or mono- or polyunsaturated. An unsaturated, aliphatic group contains one or more double and/or triple bonds. The branches of the hydrocarbon chain may include linear chains as well as non-aromatic cyclic elements. The hydrocarbon chain may, unless otherwise stated, be of any length, and contain any number of branches. Both the main chain as well as the branches may furthermore contain heteroatoms as for instance B, N, O, P, S, Se or Si.

As used herein, the term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone. In certain embodiments, a straight chain or branched chain alkyl has 30 or fewer carbon atoms in its backbone (e.g., $C_1$-$C_{30}$ for straight chain, $C_1$-$C_{30}$ for branched chain). Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. An "alkylaryl" or an "arylalkyl" moiety is an alkyl substituted with an aryl (e.g., phenylmethyl (benzyl)). The term "alkyl" also includes the side chains of natural and unnatural amino acids.

As used herein, the term "alkenyl" includes unsaturated aliphatic groups analogous in length and possible substitution to the alkyls described above, but that contain at least one double bond. For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 30 or fewer carbon atoms in its backbone (e.g., $C_2$-$C_{30}$ for straight chain, $C_3$-$C_{30}$ for branched chain). Moreover, the term alkenyl includes both "unsubstituted alkenyls" and "substituted alkenyls," the latter of which refers to alkenyl moieties having substituents replacing a hydrogen on one or more carbons of the hydrocarbon backbone. Such substituents can include, for example, alkyl groups, alkenyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Other examples of alkenyl groups include, but are not limited to, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, i-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl groups. Groups containing multiple double bonds may include but are not limited to buta-1,3-dienyl, penta-1,3-dienyl or penta-1,4-dienyl groups.

As used herein, the term "alkynyl" includes unsaturated aliphatic groups analogous in length and possible substitution to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups which include oxygen, nitrogen, sulfur or phosphorous atoms replacing one or more carbons of the hydrocarbon backbone. In certain embodiments, a straight chain or branched chain alkynyl group has 30 or fewer carbon atoms in its backbone (e.g., $C_2$-$C_{30}$ for straight chain, $C_3$-$C_{30}$ for branched chain). Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkenyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Groups containing multiple triple bonds may include but are not limited to buta-1,3-diynyl, penta-1,3-diynyl or penta-1,4-diynyl groups.

As used herein, the term "aromatic" means, unless otherwise stated, a planar cyclic hydrocarbon moiety of conjugated double bonds, which may be a single ring or include multiple fused or covalently linked rings. The main chain of the cyclic hydrocarbon moiety may, unless otherwise stated, be of any length and contain any number of heteroatoms, as for instance N, O and S. The aromatic group may be substituted by alkyl groups or heteroatoms like O, S, N, P or Si.

As used herein, the term "heteroalkyl," by itself or in combination with another term, means, unless otherwise stated, a stable straight or branched chain, or combinations thereof, consisting of at least one carbon atom and at least one heteroatom selected from the group consisting of O, N, P, Si, and S, and wherein the nitrogen, phosphorus, and sulfur atoms may optionally be oxidized, and the nitrogen heteroatom may optionally be quaternate. The heteroatom(s) 0, N, P, S, and Si may be placed at any interior position of the heteroalkyl group or at the position at which the alkyl group is attached to the remainder of the molecule. A heteroalkyl is not cyclized. Examples include, but are not limited to: $-CH_2-CH_2-O-CH_3$, $-CH_2-CH_2-NH-CH_3$, $-CH_2-CH_2-N(CH_3)-CH_3$, $-CH_2-S-CH_2-CH_3$, $-CH_2-O-CH_3$, $-S(O)-CH_3$, $-CH_2-CH_2-S(O)_2-CH_3$, $-CH=CH-O-CH_3$, $-Si(CH_3)_3$, $-CH_2-CH=N-OCH_3$, $-CH=CH-N(CH_3)-CH_3$, $-O-CH_3$, $-O-CH_2-CH_3$, and $-CN$. Up to two heteroatoms may be consecutive, such as, for example, $-CH_2-NH-OCH_3$.

As used herein, the terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Cycloalkyls and heterocycloalkyl can be further substituted, e.g., with any of the substituents described herein.

Each of the above terms (e.g., "alkyl," "aromatic," "heteroalkyl," "cycloalkyl," etc.) includes both substituted and unsubstituted forms of the indicated radical. In that regard, whenever a group or moiety is described as being "substituted" or "optionally substituted" (or "optionally having" or "optionally comprising") that group may be unsubstituted or substituted with one or more of the indicated substituents. Likewise, when a group is described as being "substituted or unsubstituted" if substituted, the substituent(s) may be selected from one or more of the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, cyanate, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an ether, amino (e.g. a mono-substituted amino group or a di-substituted amino group), and protected derivatives thereof. Any of the above groups may include one or more heteroatoms, including O, N, or S. For example, where a moiety is substituted with an alkyl group, that alkyl group may comprise a heteroatom selected from O, N, or S (e.g. $-(CH_2-CH_2-O-CH_2-CH_3)$).

As used herein, the term "antibody," refers to immunoglobulins or immunoglobulin-like molecules, including by way of example and without limitation, IgA, IgD, IgE, IgG and IgM, combinations thereof, and similar molecules produced during an immune response in any vertebrate, (e.g., in mammals such as humans, goats, rabbits and mice) and antibody fragments (such as F(ab')2 fragments, Fab' fragments, Fab'-SH fragments and Fab fragments as are known in the art, recombinant antibody fragments (such as sFv fragments, dsFv fragments, bispecific sFv fragments, bispecific dsFv fragments, F(ab)'2 fragments, single chain Fv proteins ("scFv"), disulfide stabilized Fv proteins ("dsFv"), diabodies, and triabodies (as are known in the art), and camelid antibodies) that specifically bind to a molecule of interest (or a group of highly similar molecules of interest) to the substantial exclusion of binding to other molecules. Antibody further refers to a polypeptide ligand including at least a light chain or heavy chain immunoglobulin variable region which specifically recognizes and binds an epitope of an antigen. Antibodies may be composed of a heavy and a light chain, each of which has a variable region, termed the variable heavy (VH) region and the variable light (VL) region. Together, the VH region and the VL region are responsible for binding the antigen recognized by the antibody. The term antibody also includes intact immunoglobulins and the variants and portions of them well known in the art.

As used herein, the terms "couple" or "coupling" refer to the joining, bonding (e.g. covalent bonding), or linking of one molecule or atom to another molecule or atom.

As used herein, the term "complementary" refers to the ability to form favorable thermodynamic stability and specific pairing between the bases of two nucleotides at an appropriate temperature and ionic buffer conditions. Complementarity is achieved by distinct interactions between the nucleobases adenine, thymine (uracil in RNA), guanine and cytosine, where adenine pairs with thymine or uracil, and guanine pairs with cytosine.

As used herein, the term "heteroatom" is meant to include boron (B), oxygen (O), nitrogen (N), sulfur (S), phosphorus (P), and silicon (Si). In some embodiments, a "heterocyclic ring" may comprise one or more heteroatoms. In other embodiments, an aliphatic group may comprise or be substituted by one or more heteroatoms.

As used herein, the term "hybridize" refers to the base-pairing between different nucleic acid molecules consistent with their nucleotide sequences.

As used herein, the term "label" refers to a detectable moiety that may be atoms or molecules, or a collection of atoms or molecules. A label may provide an optical, electrochemical, magnetic, or electrostatic (e.g., inductive, capacitive) signature which may be detected.

As used herein, the term "nucleic acid" can include one or more subunits (naturally occurring, synthetic, or modified nucleobases) including, but not limited to, adenine (A), cytosine (C), guanine (G), thymine (T) and uracil (U). Derivatives of these bases are exemplified in PCR Systems, Reagents and Consumables (Perkin Elmer Catalogue 1996-1997, Roche Molecular Systems, Inc., Branchburg, N.J., USA), which is entirely incorporated herein by reference. In some examples, a nucleic acid is deoxyribonucleic acid (DNA) or ribonucleic acid (RNA), or derivatives thereof. A nucleic acid may be single-stranded or double stranded. A nucleic acid can include any nucleic acid molecule, including, without limitation, DNA, RNA and hybrids or variants thereof.

As used herein, the term "nucleic acid template" refers to a nucleic acid or portion thereof that is capable of use as a guide for polymerase catalyzed replication. A nucleic acid molecule can include multiple templates along its length or, alternatively, only a single template may be used in a particular embodiment herein. A nucleic acid template can also function as a guide for ligase-catalyzed primer extension.

As used herein, the term "nucleobase" refers to a heterocyclic moiety capable of non-covalently pairing with another nucleobase. The term "nucleobase" encompasses both "unmodified nucleobases" and "modified nucleobases." A "naturally occurring nucleobase" or an "unmodified nucleobase" (used interchangeably) refer to a nucleobase that is unmodified relative to its naturally occurring form. Likewise, a "modified nucleobase" means any substitution and/or change from a natural nucleobase. Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to oligonucleotides. Modified nucleobases include synthetic and natural nucleobases such as, for example, 5-methylcytosine (5-me-C). Certain nucleobase substitutions, including 5-methylcytosine substitutions, are particularly useful for increasing the binding affinity of a complementary oligonucleotide for a target nucleic acid. For example, 5-methylcytosine substitutions have been shown to increase nucleic acid duplex stability by about 0.6 to about 1.2° C. (see Sanghvi, Y. S., Crooke, S. T. and Lebleu, B., eds., Antisense Research and Applications, CRC Press, Boca Raton, 1993, pp. 276-278, the disclosure of which is hereby incorporated by reference herein in its entirety).

Additional modified nucleobases include, but are not limited to, 5-hydroxymethyl cytosine, xanthine, hypoxanthine, 7-methylguanine, 2-aminoadenine, 2-aminopurine, iso-C, iso-G, thioT, thioG, 5,6-dihydrouracil, 6-methyladenine, 2-propylguanine and other alkyl derivatives of adenine and guanine, 2-thiouracil, 2-thiothymine and 2-thiocytosine, 5-halouracil and cytosine such as 5-bromo, 5-trifluoromethyl and other 5-substituted uracils and cytosines, 5-propynyl ($-C\equiv C-CH_3$) uracil and cytosine and other alkynyl derivatives of pyrimidine bases, 6-aza uracil, cytosine and thymine, uracil-5-yl (pseudouracil), 4-thiouracil, 8-halo, 8-amino, 8-thiol, 8-thioalkyl, 8-hydroxy and other 8-substituted adenines and guanines, 7-methylguanine and 7-methyladenine, 2-F-adenine, 8-azaguanine and 8-azaadenine, 7-deazaguanine and 7-deazaadenine and 3-deazaguanine and 3-deazaadenine, 8-aza-7-deazaguanine and 8-aza-7-deazaadenine. Additional nucleobases are disclosed in Greco et. al., Synthesis and site-specific incorporation of a simple fluorescent pyrimidine, Nature Protocols, vol. 2, no. 2, 2007; Dien et. al., Progress Toward a Semi-Synthetic Organism with an Unrestricted Expanded Genetic Alphabet, J. Am. Chem. Soc. 2018, 140, 16115-16123; Zhang et. al., Evolution of Functional Six-Nucleotide DNA, J. Am. Chem. Soc. 2015, 137, 6734-6737; Biondi et. al. Artificially Expanded Genetic Information Systems for New Aptamer Technologies, Biomedicines 2018, 6, 53; Liu et. al., Helix-Forming Properties of Size-Expanded DNA, an Alternative Four-Base Genetic Form, J. Am. Chem. Soc. 9 Vol. 127, No. 5, 2005, 1396-1402; Tor et. al., Designing new isomorphic fluorescent nucleobase analogues: the thieno[3,2-d]pyrimidine core, Tetrahedron 63 (2007) 3608-3614; Laos et. al., Directed Evolution of Polymerases to Accept Nucleotides with Nonstandard Hydrogen Bond Patterns, Biochemistry 2013, 52, 5288-5294; Krueger et. al., Synthesis and Properties of Size-expanded DNAs: Toward Designed, Functional Genetic Systems, Acc Chem Res. 2007 February; 40(2): 141-150; Srivatsan et. al., A highly fluorescent nucleoside analog based on thieno[3,4-d]pyrimidine senses mismatched pairing, Org. Biomol. Chem., 2008, 6, 1334-1338; Kim et. al., Synthesis and Properties of 5-Cyano-Substituted Nucleoside Analog with a Donor-Donor-Acceptor Hydrogen-Bonding Pattern, J. Org. Chem. 2012, 77, 3664-3669; and Noe et. al., Oligodeoxynucleotides Containing Multiple Thiophene-Modified Isomorphic Fluorescent Nucleosides, J. Org. Chem. 2013, 78, 8123-8128, the disclosures of which are hereby incorporated by reference herein in their entireties.

As used herein, the term "nucleoside" refers to a nucleobase covalently attached to a sugar, such as ribose or 2'-deoxyribose.

As used herein, the term "nucleotide" refers to a nucleoside covalently attached to a phosphate or polyphosphate, such as adenosine 5'-monophosphate (AMP), adenosine 5'-diphosphate (ADP), adenosine 5'-triphosphate (ATP), adenosine 5'-tetraphosphate or its 2'-deoxy derivatives.

As used herein, the term “oligonucleotide,” refers to an oligomer of nucleotide or nucleoside monomer units wherein the oligomer optionally includes non-nucleotide monomer units, and/or other chemical groups attached at internal and/or external positions of the oligomer. The oligomer can be natural or synthetic and can include naturally-occurring oligonucleotides, or oligomers that include nucleosides with non-naturally-occurring (or modified) bases, sugar moieties, phosphodiester-analog linkages, and/or alternative monomer unit chiralities and isomeric structures (e.g., 5'- to 2'-linkage, L-nucleosides, α-anomer nucleosides, β-anomer nucleosides, locked nucleic acids (LNA), peptide nucleic acids (PNA)).

As used herein, the term “polymerase” refers to any enzyme capable of catalyzing a polymerization reaction. Examples of polymerases include, without limitation, a nucleic acid polymerase, a transcriptase or a ligase. A polymerase can be a polymerization enzyme. A “DNA polymerase” catalyzes the polymerization of deoxynucleotides. An “RNA polymerase” catalyzes the polymerization of ribonucleotides. A polymer may include a reverse transcriptase, an enzyme used to generate complementary DNA (cDNA) from an RNA template.

As used herein, a “polynucleotide” is a polymer or oligomer including at least two nucleotides. A polynucleotide or oligonucleotide can comprise a DNA polynucleotide or oligonucleotide, an RNA polynucleotide or oligonucleotide, or one or more sections of DNA polynucleotide or oligonucleotide and/or RNA polynucleotide or oligonucleotide.

As used herein, the terms “reactive group” or “reactive functional group” refer to a functional group that are capable of chemically associating with, interacting with, hybridizing with, hydrogen bonding with, or coupling with a functional group of a different moiety. In some embodiments, a “reaction” between two reactive groups or two reactive functional groups may mean that a covalent linkage is formed between two reactive groups or two reactive functional groups; or may mean that the two reactive groups or two reactive functional groups associate with each other, interact with each other, hybridize to each other, hydrogen bond with each other, etc. In some embodiments, the “reaction” thus includes binding events, such as the binding of a hapten with an anti-hapten antibody, or a guest molecule associating with a supramolecular host molecule.

As used herein, the term “sequence,” when used in reference to a nucleic acid, refers to the order of nucleotides (or bases) in the nucleic acids. In cases, where different species of nucleotides are present in the nucleic acid, the sequence includes an identification of the species of nucleotide (or base) at respective positions in the nucleic acid. A sequence is a property of all or part of a nucleic acid molecule. The term can be used similarly to describe the order and positional identity of monomeric units in other polymers such as amino acid monomeric units of protein polymers.

As used herein, the term “sequencing” refers to the determination of the order and position of bases in a nucleic acid.

As used herein, the terms “template nucleic acid,” “target polynucleotide molecule,” and “target nucleic acid” can be used interchangeably and refer to a nucleic acid molecule that is the subject of an amplification reaction that may optionally be interrogated by a sequencing reaction in order to derive its sequence information. The template nucleic acid may be a nucleic acid which has been generated by a clonal amplification method and which may be immobilized on a solid support, i.e. immobilized on beads or an array.

The headings provided herein are for convenience only and do not interpret the scope or meaning of the disclosed embodiments.

Nucleotides, Nucleosides, Oligonucleotides, Polynucleotides

The present disclosure is directed to nucleotides, nucleosides, oligonucleotides, and/or polynucleotides (or any salts thereof) including a sugar, e.g. ribose or deoxyribose, and a nucleobase. In some embodiments, nucleotides of the present disclosure are incorporated into nascent nucleic acid strands, whereby the incorporated nucleotides may be reacted with a conjugate to form an incorporated nucleotide-conjugate complex as described herein.

In some embodiments, nucleotides, nucleosides, oligonucleotides, and/or polynucleotides (including any salts thereof) according to the present disclosure have a structure defined by Formula (IA):

(IA)

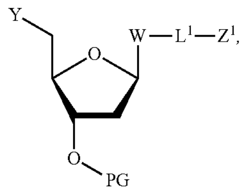

wherein

- Y is —OH, —O—P(O)(OH)[—O—P(O)(OH)]$_z$—OH or —O—P(O)(OH)-oligonucleotide, where z is 0 or an integer ranging from 1 to 5;
- PG is a protecting group;
- W is a nucleobase;
- $L^1$ is a straight chain or branched, substituted or unsubstituted, saturated or unsaturated, aliphatic or aromatic moiety having between 1 and about 60 carbon atoms and optionally substituted with one or more heteroatoms, provided that $L^1$ includes one or more cleavable groups; and
- $Z^1$ is a reactive group.

In some embodiments, z is 2.

In some embodiments, the moiety $L^1$ may be attached at any position on the nucleobase (“W”) provided that Watson-Crick base pairing can still be carried out. In some embodiments, and in the context of purine bases, the moiety $L^1$ is attached via an 7-position of a 7-deazapurine, via an 8-modified purine, via an N-6 modified adenine, or an N-2 modified guanine. In some embodiments, and in the context of pyrimidines, the attachment of the moiety $L^1$ is via the 5-position on cytosine, thymine or uracil and the N-4 position on cytosine.

As noted above, in some embodiments, the moiety $L^1$ includes from between 1 and about 60 carbon atoms. In some embodiments, the moiety $L^1$ includes from between 1 and about 50 carbon atoms. In some embodiments, the moiety $L^1$ includes from between 1 and about 40 carbon atoms. In some embodiments, the moiety $L^1$ includes from between 1 and about 35 carbon atoms. In some embodiments, the moiety $L^1$ includes from between 1 and about 30 carbon atoms. In other embodiments, the moiety $L^1$ includes from between 2 and about 25 carbon atoms. In yet other embodiments, the moiety $L^1$ includes from between about 5 and about 20 carbon atoms. In yet other embodiments, the moiety $L^1$ includes from between about 5 and about 15 carbon atoms. In further embodiments, the moiety $L^1$ includes from between about 10 and about 20 carbon atoms.

In some embodiments, the moiety $L^1$ has a molecular weight ranging from about 50 g/mol to about 1000 g/mol. In other embodiments, the moiety $L^1$ has a molecular weight ranging from about 40 g/mol to about 400 g/mol. In other embodiments, the moiety $L^1$ has a molecular weight ranging from about 50 g/mol to about 300 g/mol. In other embodiments, the moiety $L^1$ has a molecular weight ranging from about 50 g/mol to about 250 g/mol. In some embodiments, the moiety $L^1$ has a length ranging from between about 0.5 nm to about 70 nm. In some embodiments, the moiety $L^1$ has a length ranging from between about 0.5 nm to about 60 nm. In some embodiments, the moiety $L^1$ has a length ranging from between about 0.5 nm to about 50 nm. In some embodiments, the moiety $L^1$ has a length ranging from between about 0.5 nm to about 40 nm. In some embodiments, the moiety $L^1$ has a length ranging from between about 1 nm to about 40 nm.

In some embodiments, the moiety $L^1$ is a substituted or unsubstituted alkyl group or heteroalkyl group having between 1 and about 40 carbon atoms and which includes one or more cleavable groups. In some embodiments, the moiety $L^1$ is a substituted or unsubstituted alkyl group or heteroalkyl group having between 1 and about 30 carbon atoms and which includes one or more cleavable groups. In some embodiments, the moiety $L^1$ is a substituted or unsubstituted alkyl group or heteroalkyl group having between 1 and about 20 carbon atoms and which includes one or more cleavable groups.

In some embodiments, the moiety $L^1$ is a substituted or unsubstituted alkenyl group or heteroalkenyl group having between 2 and about 40 carbon atoms and which includes one or more cleavable groups. In some embodiments, the moiety $L^1$ is a substituted or unsubstituted alkenyl group or heteroalkenyl group having between 2 and about 30 carbon atoms and which includes one or more cleavable groups. In some embodiments, the moiety $L^1$ is a substituted or unsubstituted alkenyl group or heteroalkenyl group having between 2 and about 20 carbon atoms and which includes one or more cleavable groups.

In some embodiments, the moiety $L^1$ is a substituted or unsubstituted alkynyl group or heteroalkynyl group having between 2 and about 40 carbon atoms and which includes one or more cleavable groups. In some embodiments, the moiety $L^1$ is a substituted or unsubstituted alkynyl group or heteroalkynyl group having between 2 and about 30 carbon atoms and which includes one or more cleavable groups. In some embodiments, the moiety $L^1$ is a substituted or unsubstituted alkynyl group or heteroalkynyl group having between 2 and about 20 carbon atoms and which includes one or more cleavable groups.

As noted above, the moiety $L^1$ includes one or more groups which are capable of being cleaved, e.g. a photocleavable group, an enzymatically cleavable group, a chemically cleavable group, and a group cleavable at certain pHs. While the moiety $L^1$ includes a cleavable group, it is not meant to imply that the entire moiety $L^1$ is to be removed from a nucleobase to which it is attached. Rather, a cleavage site within the moiety $L^1$ can be located at any position within the moiety $L^1$ that ensures that part of the moiety $L^1$ remains attached to the nucleobase after cleavage. In some embodiments, the use of a cleavable linker ensures that any component further coupled to the nucleotide or nucleoside of Formula (IA) may be subsequently removed. In some embodiments, the cleavable group may be cleaved by any suitable method, including exposure to acids, bases, nucleophiles, electrophiles, radicals, metals, reducing or oxidizing agents, light, temperature, enzymes, etc. Non-limiting examples of suitable cleavable groups include disulfide groups, alpha-azidoethers, nitrobenzyl-based groups, and phenacyl groups. Other non-limiting examples of suitable cleavable groups are described further herein. Yet other examples of cleavage groups or classes of cleavage groups which may be utilized include those described in U.S. Pat. Nos. 9,605,310, 7,414,116, and 7,057,026, the disclosures of which are hereby incorporated by reference herein in their entireties.

In some embodiments, the moiety $L^1$ has the general structure -[Linker]-[Cleavable Group]-[Linker]-, where each [Linker] may be the same or different. In some embodiments, each [Linker] is independently a straight chain or branched, substituted or unsubstituted, saturated or unsaturated, aliphatic or aromatic moiety having between 1 and 45 about carbon atoms, and which is optionally substituted with one or more heteroatoms. In some embodiments, each [Linker] is independently a straight chain or branched, substituted or unsubstituted, saturated or unsaturated, aliphatic or aromatic moiety having between 1 and about 35 carbon atoms, and which is optionally substituted with one or more heteroatoms. In some embodiments, each [Linker] is independently a straight chain or branched, substituted or unsubstituted, saturated or unsaturated, aliphatic or aromatic moiety having between 1 and about 25 carbon atoms, and which is optionally substituted with one or more heteroatoms. In some embodiments, each [Linker] is independently a straight chain or branched, substituted or unsubstituted, saturated or unsaturated, aliphatic or aromatic moiety having between 1 and about 20 carbon atoms, and which is optionally substituted with one or more heteroatoms. In some embodiments, each [Linker] is independently a straight chain or branched, substituted or unsubstituted, saturated or unsaturated, aliphatic or aromatic moiety having between 1 and about 10 carbon atoms, and which is optionally substituted with one or more heteroatoms.

In some embodiments, each [Linker] is independently a substituted or unsubstituted alkenyl group or heteroalkenyl group having between 2 and about 45 carbon atoms. In some embodiments, each [Linker] is independently a substituted or unsubstituted alkenyl group or heteroalkenyl group having between 2 and about 35 carbon atoms. In some embodiments, each [Linker] is independently a substituted or unsubstituted alkenyl group or heteroalkenyl group having between 2 and about 25 carbon atoms. In some embodiments, each [Linker] is independently a substituted or unsubstituted alkenyl group or heteroalkenyl group having between 2 and about 20 carbon atoms. In some embodiments, each [Linker] is independently a substituted or unsubstituted alkenyl group or heteroalkenyl group having between 2 and about 10 carbon atoms. In some embodiments, the -[Cleavable Linker]- is a photocleavable group, an enzymatically cleavable group, a chemically cleavable group, and a group cleavable at certain pHs.

In some embodiments, each [Linker] is independently a substituted or unsubstituted alkynyl group or heteroalkynyl group having between 2 and about 45 carbon atoms. In some embodiments, each [Linker] is independently a substituted or unsubstituted alkynyl group or heteroalkynyl group having between 2 and about 35 carbon atoms. In some embodiments, each [Linker] is independently a substituted or unsubstituted alkynyl group or heteroalkynyl group having between 2 and about 25 carbon atoms. In some embodiments, each [Linker] is independently a substituted or unsubstituted alkynyl group or heteroalkynyl group having between 2 and about 20 carbon atoms. In some embodiments, each [Linker] is independently a substituted or unsubstituted alkynyl group or heteroalkynyl group having between 2 and about 10 carbon atoms. In some embodiments, the -[Cleavable Linker]- is a photocleavable group, an enzymatically cleavable group, a chemically cleavable group, and a group cleavable at certain pHs.

In some embodiments, each [Linker] is independently a substituted or unsubstituted alkyl group or heteroalkyl group having between 1 and about 45 carbon atoms. In some embodiments, each [Linker] is independently a substituted or unsubstituted alkyl group or heteroalkyl group having between 1 and about 35 carbon atoms. In some embodiments, each [Linker] is independently a substituted or unsubstituted alkyl group or heteroalkyl group having between 1 and about 25 carbon atoms. In some embodiments, each [Linker] is independently a substituted or unsubstituted alkyl group or heteroalkyl group having between 1 and about 20 carbon atoms. In some embodiments, each [Linker] is independently a substituted or unsubstituted alkyl group or heteroalkyl group having between 1 and about 10 carbon atoms. In some embodiments, the -[Cleavable Linker]- is a photocleavable group, an enzymatically cleavable group, a chemically cleavable group, and a group cleavable at certain pHs.

In some embodiments, the reactive group $Z^1$ is a first member of a pair of reactive groups. For example, and as described further herein, $Z^1$ may be first reactive group member which orthogonally reacts with a second reactive group member $Z^2$, such as a reactive group member $Z^2$ of a conjugate having any of Formulas (IIA) to (IIE), and as described herein.

In some embodiments, $Z^1$ includes a reactive group capable of participating in a "click chemistry" reaction. Examples of suitable reactive functional groups (e.g. pairs of functional groups that are reactive with each other) suitable for participating in a "click chemistry" reaction are set forth in Table 1 below. Generally, "click chemistry" encourages reactions that have modular applications that are wide in scope, that have a high chemical yield, that generate inoffensive by-products, that are chemospecific, that require simple reaction conditions, that use readily available starting materials and reagents, that are solvent free or use benign solvents (such as water), that lead to easy product isolation, that have a large thermodynamic driving force to favor a reaction with a single reaction product, and/or that have a high atom economy. While certain of the general criteria can be subjective in nature, not all criteria need to be met.

"Click chemistry" is a chemical philosophy, independently defined by the groups of Sharpless and Meldal, that describes chemistry tailored to generate substances quickly and reliably by joining small units together. "Click chemistry" has been applied to a collection of reliable and self-directed organic reactions (Kolb, H. C.; Finn, M. G.; Sharpless, K. B. Angew). Chem. Int. Ed. 2001, 40, 2004-2021). For example, the identification of the copper catalyzed azide-alkyne [3+2]cycloaddition as a highly reliable molecular connection in water (Rostovtsev, V. V.; et al. Angew. Chem. Int. Ed. 2002, 41, 2596-2599) has been used to augment several types of investigations of biomolecular interactions (Wang, Q.; et al. J. Am. Chem. Soc. 2003, 125, 3192-3193; Speers, A. E.; et al. J. Am. Chem. Soc. 2003, 125, 4686-4687; Link, A. J.; Tirrell, D. A. J. Am. Chem. Soc. 2003, 125, 11164-11165; Deiters, A.; et al. J. Am. Chem. Soc. 2003, 125, 11782-11783). In addition, applications to organic synthesis (Lee, L. V.; et al. J. Am. Chem. Soc. 2003, 125, 9588-9589), drug discovery (Kolb, H. C.; Sharpless, K. B. Drug Disc. Today 2003, 8, 1128-1137; Lewis, W. G.; et al. Angew. Chem. Int. Ed. 2002, 41, 1053-1057), and the functionalization of surfaces (Meng, J.-C.; et al. Angew. Chem. Int. Ed. 2004, 43, 1255-1260; Fazio, F.; et al. J. Am. Chem. Soc. 2002, 124, 14397-14402; Collman, J. P.; et al. Langmuir 2004, ASAP, in press; Lummerstorfer, T.; Hoffmann, H. J. Phys. Chem. B 2004, in press) have also appeared.

In some embodiments, $Z^1$ includes a reactive group capable of undergoing a Cu(I)-catalyzed azide-alkyne cycloaddition (CuAAC) (see, e.g., Meldal et. al., "Cu-Catalyzed Azide-Alkyne Cycloaddition," Chem Rev. 2008, 108, 8, 2952-3015). In some embodiments, $Z^1$ includes a reactive group capable of undergoing a copper-free strain-promoted azide-alkyne cycloaddition (SPAAC). In some embodiments, $Z^1$ includes a reactive group capable of undergoing a chelation-assisted Cu(II) acetate accelerated azide-alkyne cycloaddition (CuAAC). In some embodiments, $Z^1$ includes a reactive group capable of undergoing an inverse-demand Diels-Alder cycloaddition reaction (e.g. tetrazine strained-alkene click chemistry).

TABLE 1

First and second members of reactive functional group pairs.

| Reactive Functional Group on a First Member of a Pair of Click Conjugates | Reactive Functional Group on a Second Member of a Pair of Click Conjugates |
|---|---|
| Alkyne | Azide |
| Azide | Alkyne |
| diarylcyclooctyne ("DBCO") | Azide |
| Alkene | Tetrazine |
| Trans-cyclooctene ("TCO") | Tetrazine |
| Maleimide | Thiol |
| DBCO | 1,3-Nitrone |
| Aldehyde or ketone | Hydrazine |
| Aldehyde or ketone | Hydroxylamine |
| Azide | DBCO |
| Tetrazine | TCO |
| Thiol | Maleimide |
| 1,3-Nitrone | DBCO |
| Hydrazine | Aldehyde or ketone |
| Hydroxylamine | Aldehyde or ketone |
| Tetrazine | Alkene |

In some embodiments, $Z^1$ includes a reactive group which is capable of participating in a binding event. Examples of binding events include, but are not limited to, the hybridization of oligonucleotides to each other, the binding of a hapten to an antibody or a variant thereof, and host-guest molecule interactions (i.e. the interaction of a host molecule and a guest molecule).

As such, in some embodiments, $Z^1$ includes a specific binding entity. As used herein, the term "specific binding entity" refers to a member of a specific-binding pair. Specific binding pairs are pairs of molecules that are characterized in that they bind each other to the substantial exclusion of binding to other molecules (for example, specific binding pairs can have a binding constant that is at least about $10^3$ $M^{-1}$ greater, at least about $10^4$ $M^{-1}$ greater, or at least about $10^5$ $M^{-1}$ greater than a binding constant for either of the two members of the binding pair with other molecules in a reaction mixture or sample).

In some embodiments, the specific binding entity is a protein, such an antibody, an antibody fragment, a lectin, an avidin (such as a streptavidin), and protein A. In some embodiments, the antibody is an anti-hapten antibody.

In other embodiments, the specific binding entity is a hapten. As used herein, "haptens" are small molecules that can combine specifically with an antibody, but typically are substantially incapable of being immunogenic except in combination with a carrier molecule. Non-limiting examples of haptens include pyrazoles (e.g. nitropyrazoles); nitrophenyl compounds; benzofurazans; triterpenes; ureas (e.g. phenyl ureas); thioureas (e.g. phenyl thioureas); rotenone and rotenone derivatives; oxazoles (e.g. oxazole sulfonamides); and thiazoles (e.g. thiazole sulfonamides); coumarin and coumarin derivatives; and cyclolignans (e.g. podophyllotoxin and podophyllotoxin derivatives). In some embodiments, the hapten is selected from benzofuran haptens and thiazolesulfonamide haptens. In some embodiments, the hapten is selected from 5-nitro-3-pyrazolecarbamide (NP), 2-acetamido-4-methyl-5-thiazolesulfonamide (TS), 7-(diethylamino)-2-oxo-2H-chromene-3-carboxyylic acid (DCC), digoxigenin (DIG), 2,4-dinitrophenyl (DNP), fluorescein, 3-hydroxy-2-quinoxalinecarbamide, and 2,1,3-benzoxadiazole-5-carbamide (BF). Other haptens suitable for use in the present disclosure include those set forth in U.S. Pat. Nos. 8,846,320; 8,618,265; 7,695,929; 8,481,270; and 9,017,954, the disclosures of which are hereby incorporated by reference herein in their entireties.

In some embodiments, $Z^1$ includes an oligonucleotide. In some embodiments, the oligonucleotide is between about 3 to about 30 nucleotides in length, i.e. between about 3 mer and about 30 mer. In other embodiments, the oligonucleotide is between about 3 to about 25 nucleotides in length. In other embodiments, the oligonucleotide is between about 3 to about 20 nucleotides in length. In other embodiments, the oligonucleotide is between about 3 to about 16 nucleotides in length. In other embodiments, the oligonucleotide is between about 3 to about 12 nucleotides in length. In other embodiments, the oligonucleotide is between about 3 to about 10 nucleotides in length. In yet other embodiments, the oligonucleotide is between about 4 to about 6 nucleotides in length. In further embodiments the oligonucleotide is between 5 to 6 nucleotides in length. Non-limiting examples of suitable oligonucleotide sequences are set forth in the Table 2 below.

TABLE 2

Non-limiting examples of oligonucleotide sequences.

| First oligonucleotide strand | Second oligonucleotide strand (complementary to the first strand) |
|---|---|
| cttcc (SEQ ID NO: 1) | ggaag (SEQ ID NO: 29) |
| gctcc (SEQ ID NO: 2) | ggagc (SEQ ID NO: 30) |
| gttggt (SEQ ID NO: 3) | accaac (SEQ ID NO: 31) |
| ctgtca (SEQ ID NO: 4) | tgacag (SEQ ID NO: 32) |
| tgctcc (SEQ ID NO: 5) | ggagca (SEQ ID NO: 33) |
| tcttcc (SEQ ID NO: 6) | ggaaga (SEQ ID NO: 34) |
| gttggtgt (SEQ ID NO: 7) | acaccaac (SEQ ID NO: 35) |
| gttggtg (SEQ ID NO: 8) | caccaac (SEQ ID NO: 36) |
| tgctcctg (SEQ ID NO: 9) | caggagca (SEQ ID NO: 37) |
| gtgcgtct (SEQ ID NO: 10) | agacgcac (SEQ ID NO: 38) |
| gttggtgt (SEQ ID NO: 11) | acaccaac (SEQ ID NO: 39) |
| tgctcctgt (SEQ ID NO: 12) | acaggagca (SEQ ID NO: 40) |
| gttggtgtg (SEQ ID NO: 13) | cacaccaac (SEQ ID NO: 41) |
| ttctcttcc (SEQ ID NO: 14) | ggaagagaa (SEQ ID NO: 42) |
| gttggtgtgttg (SEQ ID NO: 15) | caacacaccaac (SEQ ID NO: 43) |
| gttggtgtgttggtg (SEQ ID NO: 16) | caccaacacaccaac (SEQ ID NO: 44) |
| aaaaaaaaa (SEQ ID NO: 17) | ttttttttt (SEQ ID NO: 45) |
| aaaaaa (SEQ ID NO: 18) | tttttt (SEQ ID NO: 46 |
| tatcgc (SEQ ID NO: 19) | gcgata (SEQ ID NO: 47) |
| tctgac (SEQ ID NO: 20) | gtcaga (SEQ ID NO: 48) |
| agagag (SEQ ID NO: 21) | ctctct (SEQ ID NO: 49) |
| cacaca (SEQ ID NO: 22) | tgtgtg (SEQ ID NO: 50) |
| cagtggacgacgatagacat (SEQ ID NO: 23) | atgtctatcgtcgtccactg (SEQ ID NO: 51) |

TABLE 2-continued

| Non-limiting examples of oligonucleotide sequences. | |
|---|---|
| First oligonucleotide strand | Second oligonucleotide strand (complementary to the first strand) |
| agaggatcgaggagtacagg (SEQ ID NO: 24) | cctgtactcctcgatcctct (SEQ ID NO: 52) |
| agaaatggacgagatgctaa (SEQ ID NO: 25) | ttagcatctcgtccatttct (SEQ ID NO: 53) |
| actgaacttgtgagaaacgc (SEQ ID NO: 26) | gcgtttctcacaagttcagt (SEQ ID NO: 54) |
| atggagagtcaggcaagttt (SEQ ID NO: 27) | aaacttgcctgactctccat (SEQ ID NO: 55) |
| tgaagatgcgagtgatgaac (SEQ ID NO: 28) | gttcatcactcgcatcttca (SEQ ID NO: 56) |
| cactca (SEQ ID NO: 58) | tgagtg (SEQ ID NO: 57) |

In some embodiments, SEQ ID NOS: 1-22 and 29-50 (recited in Table 2) are LNA sequences. In other embodiments, SEQ ID NOS: 23-28 and 51-56 (recited in Table 2) are DNA sequences.

In some embodiments, the oligonucleotide includes one or more "mirror image," "L-configured" or "L-form" monomers (e.g. a monomer comprised of L-deoxyribose). It is believed that oligonucleotides comprised of L-form monomers are non-binding to naturally occurring, beta-D-configured nucleic acids, e.g. DNA molecules to be sequenced, sequencing primers, etc. Beta-L-configured oligonucleotides feature the same physicochemical characteristics as its beta-D-configured oligonucleotide counterparts (e.g. solubility, duplex stability, pairing selectivity). However, L-configured oligonucleotides are stable against nuclease digestion and form a left-handed-duplex. Additional types of monomers are disclosed in J. Am. Chem. Soc. 1991, 113 (21), 8174-8175; and Nucleic Acids Research, Volume 20, Issue 13, 11 Jul. 1992, Pages 3325-3332, the disclosures of which are hereby incorporated by reference herein in their entireties.

In other embodiments, the oligonucleotide includes one or more 2'-O-Me RNA bases. In yet other embodiments, the oligonucleotide includes one or more melting temperature (Tm) enhancing nucleobases. In some embodiments, the Tm enhancing nucleobases are selected from 5-propynyl-uracil, 5-propynyl-cytosine, 7-propynyl-7-deazaadenine, 7-propynyl-7-deazaguanine, 7-deaza-8-aza-7-bromo-guanine, and 7-deaza-8-aza-7-bromo-2-amino-adenine.

In some embodiments, the oligonucleotide is an "LNA-modified oligonucleotide." An "LNA-modified oligonucleotide" refers to an oligonucleotide that is either fully or partially modified with one or more LNA monomers ("locked nucleic acid" monomers). Thus, an "LNA-modified oligonucleotide" may be composed entirely of LNA monomers, or an "LNA-modified oligonucleotide" may comprise one LNA monomer, two LNA monomers, etc. As used herein, the term "LNA monomer" refers to a class of conformationally restricted nucleotide analogs whose ribose ring is constrained by a methylene linkage between the 2'-oxygen and the 4'-carbon, i.e. such as nucleotides which comprise a covalent bridge between the 2' and 4' position (a 2'-4' bridge). In some embodiments, LNA is applied in its beta-D-configuration which binds to naturally occurring nucleic acids with high affinity. alpha-L-LNA is also described and pairs also to naturally occurring nucleic acids with high affinity. In contrast to alpha-L-LNA beta-L-LNA does not bind to naturally occurring nucleic acids but only to beta-L-configured nucleic acids like beta-L-DNA or beta-L-LNA. LNA monomers are further described within U.S. Pat. Nos. 6,268,490, 6,794,499, 7,034,133, the disclosures of which are each hereby incorporated by reference herein in their entireties. The synthesis of locked nucleic acid derivatives is described in U.S. Pat. No. 8,492,390, the disclosure of which is hereby incorporated by reference herein in its entirety. Yet other monomers are disclosed in PCT Publication Nos. WO98/39352, WO99/14226, and WO200066604, the disclosures of which are hereby incorporated by reference herein in their entireties.

In some embodiments, the incorporation of one or more LNA monomers in an oligonucleotide increases the affinity of that oligonucleotide for its complementary RNA or DNA target by increasing the melting temperature (Tm) of the duplex. In some embodiments, the thermal stability of duplexes increases in the range of between about 3° C. to about 8° C., depending on the actual base, per LNA monomer present in the oligonucleotide (see Dwaine A. Braasch and David R. Corey, Chemistry and Biology 8 (2001) 1-7). Compared to DNA/LNA mixmers all-LNA duplexes form exceptionally stable duplexes. Thus, very short sequences can be used as binding pair. In some embodiments, the use of very short sequences is believed to be advantageous since the modification at the nucleotide can be kept as small as possible to minimally compromise incorporation efficiency by polymerase. Furthermore, beta-L-LNA has the additional advantage of not interfering with D-configured nucleic acids (e.g. with the DNA to be sequenced). In some embodiments, the oligonucleotide is comprised entirely of LNA monomers, e.g. an oligonucleotide including between 3 and 12 LNA monomers, between 4 and 8 LNA monomers, or between 5 and 6 LNA monomers. In some embodiments, the $Z^1$ group may comprise an oligonucleotide sequence including LNA monomers and having the sequence of any one of SEQ ID NOS: 1-22. The skilled artisan will appreciate that any introduced conjugate (described herein) will comprise a complementary oligonucleotide sequence including LNA monomers and having the sequence of any one of SEQ ID NOS: 29-50. For example, if a nucleotide includes a $Z^1$ group including an oligonucleotide having SEQ ID NO: 19, then an introduced conjugate will have a complementary sequence, namely SEQ ID NO: 47. In some embodiments first and second oligonucleotide sequences can be exchanged, i.e. the $Z^1$ group may comprise an oligonucleotide sequence including LNA monomers and having the sequence of any one of SEQ ID NOS: 29-50, then any introduced conjugate will comprise a complementary oligonucleotide sequence including LNA monomers and having the sequence of any one of SEQ ID NOS: 1-22.

In some embodiments, the oligonucleotide is a "PNA-modified oligonucleotide." A "PNA-modified oligonucleotide" refers to an oligonucleotide that is either fully or partially modified with one or more PNA monomers ("peptide nucleic acid" monomers). A PNA monomer refers to a class of nucleotide analogs in which the sugar phosphate backbone of natural nucleic acid has been replaced by a synthetic peptide backbone usually formed from N-(2-amino-ethyl)-glycine units, resulting in an achiral and uncharged mimic. It is believed that since PNA contains no charges, the binding hybridization between PNA and DNA is stronger than that between DNA and DNA for the same sequence. Similar to LNA/LNA duplexes, PNA/PNA duplexes have high duplex stability. In some embodiments, the oligonucleotide is comprised entirely of PNA monomers, e.g. an oligonucleotide including between 3 and 12 PNA monomers, between 4 and 8 PNA monomers, or between 5 and 6 PNA monomers. By way of example, an oligonucleotide may comprise 6 PNA monomers and have the sequence 5'-ctgtca-3' (SEQ ID NO: 4).

In some embodiments, the oligonucleotide is comprised of one or more gamma-PNA monomers. In some embodiments, one or more PNA monomers in an oligonucleotide may be substituted at its gamma carbon, such as with a charged moiety (e.g. a lysine group).

In some embodiments, $Z^1$ includes one of a host molecule or a guest molecule (i.e. one member of a host/guest system). A host-guest system includes a small guest molecule fitting into the cavity of a somewhat larger host molecule and held there by attractive noncovalent forces (e.g. hydrogen bonding and/or van der Waals attraction). Different types of host-guest systems exhibit a diversity of binding conformations and a wide range of binding affinities.

In some embodiments, the host molecule is a cucurbit[n]uril compound, while a guest molecule is any compound which may reside within a cavity of the cucurbit[n]uril compound. In some embodiments, the cucurbit[n]uril compound is cucurbit[6]uril, cucurbit[7]uril, or cucurbit[8]uril. Other host compounds include calixarenes, e.g. calix[4]arene.

In some embodiments, the guest molecule is an amino-adamantane. In some embodiments, the guest molecule is a dicationic ferrocene derivative (e.g. bis(trimethylammoniomethyl)ferrocene). In other embodiments, the guest molecule is a dicationic N-adamantyl ethylenediamine. In yet other embodiments, the host molecule is a cyclodextrin, such as beta-cyclodextrin.

Yet other host/guest molecules suitable for used in the present disclosure are described in U.S. Patent Publication Nos. 2005/0080068, 2009/0072191, 2010/0247477, and 2017/0028374, the disclosures of which are hereby incorporated by reference herein in their entireties. Even further host/guest molecules are further described by Rekharsky et. al., "A synthetic host-guest system achieves avidin-biotin affinity by overcoming enthalpy—entropy compensation," PNAS, Dec. 26, 2007, vol. 104, no. 52, 20737-20742; Moghaddam et. al., "Host-Guest Complexes with Protein-Ligand-like Affinities: Computational Analysis and Design," Journal of the American Chemical Society 2009, 131, 11, 4012-4021; Sonzini et. al., "High Affinity Recognition of a Selected Amino Acid Epitope within a Protein by Cucurbit[8]uril Complexation," Angewandte Chemie, Vol. 55, Issue 45, November 2016; Chakraborty et. al., "A styryl based fluorogenic probe with high affinity for a cyclodextrin derivative," Organic & Biomolecular Chemistry, Issue 28, 2019; Iwamoto et. al., "Energetics of guest binding to calix[4]arene molecular containers," Tetrahedron, Vol. 65, Issue 35, August 2009, 7259-7267, the disclosures of which are hereby incorporated by reference herein in their entireties.

In some embodiments, PG is any protecting group that prevents the incorporation of a molecule (e.g. another nucleotide, such as any of those of Formula (IA)) from reacting at the 3' position of the nucleotides of Formula (IA), but where the group PG may be removed under defined conditions (e.g. to allow polymerization to occur through the incorporation of additional nucleotides). Non-limiting examples of suitable protecting groups include azidomethyl, 3'-O-allyl (3'-O—$CH_2$—CH═$CH_2$), 3'-nitrate (3'-O—$NO_2$), 3-dithiomethyl (3'-O—$CH_2$—S—S—R), 3'-O-cyanoethyl (3'-O—$CH_2CH_2CN$), and 3'-O-cyanoethoxymethyl (3'-O—$CH_2$—O—$CH_2CH_2CN$). Yet additional protecting groups are described in U.S. Pat. No. 5,990,300; U.S. Publication Nos. 2015/0140561 and 2007/0117104; and in PCT Publication Nos. WO/2008/037568A2 and WO91/06678, the disclosures of which are each hereby incorporated by reference herein in their entireties. Yet further protecting groups are disclosed in PCT Application No. PCT/US19/66670, the disclosure of which is hereby incorporated by reference herein in its entirety. PCT Application No. PCT/US19/66670 describes, for instance, protecting groups having the formula —B($OR^1$)($OR^2$), where $R^1$ and $R^2$ are independently selected from —H, methyl, or ethyl.

In some embodiments, nucleotides, nucleosides, oligonucleotides, and/or polynucleotides (including any salts thereof) according to the present disclosure have a structure defined by Formula (IB):

(IB)

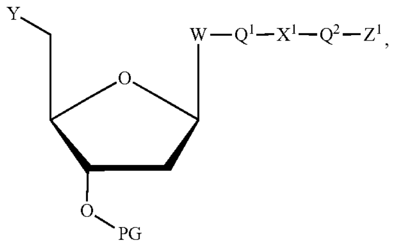

wherein

Y is —OH, —O—P(O)(OH)[—O—P(O)(OH)]$_z$—OH or —O—P(O)(OH)-oligonucleotide, where z is 0 or an integer ranging from 1 to 5.

PG is a protecting group;

W is a nucleobase;

$Q^1$ is a straight chain or branched, substituted or unsubstituted, saturated or unsaturated aliphatic moiety having between 1 and 25 carbon atoms and optionally substituted with one or more heteroatoms;

$Q^2$ is a straight chain or branched, substituted or unsubstituted, saturated or unsaturated, aliphatic or aromatic moiety having between 1 and 45 carbon atoms and optionally substituted with one or more heteroatoms;

$X^1$ is a cleavable group; and $Z^1$ is a reactive group.

In some embodiments, $Q^1$ comprises a $C_1$-$C_{25}$ straight chain or branched, substituted or unsubstituted alkyl or heteroalkyl group. In some embodiments, $Q^1$ comprises a $C_1$-$C_{20}$ straight chain or branched, substituted or unsubstituted alkyl or heteroalkyl group. In some embodiments, $Q^1$ comprises a $C_1$-$C_{15}$ straight chain or branched, substituted or unsubstituted alkyl or heteroalkyl group. In other embodiments, $Q^1$ comprises a $C_1$-$C_8$ straight chain or branched, substituted or unsubstituted alkyl or heteroalkyl, group. In yet other embodiments, $Q^1$ comprises a $C_1$-$C_6$ straight chain or branched, substituted or unsubstituted alkyl or heteroalkyl group. In yet further embodiments, $Q^1$ comprises a $C_1$-$C_4$ straight chain or branched, substituted or unsubstituted alkyl or heteroalkyl group. In even further embodiments, $Q^1$ comprises a $C_1$-$C_4$ straight chain or branched, substituted or unsubstituted alkyl group. In even further embodiments, $Q^2$ comprises a $C_1$-$C_4$ straight chain or branched alkyl group.

In some embodiments, $Q^1$ comprises a $C_3$-$C_6$ cycloalkyl group or heterocycloalkyl group. In some embodiments, $Q^1$ comprises a $C_3$-$C_4$ cycloalkyl group or heterocycloalkyl group. In some embodiments, $Q^1$ comprises a substituted or unsubstituted $C_5$-$C_7$ cycloalkyl group. In some embodiments, $Q^1$ comprises a substituted or unsubstituted $C_5$-$C_6$ cycloalkyl group. In some embodiments, $Q^1$ comprises a substituted or unsubstituted $C_5$-$C_7$ heterocycloalkyl group. In some embodiments, $Q^1$ comprises a substituted or unsubstituted $C_5$-$C_6$ heterocycloalkyl group.

In some embodiments, $Q^1$ comprises a $C_2$-$C_{25}$ substituted or unsubstituted alkenyl group. In some embodiments, $Q^1$ comprises a $C_2$-$C_{12}$ substituted or unsubstituted alkenyl group. In another embodiment, $Q^1$ comprises a $C_2$-$C_6$ substituted or unsubstituted alkenyl group. In some embodiments, $Q^1$ comprises a $C_2$-$C_{25}$ substituted or unsubstituted alkynyl group. In some embodiments, $Q^1$ comprises a $C_2$-$C_{12}$ substituted or unsubstituted alkynyl group. In another embodiment, $Q^1$ comprises a $C_2$-$C_6$ substituted or unsubstituted alkynyl group.

In some embodiments, $Q^2$ comprises a $C_1$-$C_{45}$ straight chain or branched, substituted or unsubstituted alkyl or heteroalkyl group. In some embodiments, $Q^2$ comprises a $C_1$-$C_{35}$ straight chain or branched, substituted or unsubstituted alkyl or heteroalkyl group. In some embodiments, $Q^2$ comprises a $C_1$-$C_{25}$ straight chain or branched, substituted or unsubstituted alkyl or heteroalkyl group. In other embodiments, $Q^2$ comprises a $C_1$-$C_{20}$ straight chain or branched, substituted or unsubstituted alkyl or heteroalkyl group. In yet other embodiments, $Q^2$ comprises a $C_1$-$C_{15}$ straight chain or branched, substituted or unsubstituted alkyl group or heteroalkyl group. In yet further embodiments, $Q^2$ comprises a $C_1$-$C_{10}$ straight chain or branched, substituted or unsubstituted alkyl or heteroalkyl group. In yet further embodiments, $Q^2$ comprises a $C_1$-$C_6$ straight chain or branched, substituted or unsubstituted alkyl or heteroalkyl group. In even further embodiments, $Q^2$ comprises a $C_1$-$C_6$ straight chain or branched, substituted or unsubstituted alkyl group. In even further embodiments, $Q^2$ comprises a $C_1$-$C_6$ straight chain or branched alkyl group.

In some embodiments, $Q^2$ comprises a $C_3$-$C_6$ cycloalkyl group or heterocycloalkyl group. In some embodiments, $Q^2$ comprises a $C_3$-$C_4$ cycloalkyl group or heterocycloalkyl group. In some embodiments, $Q^2$ comprises a substituted or unsubstituted $C_5$-$C_7$ cycloalkyl group. In some embodiments, $Q^2$ comprises a substituted or unsubstituted $C_5$-$C_6$ cycloalkyl group. In some embodiments, $Q^2$ comprises a substituted or unsubstituted $C_5$-$C_7$ heterocycloalkyl group. In some embodiments, $Q^2$ comprises a substituted or unsubstituted $C_5$-$C_6$ heterocycloalkyl group.

In some embodiments, $Q^2$ comprises a $C_2$-$C_{45}$ substituted or unsubstituted alkenyl group. In some embodiments, $Q^2$ comprises a $C_2$-$C_{25}$ substituted or unsubstituted alkenyl group. In some embodiments, $Q^2$ comprises a $C_2$-$C_{45}$ substituted or unsubstituted alkynyl group. In some embodiments, $Q^2$ comprises a $C_2$-$C_{25}$ substituted or unsubstituted alkynyl group.

In some embodiments, either $Q^1$ and/or $Q^2$ may independently include a polyethylene oxide moiety or a polypropylene oxide moiety. For example, either $Q^1$ and/or $Q^2$ may include the group $—[CH_2—CH_2—O]_s—$, where s is an integer ranging from 1 to about 27. In some embodiments, s ranges from 1 to 12. For example, $Q^2$ may include the group $—[CH_2—CH(CH_3)—O]_s—$, where s is an integer ranging from 1 to about 27. In some embodiments, s ranges from 1 to about 12.

In some embodiments, either $Q^1$ and/or $Q^2$ independently comprises a substituted or unsubstituted $C_5$-$C_7$ aryl group. In other embodiments, either $Q^1$ and/or $Q^2$ independently comprises a substituted or unsubstituted $C_5$-$C_6$ aryl group.

In some embodiments, $X^1$ may be any photocleavable, enzymatically cleavable, chemically cleavable, pH sensitive, etc. group. For example, $X^1$ is a group which may be cleaved upon exposure to an electromagnetic radiation source having a wavelength of between about 200 nm to about 400 nm (UV) or between about 400 nm to about 800 nm (visible). Examples of suitable photocleavable groups include, but are not limited to, arylcarbonylmethyl groups (e.g. 4-acetyl-2-nitrobenzyl, dimethylphenacyl (DMP)); 2-(alkoxymethyl)-5-methyl-α-chloroacetophenones, 2,5-dimethylbenzoyl oxiranes, benzoin groups (e.g. 3',5'-dimethoxybenzoin (DMB)), o-nitrobenzyl groups (e.g. 1-(2-nitrophenyl)ethyl (NPE), 1-(methoxymethyl)-2-nitrobenzene, 4,5-dimethoxy-2-nitrobenzyl (DMNB), α-carboxynitrobenzyl (α-CNB)); o-nitro-2-phenethyloxycarbonyl groups (e.g. 1-(2-nitrophenyl)ethyloxycarbonyl and 2-nitro-2-phenethyl derivatives); o-nitroanilides (e.g. acylated 5-bromo-7-nitroindolines); coumarin-4-yl-methyl groups (e.g. 7-methoxycoumarin derivatives); 9-substituted xanthenes, and arylmethyl groups (e.g. o-hydroxyarylmethyl groups).

In some embodiments, $X^1$ is a group that may be cleaved upon exposure to an electromagnetic radiation source having a wavelength of between about 700 nm to about 1000 nm. Suitable near-infrared photocleavable groups include cyanine groups, including $C_4$-dialkylamine-substituted heptamethine cyanines.

In some embodiments, $X^1$ is a group that may be chemically cleaved by different chemical reactants, including reducing agents or by induced changes in pH (e.g. cleavage of the group $X^1$ at a pH of less than about 7). Non-limiting examples of chemically cleavable groups include disulfide-based groups; diazobenzene groups (e.g. 2-(2-alkoxy-4-hydroxy-phenylazo); benzoic acid scaffolds; ester bond-based groups; and acidic sensitive groups (e.g. a dialkoxydiphenylsilane group or acylhydrazone group). Electrophilically cleaved groups (e.g. p-alkoxybenzyl esters and p-alkoxybenzyl amides) are believed to be cleaved by protons and include cleavages sensitive to acids.

In some embodiments, $X^1$ is a group that may be enzymatically cleaved including, but not limited to, trypsin cleavable groups and V8 protease cleavable groups. In some embodiments, the group may be enzymatically cleaved by one of an uracil-N-glycosylase, an RNase A, a beta-glucuronidase, a beta-galactosidase, or a TEV-protease.

In some embodiments, the groups W, $Z^1$, $Q^1$, $X^1$, and $Q^2$ are connected via a chemical bond, such as a C—C bond, an amide bond, an ester bond, an urea linkage, an urethane linkage, an amine bond, an ether bond, a thioether bond, a phosphate linkage, a 1, 2, 3-triazole linkage, or a dihydropyridazine linkage. By way of example, during synthesis $Q^1$ may include a first reactive functional group for coupling (e.g. an amine reactive group, a carboxylic acid reactive group, or a thiol reactive group) to a corresponding reactive functional group of $X^1$ (e.g. amine reactive group, a carboxylic acid reactive group, or a thiol reactive group). In some embodiments, amine-reactive groups include an isothiocyanate, an isocyanate, an acyl azide, an NHS ester, an acid chloride, such as sulfonyl chloride, aldehydes, epoxides and oxiranes, carbonates, arylating agents, imidoesters, carbodiimides, anhydrides, and combinations thereof. Suitable thiol-reactive functional groups include haloacetyl and alkyl halides, maleimides, aziridines, acryloyl derivatives, arylating agents, thiol-disulfide exchange reagents, such as pyridyl disulfides, TNB-thiol, and disulfide reductants, and combinations thereof. Carboxylate-reactive functional groups include diazoalkanes, diazoacetyl compounds, carbonyldiimidazole compounds, and carbodiimides. Hydroxyl-reactive functional groups include epoxides and oxiranes, carbonyldiimidazole, N,N'-disuccinimidyl carbonates or N-hydroxysuccinimidyl chloroformates, periodate oxidizing compounds, enzymatic oxidation, alkyl halogens, and isocyanates. Aldehyde and ketone-reactive functional groups include hydrazines, Schiff bases, reductive amination products, Mannich condensation products, and combinations thereof. Active hydrogen-reactive compounds include diazonium derivatives, Mannich condensation products, iodination reaction products, and combinations thereof. Photoreactive chemical functional groups include aryl azides, halogenated aryl azides, benzophonones, diazo compounds, diazirine derivatives, and combinations thereof.

Non-limiting examples of nucleotides having either Formula (IA) or (IB) are set forth below:

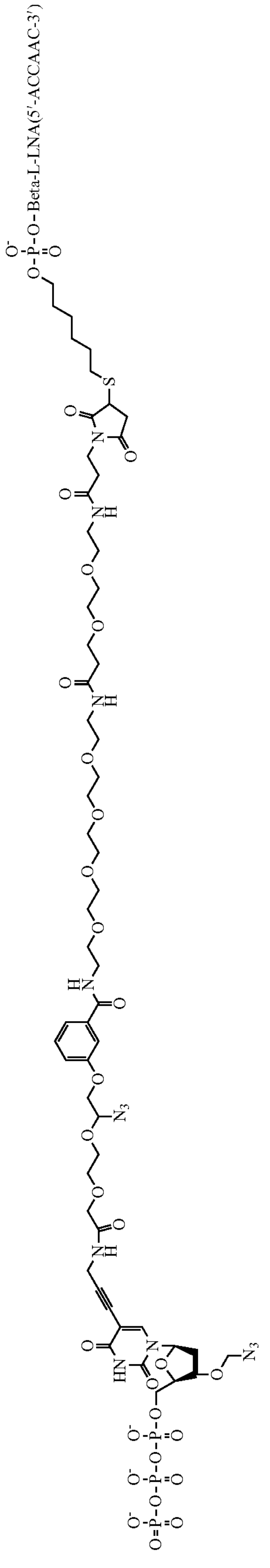
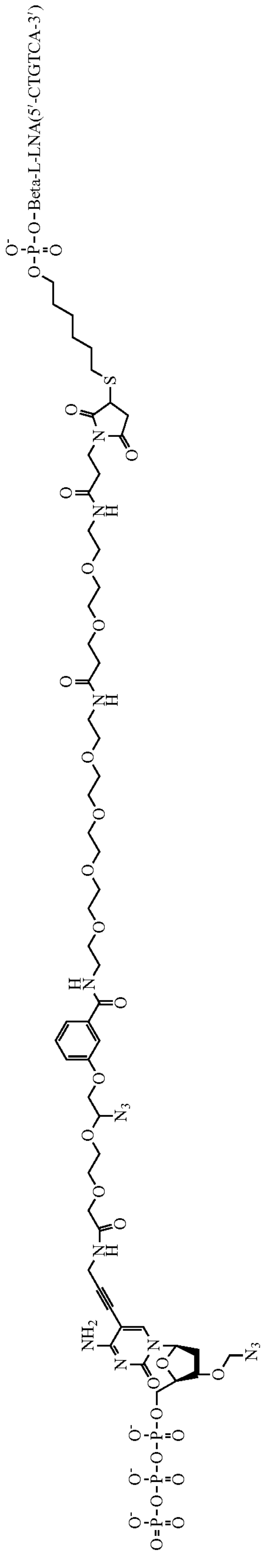
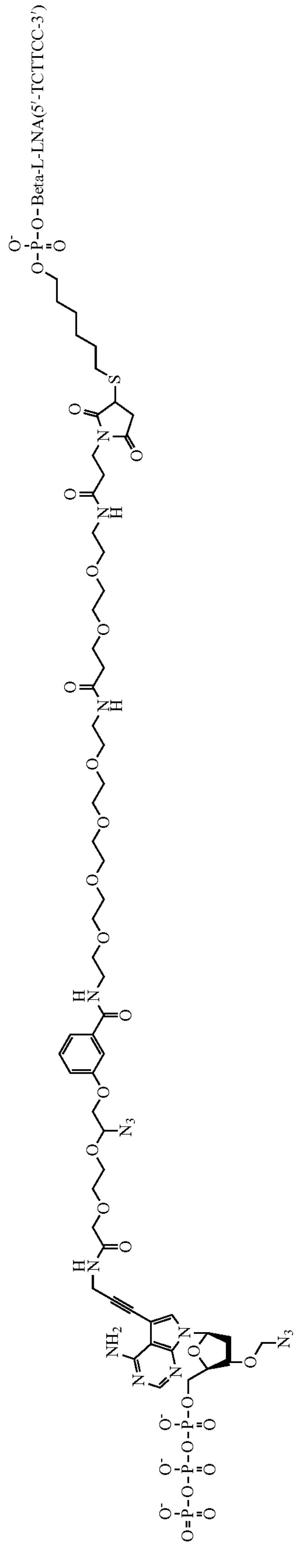

-continued
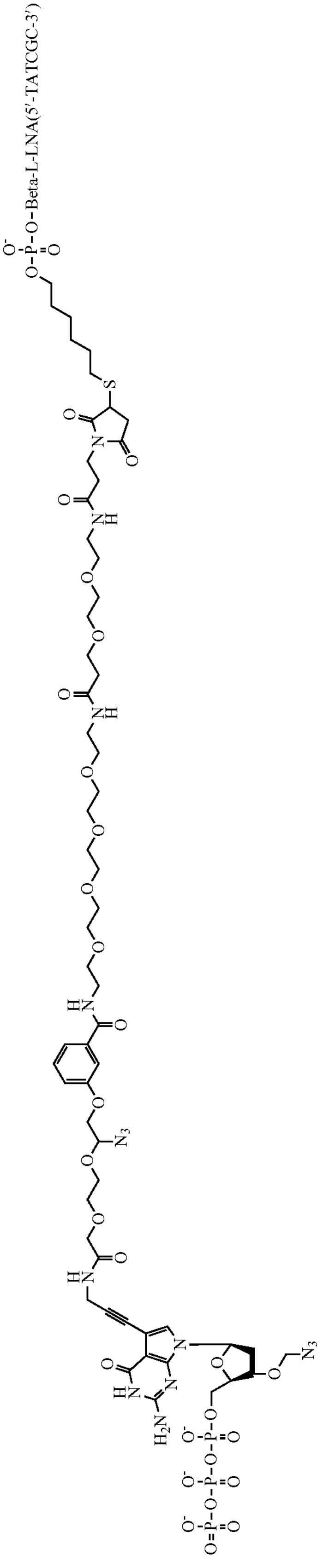
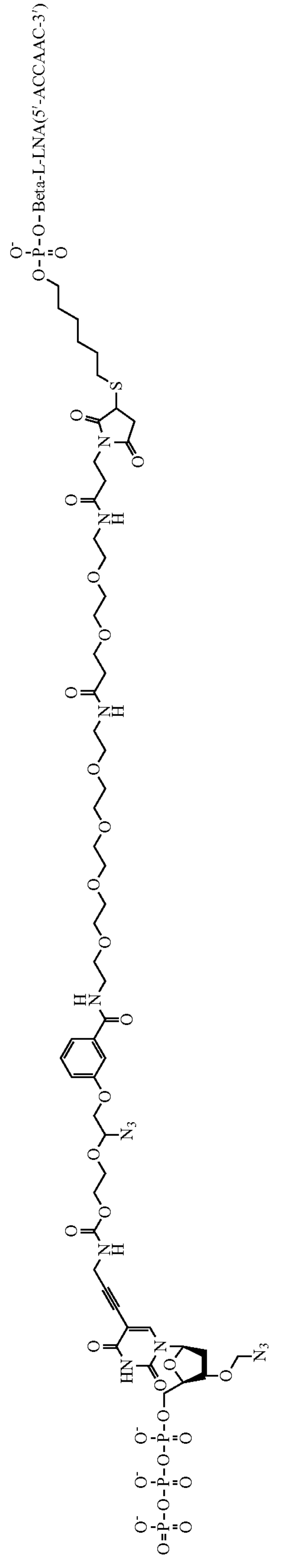
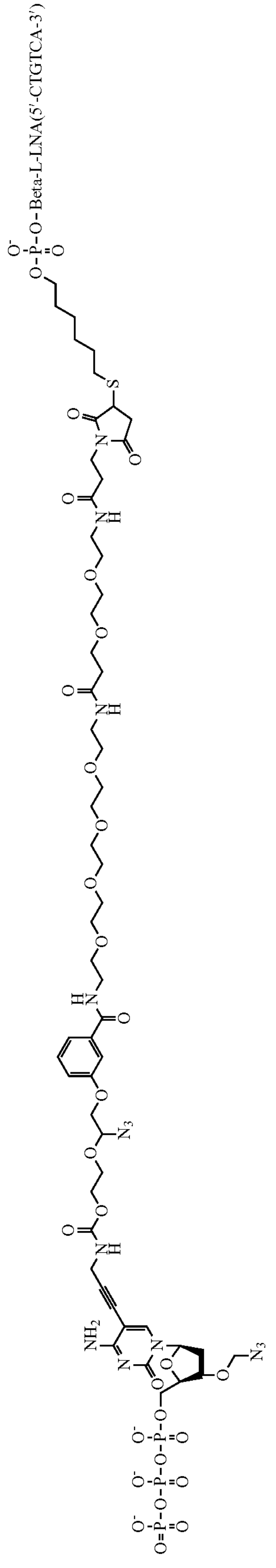

-continued
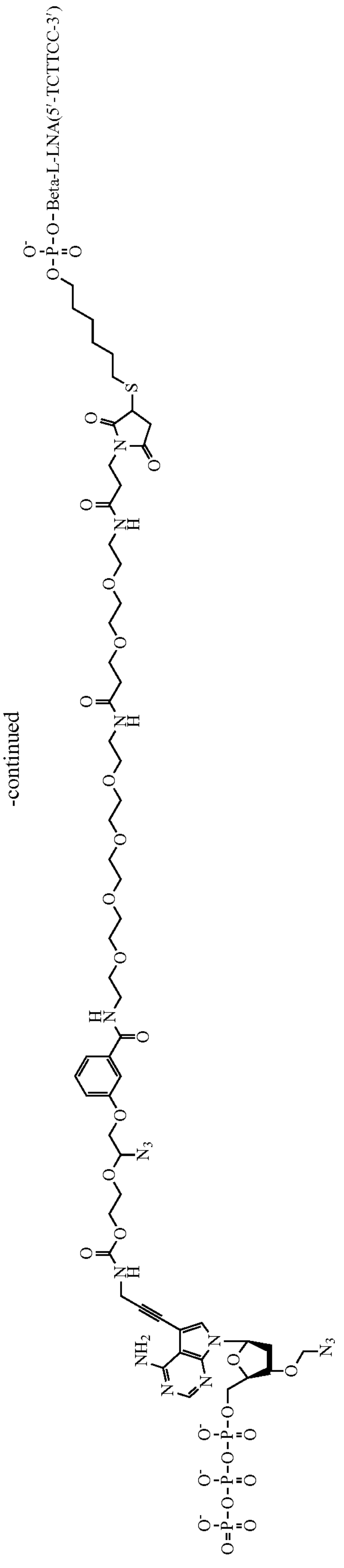
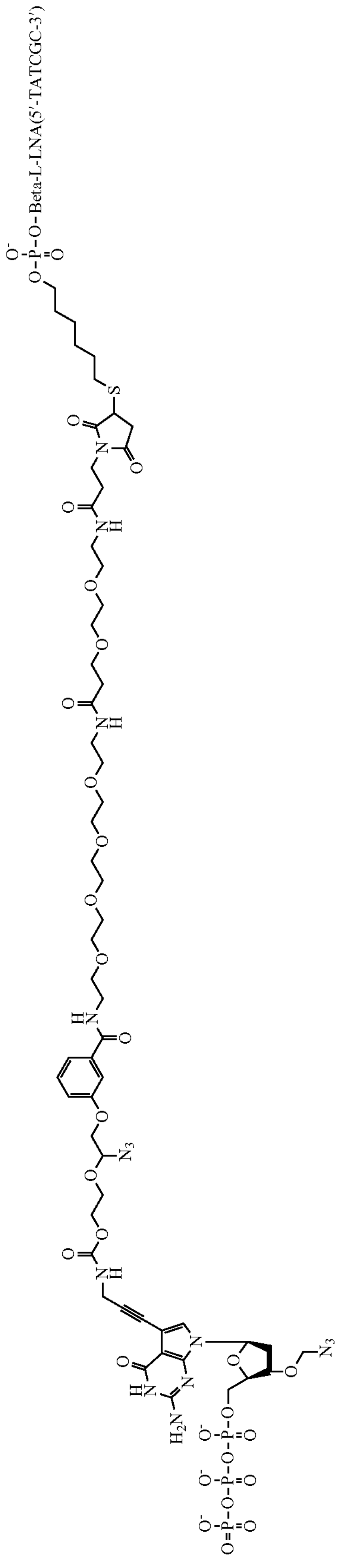
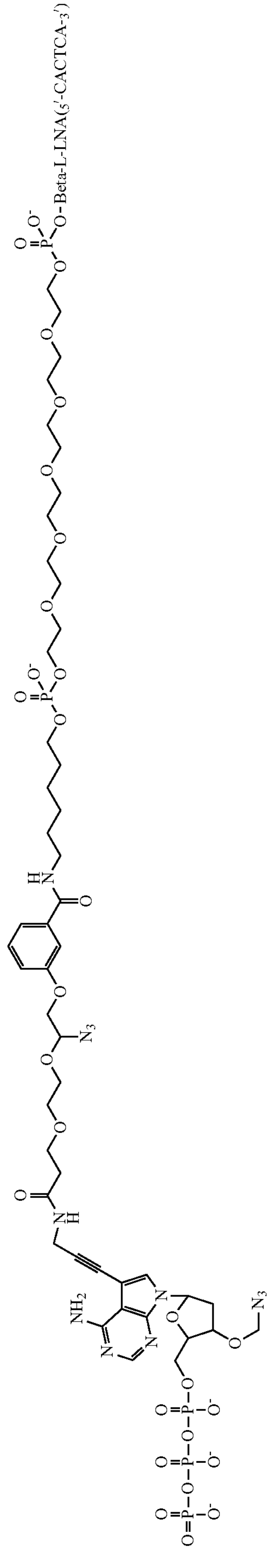

-continued
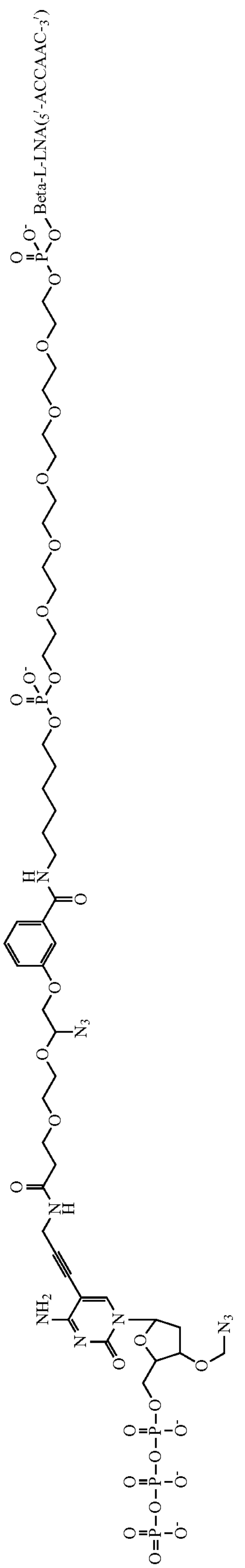
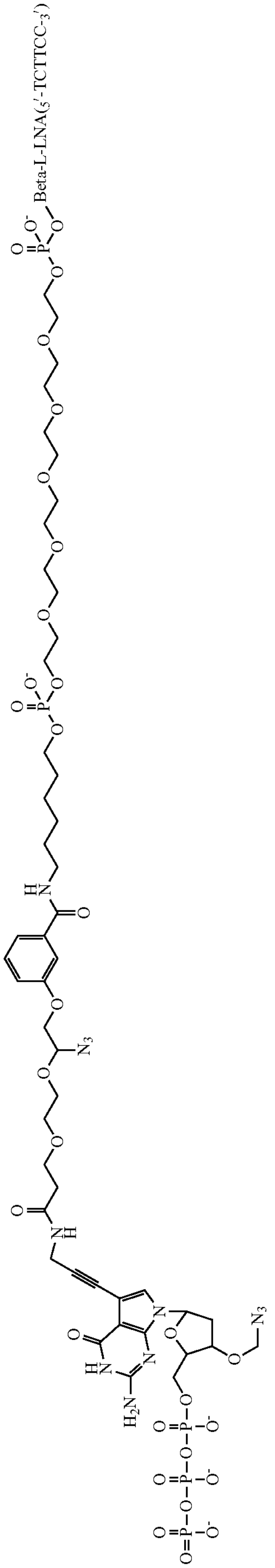
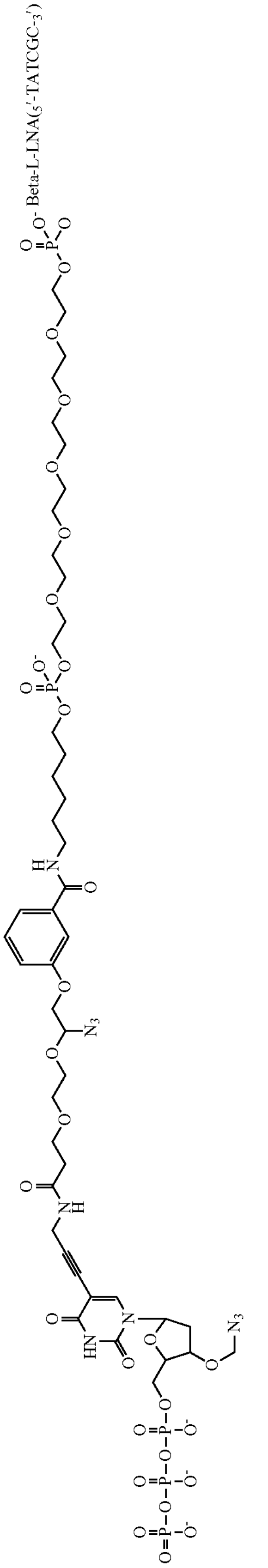

Conjugates

The present disclosure also provides for conjugates capable of reacting with the nucleotides, nucleosides, oligonucleotides, and/or polynucleotides (or any salts thereof) of Formulas (IA) and (IB). In some embodiments, the conjugates have the structure defined by Formulas (IIA) or (IIB):

$$D—L^2—Z^2, \quad \text{or} \tag{IIA}$$

$$D\left[L^2—Z^2\right]_p, \tag{IIB}$$

wherein

- D is a detectable label or a conjugate including a detectable label;
- $L^2$ is a bond or a straight chain or branched, substituted or unsubstituted, saturated or unsaturated, aliphatic or aromatic moiety having between 1 and 60 carbon atoms and optionally including one or more heteroatoms;
- $Z^2$ is a reactive group; and
- p ranges from 2 to about 1000.

In some embodiments, and with reference to Formula (IIA), a detectable label or a conjugate including a detectable label "D" is functionalized with only a single $Z^2$ reactive group, such as through a group $L^2$. In other embodiments, and with reference to Formula (IIB), two or more $Z^2$ reactive groups are conjugated to a single detectable label or a single conjugate including a detectable label "D." In some embodiments, p ranges from 2 to about 500. In other embodiments, p ranges from 2 to about 250. In yet other embodiments, p ranges from 2 to about 150. In further embodiments, p ranges from 2 to about 100. In even further embodiments, p ranges from 2 to about 60. In yet even further embodiments, p ranges from 2 to about 30.

In some embodiments, $Z^2$ is a second member of a pair of reactive groups. For example, $Z^2$ may be second reactive group member which specifically reacts, i.e. reacts orthogonally, with a first reactive group member $Z^1$, such as a first reactive group member $Z^1$ of a nucleotide of any of Formulas (IA) and (IB). In some embodiments, $Z^2$ is selected from any of the reactive groups described herein in relation to the moiety $Z^1$. For example, if $Z^1$ includes a first member of a pair of click conjugates, then $Z^2$ includes a second member of the pair of click conjugates, where the second member of the pair of click conjugates is reactive with the first member of the pair of click conjugates. By way of another example, if $Z^1$ includes a first oligonucleotide, then $Z^2$ includes a second oligonucleotide, where the second oligonucleotide is complementary to the first oligonucleotide and capable of hybridizing with the first oligonucleotide. In yet another example, if $Z^1$ includes a hapten, then $Z^2$ includes an anti-hapten antibody. In a further example, if $Z^1$ includes a host molecule, then $Z^2$ includes a guest molecule capable of interacting with the host molecule. In some embodiments, $Z^2$ is selected from any of the compounds described herein with regard to $Z^1$.

In some embodiments, the moiety $L^2$ includes from between 1 and about 50 carbon atoms. In some embodiments, the moiety $L^2$ includes from between 1 and about 40 carbon atoms. In other embodiments, the moiety $L^2$ includes from between 2 and about 30 carbon atoms. In yet other embodiments, the moiety $L^2$ includes from between about 5 and about 20 carbon atoms. In yet other embodiments, the moiety $L^2$ includes from between about 5 and about 15 carbon atoms. In further embodiments, the moiety $L^2$ includes from between about 10 and about 20 carbon atoms. In some embodiments, the moiety $L^2$ has a molecular weight ranging from about 20 g/mol to about 750 g/mol. In other embodiments, the moiety $L^2$ has a molecular weight ranging from about 20 g/mol to about 500 g/mol. In yet other embodiments, the moiety $L^2$ has a molecular weight ranging from about 20 g/mol to about 250 g/mol.

In some embodiments, the moiety $L^2$ includes biotin (5-[(3aS,4S,6aR)-2-oxo-1,3,3a,4,6,6a-hexahydrothieno[3,4-d]imidazol-4-yl]pentanoic acid) or a derivative thereof. In some embodiments, $L^2$ has the structure: $L^4$-$L^5$- wherein $L^4$ is biotin or a derivative thereof; and wherein $L^5$ is a straight chain or branched, substituted or unsubstituted, saturated or unsaturated, aliphatic or aromatic moiety having between 1 and about 50 carbon atoms and optionally including one or more heteroatoms. In some embodiments, $L^5$ is a straight chain or branched, substituted or unsubstituted, saturated or unsaturated, aliphatic or aromatic moiety having between 1 and about 20 carbon atoms and optionally including one or more heteroatoms. In some embodiments, $L^5$ includes one or more cleavable groups. In some embodiments, $L^2$ is biotin or a derivative thereof. In some embodiments, $L^2$ is derived, at least in part, from biotin. In other embodiments, $L^2$ is a bond.

In some embodiments, the moiety $L^2$ optionally includes one or more cleavable groups, e.g. a photocleavable group, an enzymatically cleavable group, a chemically cleavable group, and a group cleavable at certain pHs. In those embodiments where the moiety $L^2$ includes a cleavable group, the cleavable group can be located at any position within the moiety $L^2$. In those embodiments where the moiety $L^2$ includes a cleavable group, the cleavable group may include any of those described herein with regard to $L^1$ or $X^1$ (e.g. disulfides or alpha-azidoethers). In some embodiments, the moiety $L^2$ includes one cleavable group. In other embodiments, the moiety $L^2$ includes no cleavable groups. In some embodiments, L2 is not present, i.e. $L^2$ is a bond.

In some embodiments, the moiety $L^2$ is a substituted or unsubstituted alkyl group or heteroalkyl group having between 1 and about 40 carbon atoms and which optionally includes one or more cleavable groups. In some embodiments, the moiety $L^2$ is a substituted or unsubstituted alkyl group or heteroalkyl group having between 1 and about 30 carbon atoms and which optionally includes one or more cleavable groups. In some embodiments, the moiety $L^2$ is a substituted or unsubstituted alkyl group or heteroalkyl group having between 1 and about 20 carbon atoms and which optionally includes one or more cleavable groups.

In some embodiments, the moiety $L^2$ has the general structure -$[\text{Linker}]_t$-$[\text{Cleavable Group}]_u$-$[\text{Linker}]_v$-, where each [Linker] may be the same or different, and where t, u, and v are independently 0 or an integer ranging from 1 to about 5. In some embodiments, t, u, and v, are independently 0 or an integer ranging from 1 to about 4. In some embodiments, t, u, and v, are independently 0 or an integer ranging from 1 to about 3. In some embodiments, t, u, and v, are independently 0 or an integer ranging from 1 to 2. In some embodiments, each [Linker] may independently include from 1 to about 30 carbon atoms, and where each [Linker] is optionally substituted with one or more heteroatoms. In some embodiments, each [Linker] may independently include from 2 to about 20 carbon atoms, and where each [Linker] is optionally substituted with one or more heteroatoms. In some embodiments, each [Linker] may independently include from 3 to about 15 carbon atoms, and where each [Linker] is optionally substituted with one or more heteroatoms. In some embodiments, each [Linker] is independently a substituted or unsubstituted alkyl group or heteroalkyl group having between 1 and about 20 carbon atoms. In some embodiments, each [Linker] is independently a substituted or unsubstituted alkyl group or heteroalkyl group having between 1 and about 10 carbon atoms. In some embodiments, the -[Cleavable Linker]- includes a photocleavable group, an enzymatically cleavable group, a chemically cleavable group, and a group cleavable at certain pHs.

In some embodiments, the detectable label or the conjugate including the detectable label "D" may be any chemical group or molecule that is capable of being detected. In some embodiments, the detectable label or the conjugate including the detectable label "D" is a magnetic nanoparticle. In some embodiments, the magnetic nanoparticle is formed from magnetic materials that may be paramagnetic, superparamagnetic or ferromagnetic. In some embodiments, the magnetic nanoparticle is formed from ferromagnetic materials that are crystalline, poly-crystalline, or amorphous in structure. For example, the core of a magnetic nanoparticle may include materials such as, but not limited to, Fe, Co, Ni, $FeOFe_2O_3$, $NiOFe_2O_3$, $CuOFe_2O_3$, $MgOFe_2O_3$, MnBi, MnSb, $MnOFe_2O_3$, $Y_3Fe_5O_{12}$, $CrO_2$, MnAs, SmCo, FePt, or combinations thereof. In other embodiments, the magnetic nanoparticle includes a core material that is a composite or an alloy of a passive metal and a magnetic metal. In some embodiments, passive metals are selected from Au, Ag, Pt or Cu, and magnetic metals are selected from Fe and Co. Nanoparticle cores may also be formed from alloys including Au/Fe, Au/Cu, Au/Gd, Au/Zn, Au/Fe/Cu, Au/Fe/Gd and Au/Fe/Cu/Gd. Other non-limiting magnetic nanoparticles are described in U.S. Patent Publication Nos. 2006/0233712, and 2003/0068187; in PCT Publication Nos. WO/03/073444, WO/02/093140, and WO/02/32404; and in U.S. Pat. Nos. 6,531,304, 6,514,481, 6,254,662, 8,557,607, 9,623,126, and 9,707,2984, the disclosures of which are each hereby incorporated by reference herein in their entireties.

In some embodiments, the magnetic nanoparticles may include those having high magnetic anisotropy. Examples of magnetic nanoparticles having high magnetic anisotropy include, but are not limited to, $Fe_3O_4$, FePt, FePd, and CoPt. To facilitate chemical binding to nucleotides, the particles may be synthesized and coated with $SiO_2$. See, e.g., M. Aslam, L. Fu, S. Li, and V. P. Dravid, "Silica encapsulation and magnetic properties of FePt nanoparticles," Journal of Colloid and Interface Science, Volume 290, Issue 2, 15 Oct. 2005, pp. 444-449. Examples of nanoparticles with high magnetic anisotropy include, but are not limited to, FeO, $Fe_3O_4$, FePt, FePd, and CoPt. To facilitate chemical binding to nucleotides, the particles may be synthesized and coated with $SiO_2$ (see, e.g., M. Aslam, L. Fu, S. Li, and V. P. Dravid, "Silica encapsulation and magnetic properties of FePt nanoparticles," Journal of Colloid and Interface Science, Volume 290, Issue 2, 15 Oct. 2005, pp. 444-449, the disclosure of which is hereby incorporated by reference herein in its entirety).

In some embodiments, the magnetic nanoparticles are coupled directly to one or more $L^2$ groups (e.g. through a covalent linkage). In other embodiments, the magnetic nanoparticles are coupled indirectly to the conjugate. For example, in some embodiments, the magnetic nanoparticles may include a surface functionalized with a plurality of avidin and/or streptavidin molecules. In some embodiments, the magnetic nanoparticles functionalzied with avidin and/or streptavidin molecules may react (e.g. non-covalently) with an $L^2$ group including a biotin molecule or a derivative of a biotin molecule.

In some embodiments, the magnetic nanoparticles coupled (directly or indirectly) to the conjugate may include any magnetic nanoparticle capable of being detected with a magnetic sensor array. In some embodiments, the magnetic nanoparticles coupled (directly or indirectly) to the conjugate may include any magnetic nanoparticle capable of being detected with a magnetic sensor array including a plurality of magnetic sensors (such as configured in a linear array), each of the plurality of magnetic sensors coupled to at least one address line. In some embodiments, a magnetic field is applied to the at least one address line to detect a characteristic of at least one of the plurality of magnetic sensors. In some embodiments, the detected characteristic indicates the presence of a detectable magnetic nanoparticle (such as one coupled to a nucleotide, oligo-/polynucleotide or as part of a nucleotide-conjugate complex, as described further herein). Suitable magnetic sensor arrays for detecting labeled nucleotides and/or formed nucleotide-conjugate complexes (each described herein) including magnetic nanoparticles are described in U.S. Provisional Application No. 62/833,130, the disclosure of which is hereby incorporated by reference herein in its entirety.

In some embodiments, the detectable label "D" is a fluorophore. Fluorophores belong to several common chemical classes including coumarins, fluoresceins (or fluorescein derivatives and analogs), rhodamines, oxazines (including resorufins), BODIPYs, luminophores and cyanines. Additional examples of fluorescent molecules can be found in Molecular Probes Handbook—A Guide to Fluorescent Probes and Labeling Technologies, Molecular Probes, Eugene, OR, ThermoFisher Scientific, 11th Edition. In other embodiments, the fluorophore is selected from xanthene derivatives, cyanine derivatives, squaraine derivatives, naphthalene derivatives, coumarin derivatives, oxadiazole derivatives, anthracene derivatives, pyrene derivatives, oxazine derivatives, acridine derivatives, arylmethine derivatives, and tetrapyrrole derivatives. In some embodiments, dyed of the fluorescein family include, e.g., FAM, HEX, TET, JOE, NAN and ZOE. Dyes of the rhodamine family include, e.g., Texas Red, ROX, R110, R6G, and TAMRA. FAM, HEX, TET, JOE, NAN, ZOE, ROX, R110, R6G, and TAMRA are commercially available from, e.g., Perkin-Elmer, Inc. (Wellesley, Mass., USA), Texas Red is commercially available from, e.g., Life Technologies (Molecular Probes, Inc.) (Grand Island, N.Y.). In some embodiments, dyes of the cyanine family include, e.g., CY2, CY3, CY5, CY5.5 and CY7, and are commercially available from, e.g., GE Healthcare Life Sciences (Piscataway, N.J., USA).

In other embodiments, the fluorescent moiety is selected from a CF dye (available from Biotium), DRAQ and CyTRAK probes (available from BioStatus), BODIPY (available from Invitrogen), Alexa Fluor (available from Invitrogen), DyLight Fluor (e.g. DyLight 649) (available from Thermo Scientific, Pierce), Atto and Tracy (available from Sigma Aldrich), FluoProbes (available from Interchim), Abberior Dyes (available from Abberior), DY and MegaStokes Dyes (available from Dyomics), Sulfo Cy dyes (available from Cyandye), HiLyte Fluor (available from AnaSpec), Seta, SeTau and Square Dyes (available from SETA BioMedicals), Quasar and Cal Fluor dyes (available from Biosearch Technologies), SureLight Dyes (available from APC, RPEPerCP, Phycobilisomes)(Columbia Biosciences), and APC, APCXL, RPE, BPE (available from Phyco-Biotech, Greensea, Prozyme, Flogen).

Yet other types of detectable labels and labeling systems coupled to the conjugates described herein include quantum dots, surface enhanced Raman scattering particles, scattering metallic nanoparticles, FRET systems, intrinsic fluorescence, non-fluorescent chromophores, chemiluminescent labels, bioluminescent labels, radioactive labels, and the like. Such detectable labels are generally known in the art and are further described in U.S. Pat. Nos. 6,399,335, 5,866,366, 7,476,503, and 4,981,977, the disclosures of which are hereby incorporated by reference herein their entireties. Suitable chemiluminescent agents are described in U.S. Pat. Nos. 7,256,299 and 4,363,759, the disclosures of which are hereby incorporated by reference herein in their entireties. Another example of a chemiluminescent agent is an acridinium ester.

In some embodiments, the conjugates have the structure defined by any of Formulas (IIC), (IID), or (IIE):

$$D—(Q^3)_m—(X^2)_n—(Q^4)_o—Z^2, \quad \text{(IIC)}$$

$$D—(Q^3)_m\left[(X^2)—(Q^4)\right]_r Z^2, \text{ or} \quad \text{(IID)}$$

$$D\left[(Q^3)_m\left[(X^2)—(Q^4)\right]_r Z^2\right]_p, \quad \text{(IIE)}$$

wherein

D is a detectable label or a conjugate including a detectable label;

$Q^3$ and $Q^4$ are independently a straight chain or branched, substituted or unsubstituted, saturated or unsaturated, aliphatic or aromatic moiety having between 1 and 30 carbon atoms and optionally substituted with one or more heteroatoms;

$X^2$ is a cleavable group;

$Z^2$ is a reactive group;

n is 0 or an integer ranging from 1 to 3;

m and o are each independently 0 or 1, r is an integer ranging from 1 to 3; and p is an integer ranging from 2 to about 1000.

In some embodiments, and with reference to Formulas (IIC) and (IID), a detectable label or a conjugate including a detectable label "D" is functionalized with only a single $Z^2$ reactive group. In other embodiments, and with reference to Formula (IID), two or more $Z^2$ reactive groups are conjugated to a single detectable label or a single conjugate including a detectable label "D." In some embodiments, p ranges from 2 to about 500. In other embodiments, p ranges from 2 to about 250. In yet other embodiments, p ranges from 2 to about 150. In further embodiments, p ranges from 2 to about 100. In even further embodiments, p ranges from 2 to about 60. In yet even further embodiments, p ranges from 2 to about 30.

In some embodiments, $X^2$ is selected from any of the cleavable groups described herein in relation to the moiety $X^1$. In some embodiments, n is 0. In other embodiments, n is an integer ranging from 1 to 3. In some embodiments, n is 1.

In some embodiments, the moiety $Q^3$ includes biotin (5-[(3aS,4S,6aR)-2-oxo-1,3,3a,4,6,6a-hexahydrothieno[3,4-d]imidazol-4-yl]pentanoic acid) or a derivative thereof. In some embodiments, $Q^3$ is derived from biotin.

In some embodiments, $Q^3$ and $Q^4$ independently comprise a $C_1$-$C_{25}$ straight chain or branched, substituted or unsubstituted alkyl or heteroalkyl group. In other embodiments, $Q^3$ and $Q^4$ independently comprise a $C_1$-$C_{20}$ straight chain or branched, substituted or unsubstituted alkyl or heteroalkyl group. In yet other embodiments, $Q^3$ and $Q^4$ independently comprise a $C_1$-$C_{15}$ straight chain or branched, substituted or unsubstituted alkyl or heteroalkyl group. In yet further embodiments, $Q^3$ and $Q^4$ independently comprise a $C_1$-$C_{10}$ straight chain or branched, substituted or unsubstituted alkyl or heteroalkyl group. In certain embodiments, Q3 and/or Q4 may comprise double or triple bonds.

In yet further embodiments, $Q^3$ and $Q^4$ independently comprise a $C_1$-$C_6$ straight chain or branched, substituted or unsubstituted alkyl or heteroalkyl group. In even further embodiments, $Q^3$ and $Q^4$ independently comprise a $C_1$-$C_6$ straight chain or branched, substituted or unsubstituted alkyl group. In even further embodiments, $Q^3$ and $Q^4$ independently comprise a $C_1$-$C_6$ straight chain or branched alkyl group. In yet further embodiments, $Q^3$ and $Q^4$ independently comprise a $C_1$-$C_4$ straight chain or branched, substituted or unsubstituted alkyl or heteroalkyl group. In even further embodiments, $Q^3$ and $Q^4$ independently comprise a $C_1$-$C_4$ straight chain or branched, substituted or unsubstituted alkyl group. In even further embodiments, $Q^3$ and $Q^4$ independently comprise a $C_1$-$C_4$ straight chain or branched alkyl group.

In some embodiments, $Q^3$ and $Q^4$ independently comprise a polyethylene oxide moiety or a polypropylene oxide moiety. For example, $Q^3$ and $Q^4$ may independently include the group $—[CH_2—CH_2—O]_s—$, where s is an integer ranging from 1 to about 27. In some embodiments, s ranges from 1 to about 12. For example, $Q^3$ and $Q^4$ may independently include the group $—[CH_2—CH(CH_3)—O]_s—$, where s is an integer ranging from 1 to about 27. In some embodiments, s ranges from 1 to 12.

In some embodiments, $Q^3$ and $Q^4$ independently comprise a substituted or unsubstituted $C_5$-$C_7$ aryl group. In other embodiments, $Q^3$ and $Q^4$ independently comprise a substituted or unsubstituted $C_5$-$C_6$ aryl group.

In some embodiments, $Q^3$ and $Q^4$ independently comprise a substituted or unsubstituted $C_5$-$C_7$ cycloalkyl group. In some embodiments, $Q^3$ and $Q^4$ independently comprise a substituted or unsubstituted $C_5$-$C_6$ cycloalkyl group. In some embodiments, $Q^3$ and $Q^4$ independently comprise a substituted or unsubstituted $C_5$-$C_7$ heterocycloalkyl group. In some embodiments, $Q^3$ and $Q^4$ independently comprise a substituted or unsubstituted $C_5$-$C_6$ heterocycloalkyl group.

The skilled artisan will appreciate that the groups D, $Z^2$, $Q^3$, $X^2$, and $Q^4$ are connected via a chemical bond, such as a C—C bond, an amide bond, an ester bond, an urea linkage, an urethane linkage, an amine bond, an ether bond, a thioether bond, a phosphate linkage, a 1, 2, 3-triazole linkage, or a dihydropyridazine linkage. For example, during synthesis D may include a first reactive functional group for coupling (e.g. an amine reactive group, a carboxylic acid reactive group, or a thiol reactive group) to a corresponding reactive functional group of $Q^3$ (e.g. amine reactive group, a carboxylic acid reactive group, or a thiol reactive group). Other suitable reactive functional groups for coupling are described herein (see, e.g., Table 1).

Non-limiting examples of conjugates having any of Formulas (IIA) to (IIE) are set forth below:

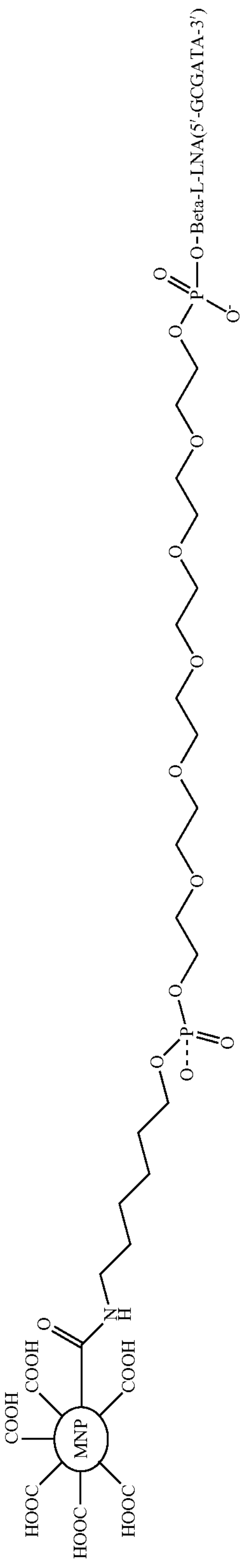
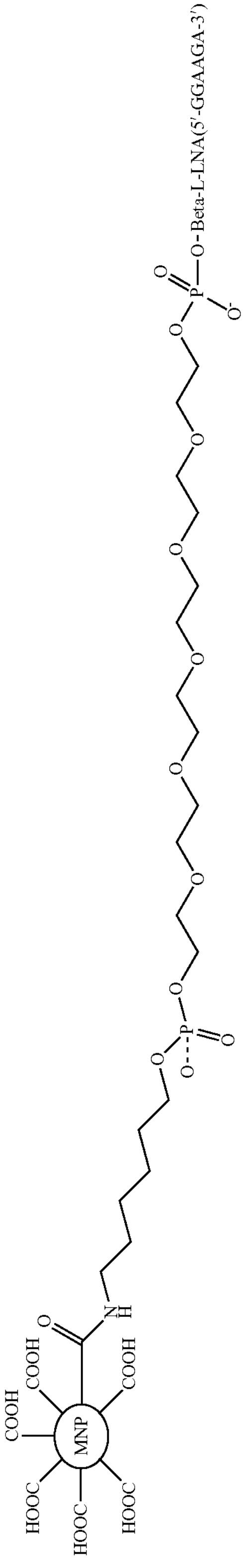
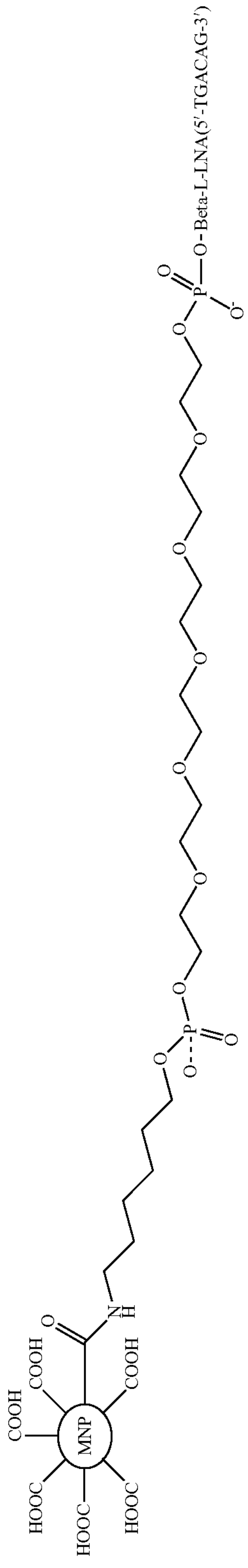
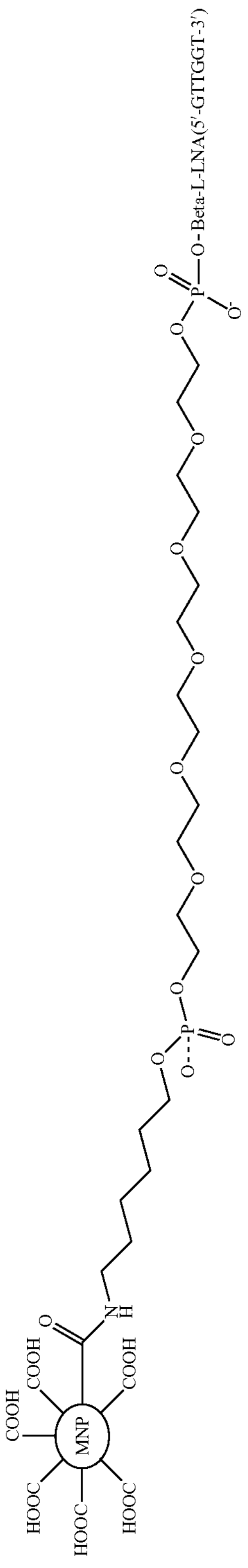

-continued
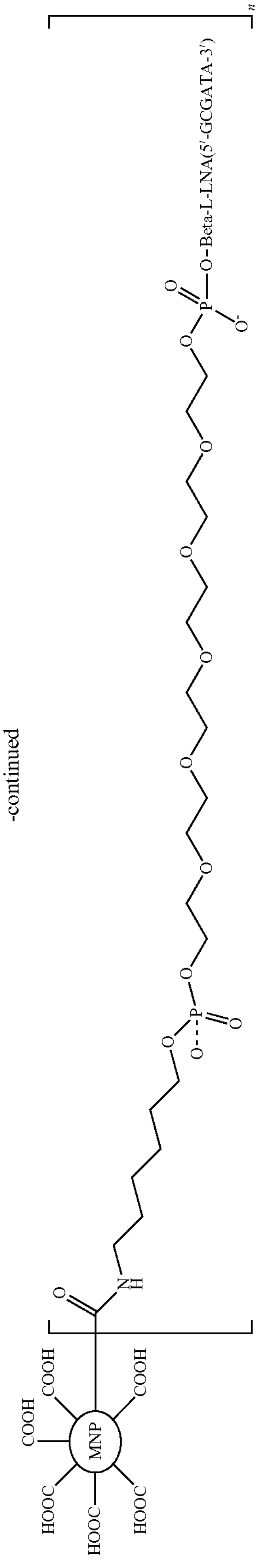
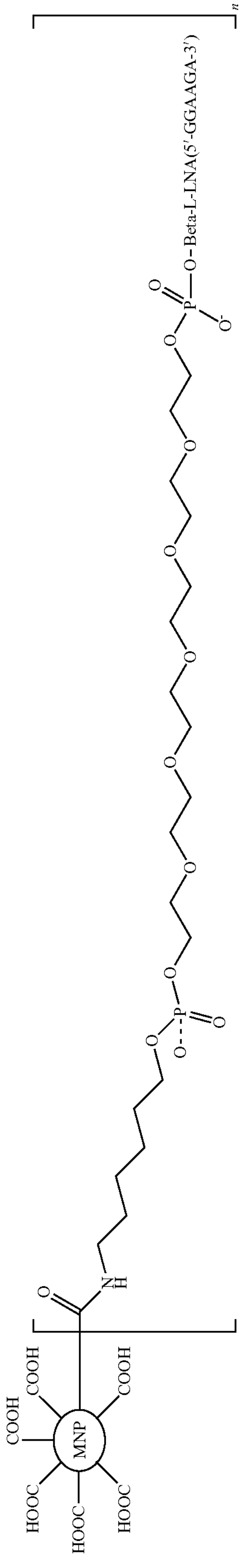
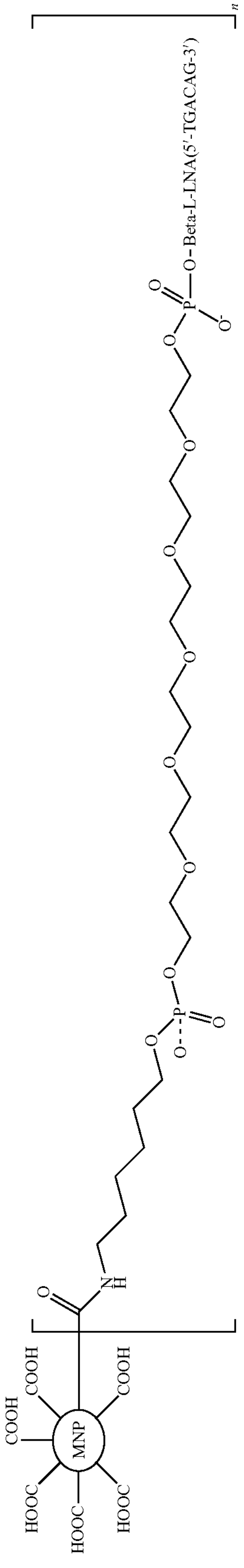
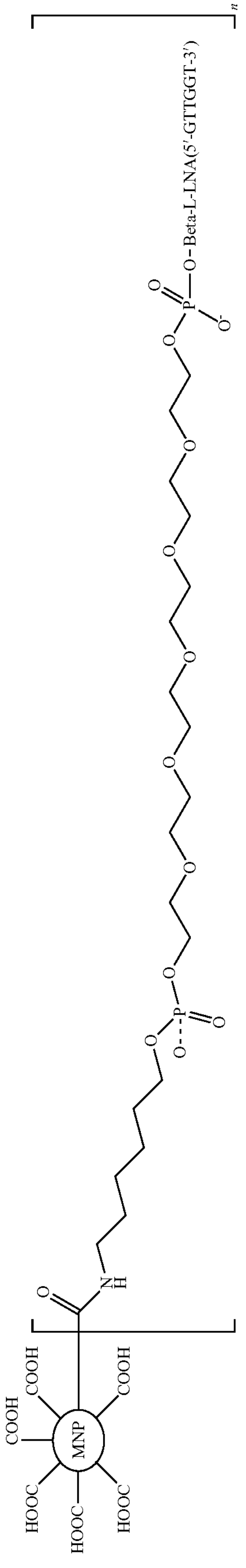

where n ranges from 2 to 1000.

Orthogonal Reactivity Between Nucleotides and Conjugates

Appropriately functionalized nucleotides of Formulas (IA) or (IB) may be orthogonally reacted with corresponding appropriately functionalized conjugates of Formulas (IIA) to (IIE). As noted herein, different nucleotides of Formulas (IA) or (IB) and different conjugates of Formulas (IIA) to (IIE) may each include pairs of reactive groups ($Z^1$ and $Z^2$) that orthogonally react with one another. For example, a first nucleotide of Formula (IA) may include a first reactive group which is a first member of a first pair of reactive groups. Likewise, a first conjugate of Formula (IIA) may include a second reactive group which is a second member of the first pair of reactive groups. When the first nucleotide having the first member of the first pair of reactive groups is brought into contact with the first conjugate having the second member of the first pair of reactive groups, the first and second members of the first pair of reactive groups may orthogonally react with each other and, as described further herein, provide a compound or intermediate, such as one having Formula (III).

The skilled artisan will appreciate that different nucleotides of Formula (IA) may be developed that each include a different $Z^1$ moiety. In this regard, each different nucleotide having a different $Z^1$ moiety may be selectively reacted with an appropriately functionalized conjugate of any one of Formulas (IIA) or (IIB), namely one having a $Z^2$ moiety capable of selectively reacting with the $Z^1$ moiety. For example, a first nucleotide may have a first $Z^1$ moiety $Z^{1A}$ which reacts selectively with a first conjugate having a first $Z^2$ moiety $Z^{2A}$; a second nucleotide may have a second $Z^1$ moiety $Z^{1B}$ which reacts selectively with a second conjugate having a second $Z^2$ moiety $Z^{2B}$; a third nucleotide may have a third $Z^1$ moiety $Z^{1C}$ which reacts selectively with a third conjugate having a third $Z^2$ moiety $Z^{2C}$; and a fourth nucleotide may have a fourth $Z^1$ moiety $Z^{1D}$ which reacts selectively with a fourth conjugate having a fourth $Z^2$ moiety $Z^{2D}$.

Following this example further, each of the first, second, third, and fourth nucleotides (having moieties $Z^{1A}$, $Z^{1B}$, $Z^{1C}$, $Z^{1D}$) may comprise a different nucleobase, e.g. A, G, C, and T. In this manner, four different nucleotides may be provided that each include a different reactive functional group ($Z^{1A}$, $Z^{1B}$, $Z^{1C}$, $Z^{ID}$) and a different nucleobase (A, G, C, and T) as illustrated below:

Nucleotide 1: where the nucleobase (W)=A; and where $Z^1=Z^{1A}$

Nucleotide 2: where the nucleobase (W)=G; and where $Z^1=Z^{1B}$

Nucleotide 3: where the nucleobase (W)=C; and where $Z^1=Z^{1C}$

Nucleotide 4: where the nucleobase (W)=T; and where $Z^1=Z^{1D}$

Each of Nucleotides 1-4 in this example may then be independently and selectively reacted with one of four different conjugates having one of a $Z^{2A}$, $Z^{2B}$, $Z^{2C}$, or $Z^{2D}$ moiety:

Conjugate 1: where $Z^2=Z^{2A}$, where $Z^{2A}$ is a reactive group which reacts with $Z^{1A}$ Conjugate 2: where $Z^2=Z^{2B}$, where $Z^{2B}$ is a reactive group which reacts with $Z^{1B}$ Conjugate 3: where $Z^2=Z^{2C}$, where $Z^{2C}$ is a reactive group which reacts with $Z^{1C}$ Conjugate 4: where $Z^2=Z^{2D}$, where $Z^{2D}$ is a reactive group which reacts with $Z^{ID}$ The orthogonal reactivity between different nucleotides of Formulas (IA) and (IB) and appropriately functional conjugates of Formulas (IIA) and (IIB) will be further described in terms of sequencing herein.

Kits

In some embodiments, the present disclosure provides for a kit including four different nucleotides each having a different nucleobase (A, G, C, or T), and each further having a different $Z^1$ moiety. The present disclosure also provides kits including one or more nucleotides of Formulas (IA) to (IB) and/or one or more conjugates of any of Formulas (IIA) to (IIE).

In some embodiments, a kit may include one nucleotide of Formula (IC), one nucleotide of Formula (ID), one nucleotide of Formula (IE), and one nucleotide of Formula (IF):

(IC)

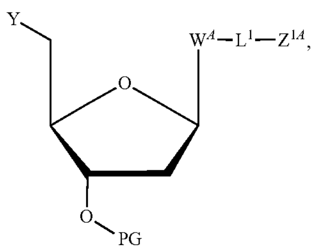

(ID)

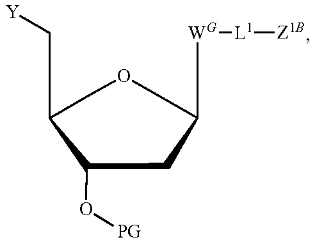

(IE)

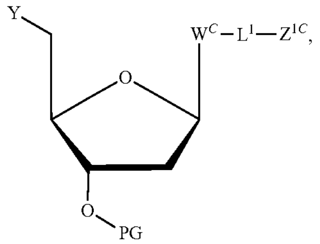

and (IF)

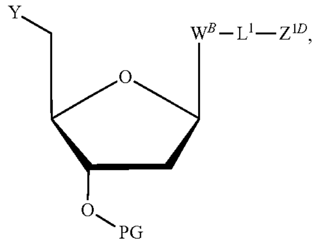

where Y, PG, and $L^1$ are as defined herein; $W^A$ is an adenine nucleobase, $W^G$ is a guanine nucleobase; $W^C$ is a cytosine nucleobase; and $W^R$ is a thymine nucleobase or an uracil nucleobase; and wherein $Z^{1A}$, $Z^{1B}$, $Z^{1C}$ and $Z^{1D}$ each comprise a different reactive group (including any of those reactive groups defined herein). In some embodiments, each of the nucleotides of Formulas (IC), (ID), (IE), and (IF) may be provided in admixture in a single container or dispenser. In some embodiments, each of the nucleotides of Formulas (IC), (ID), (IE), and (IF) may be provided in separate containers or in separate dispensers.

In some embodiments, the kit may further include three or four different conjugates of any of Formulas (IIA) to (IIE), wherein each of the different conjugates includes a moiety $Z^2$ which reacts orthogonally with one of the moieties $Z^{1A}$, $Z^{1B}$, $Z^{1C}$, and $Z^{1D}$. For example, the kit may further include at least three of the conjugates of Formulas (IIF), (IIG), (IIH), and (III):

$$D—L^2—Z^{2A}, \quad (IIF)$$

$$D—L^2—Z^{2B}, \quad (IIG)$$

$$D—L^2—Z^{2C}, \quad (IIH)$$

and $$D—L^2—Z^{2D}, \quad (III)$$

where D and $L^2$ are as defined herein, and wherein $Z^{2A}$, $Z^{2B}$, $Z^{2C}$, and $Z^{2D}$ each comprise a different reactive group, and where $Z^{2A}$ reacts selectively with $Z^{1A}$, $Z^{2B}$ reacts selectively with $Z^{1B}$, $Z^{2C}$ reacts selectively with $Z^{1C}$, and $Z^{2D}$ reacts selectively with $Z^{ID}$. In some embodiments, each of the different conjugates of Formula (IIA) are provided in a separate container or dispenser. In some embodiments, each of the different conjugates in the kit have the same label. In other embodiments, each of the different conjugates in the kit have a different label. Likewise, in some embodiments, each of the different conjugates includes the same $L^2$ moiety. In other embodiments, each of the different conjugates includes a different $L^2$ moiety. In those embodiments where "D" is a magnetic nanoparticle, $L^2$-$Z^{2A}$, $L^2$-$Z^{2B}$, $L^2$-$Z^{2C}$, $L^2$-$Z^{2D}$ may be present more than once, as in any one of Formulas (IIB), (IID), and (IIE).

Nucleotide-Conjugate Complexes

The nucleotides, nucleosides, oligonucleotides, and/or polynucleotides (or salts thereof) of Formulas (IA) or (IB) may be reacted with a suitable conjugate of any of Formulas (IIA) to (IIE) to provide a nucleotide-conjugate complex. In some embodiments, the nucleotide-conjugate complexes are incorporated within a nascent nucleic acid strand, such as described further herein. For example, and as described further herein, a nucleotide-conjugate complex may be formed when a conjugate of Formula (IIA) reacts with a nucleotide of Formula (IA), such as a nucleotide for Formula (IA) incorporated into a nascent nucleic acid stand. In general, the formed nucleotide-conjugate complexes have the structure of Formula (III):

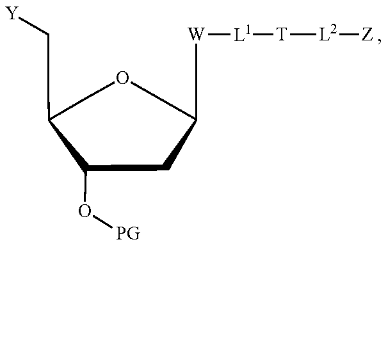

(III)

where each of Y, PG, W, $L^1$, $L^2$, and D are as defined herein, and where T represents the product of the "reaction" between reactive groups $Z^1$ (see Formula (IA) and $Z^2$ (see Formula (IB)). The skilled artisan will appreciate that the groups W, $L^1$, T, $L^2$, and D may be coupled to each other via a chemical bond, such as a C—C bond, an amide bond, an ester bond, an urea linkage, an urethane linkage, an amine bond, an ether bond, a thioether bond, a phosphate linkage, a 1, 2, 3-triazole linkage, or a dihydropyridazine linkage. Other types of chemical bonds suitable for coupling the various moieties are described further herein.

In some embodiments, the nucleotide-conjugate complexes include at least one cleavable group (which may be either within the moiety $L^1$ or $L^2$). In other embodiments, the nucleotide-conjugate complexes include at least two cleavable groups (e.g. one cleavable group within $L^1$ and another cleavable group within $L^2$).

In some embodiments, the product of the "reaction" between the reactive groups comprises a new moiety or represents an interaction (e.g. hydrogen bonding, van der Waals interactions, hybridization) between two molecules. For example, T may represent the product of the covalent coupling of two reactive functional groups (e.g. the reaction of two different functional groups capable of participating in a "click chemistry" reaction); the hydrogen bonding and/or van der Waals interactions between host/guest molecules (e.g. the interaction between cucurbit[7]uril and aminoadamantane); the hybridization of two complementary oligonucleotides (e.g. the hybridization between a first oligonucleotide and a second oligonucleotide which is complementary to the first oligonucleotide; or between a first oligonucleotide including at least one LNA monomer and a second oligonucleotide including at least one LNA monomer which is complementary to the first oligonucleotide); and/or the interaction between two specific binding entities (e.g. between a hapten and an anti-hapten antibody).

In some embodiments, the nucleotide-conjugate complexes of Formula (III) are intermediates produced during sequencing by synthesis as illustrated in Scheme 1 (and again, the nucleotide-conjugate complexes are incorporated within a nascent nucleic acid). In general, sequencing by synthesis techniques (described further herein) involve the enzymatic extension of a nascent nucleic acid strand through the sequential addition of nucleotides against a template strand. In this regard, Scheme 1 illustrates the extension of a single nascent nucleic acid strand, such as a nascent nucleic acid strand hybridized to a nucleic acid template to be sequenced. Here, the nascent nucleic acid is extended through the sequential introduction and incorporation of nucleotides, such as those of Formula (IA). Additionally, Scheme 1 illustrates the formation of two different detectable nucleotide-conjugate complexes of Formula (III) through the introduction of appropriately functionalized conjugates having any one of Formulas (IIA) to (IIE).

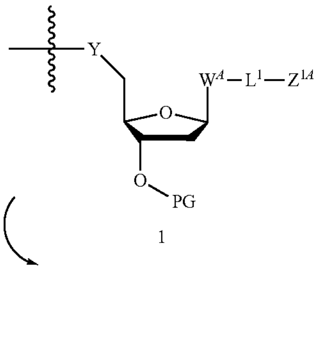

10

1

-continued

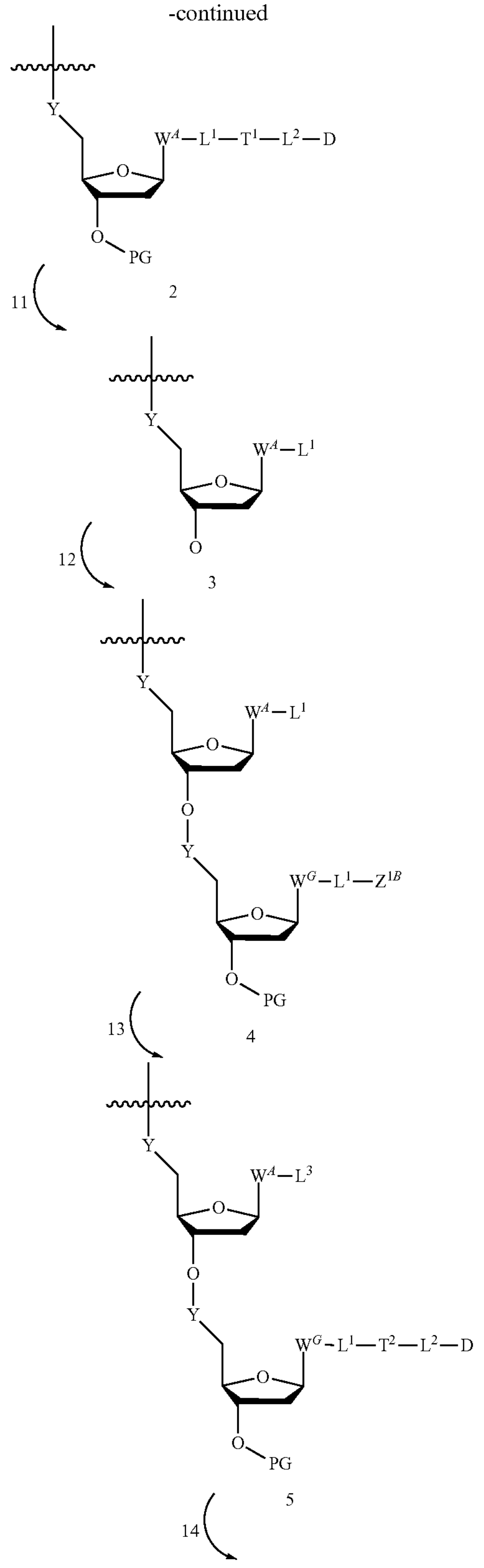

More specifically, Scheme 1 illustrates nucleotide 1 (a first nucleotide of Formula (IA) having a first nucleobase "$W^A$") coupled to a nascent nucleic acid strand, where nucleotide 1 includes a protecting group ("PG") to prevent further extension of the nascent nucleic acid strand. At step 10, a first conjugate of any one of Formulas (IIA) to (IIE) may be introduced which is reactive only with incorporated nucleotide 1. For example, nucleotide 1 may include a $Z^{1A}$ moiety which is reactive only with a $Z^{2A}$ moiety of the first introduced conjugate of any one of Formulas (IIA) to (IIE). The reaction between nucleotide 1 and the conjugate of any one of Formulas (IIA) to (IIE) provides for a first nucleotide-conjugate complex 2 which includes a detectable label "D." After the first nucleotide-conjugate complex 2 is formed and detected, both the detectable label "D" and the protective group "PG" may be removed (step 11) to yield the incorporated nucleotide 3.

By way of example, cysteamine may be used to chemically cleave a cleavable group including a nitrate group. Likewise, a 3'-O-allyl group may be deallylated using a Pd-catalyzed deallylation mixture. By way of another example, in some embodiments, the sample is irradiated with visible, ultraviolet, or infrared radiation to photochemically cleave the cleavable groups $L^1$ and/or $L^2$. Once the cleavable group is cleaved, a group $L^3$ remains, which is a fragment of the group $L^1$. In some embodiments, the protecting group is removed from the incorporated nucleotide either prior to, after, or simultaneously with the cleaving of the detectable label (step 11). TCEP (tris(2-carboxyethyl) phosphine) may be used to chemically cleave an azidomethyl protecting group and alpha-azidoether linkage in $L^1$ and/or $L^2$.

Following the cleavage of the protecting group "PG," another nucleotide 4 (a second nucleotide of Formula (IA) having a second nucleobase "$W^G$") may be incorporated into the nascent nucleic acid strand (step 12). In some embodiments, nucleobase 4 includes a protecting group ("PG") to prevent further extension of the nascent nucleic acid strand. At step 13, a second conjugate of any one of Formulas (IIA) to (IIE) may be introduced which is reactive only with incorporated nucleotide 4. For example, nucleotide 4 may include a $Z^{1B}$ moiety which is reactive only with a $Z^{2B}$ moiety of the second introduced conjugate of any one of Formulas (IIA) to (IIE). The reaction between nucleotide 4 and the conjugate of any one of Formulas (IIA) to (IIE) provides for second nucleotide-conjugate complex 5 which includes a detectable label "D." The steps of the incorporation of a nucleotide of Formula (IA), the formation of a nucleotide-conjugate complex of Formula (III) (such as one corresponding to an incorporated nucleotide), and the detection of the formed nucleotide-conjugate complex of Formula (III) may be repeated (step 14).

Sequencing by Synthesis

As noted above, sequencing by synthesis techniques involve the enzymatic extension of a nascent nucleic acid copy strand through the sequential addition of nucleotides against a template strand molecule to be sequenced. In some embodiments, sequencing by synthesis utilizes nucleotides including a reversible terminator (e.g. the protecting group of the nucleotides of Formula (IA)) so that only a single base may be added by an enzyme (e.g. a polymerase) to each nascent nucleic acid copy strand. In some embodiments, the sequencing reaction is conducted simultaneously on a very large number (e.g. millions) of different template nucleic acid molecules spread out on a solid surface. In some embodiments, the nucleic acid template strand to be sequenced may be composed of DNA, RNA or analogs thereof. In some embodiments, the source of the template nucleic acids can be genomic DNA, messenger RNA, or other nucleic acids from native sources. In some embodiments, the template nucleic acids that are derived from such sources may be amplified prior to use. Other aspects of sequencing by synthesis including methods of sequencing and materials used during the sequencing process are described, for example, in PCT Application Publication Nos. WO 91/06678, WO/2005/024010, WO/2006/120433, WO/2005/065814, and WO/2006/064199; in U.S. Pat. Nos. 9,605,310 and 9,441,272; and in United States Publication Nos. 2019/0024162, the disclosures of which are hereby incorporated by reference herein in their entireties.

While Scheme 1 above illustrates the formation of nucleotide-conjugate complexes of Formula (III), the Scheme is illustrative of the chemistry occurring along a single nascent strand and hence the sequencing of only a single target polynucleotide. The skilled artisan will appreciate, however, that the sequences of multiple (e.g. millions) different target (or even the same amplified target) polynucleotides may be determined simultaneously. In some embodiments, there may be a clonal amplification within each of a plurality of sensors (e.g. bridged amplification). In these embodiments, there may be multiple identical nucleic acid strands on a single sensor or on multiple sensors.

The present disclosure provides a method of sequencing by synthesis where the sequential formation of different subsets of nucleotide-conjugate complexes are detected. In these embodiments, the detection of the different sequentially formed subsets of nucleotide-conjugate complexes enables the sequential determination of the different nucleotides incorporated into the complements of each of a plurality of target polynucleotide molecules during each cycle of nucleotide incorporation. The presently described methods therefore enable massively parallel sequencing as nucleotide-conjugate complexes are sequentially formed and detected during each iterative extension.

The present disclosure provides a method for sequencing target polynucleotide molecules. In some embodiments, the present disclosure provides a method of sequencing by synthesis where different subsets of nucleotide-conjugate complexes (such as those of Formula (III)) are sequentially formed and detected during each iterative extension of a plurality of nascent nucleic acid copy strands, where each nascent nucleic acid copy strand is complementary to one of a plurality of target polynucleotide molecules. In some embodiments, the plurality of target polynucleotide molecules are arrayed on a solid support. In some embodiments, the solid support is a flow cell. In some embodiments, the nucleotide-conjugate complexes are incorporated within a nascent nucleic acid strand, such as described further herein.

In some embodiments, the method first comprises extending each nascent nucleic acid copy strand by incorporating one of four different nucleotides into each of the nascent nucleic acid copy strands. In some embodiments, each of the four different nucleotides comprises (i) a protective group, and (ii) a reactive group coupled to a nucleobase through a cleavable linker, and where each different nucleotide of the four different nucleotides comprises a different nucleobase and a different reactive group. The skilled artisan will appreciate that the different nascent nucleic acid strands may each independently be extended with a different nucleotide depending on the sequence of the corresponding complementary target polynucleotide molecule.

In some embodiments, the nucleotides are incorporated into the nascent nucleic acid copy strands by introducing a pool of four different nucleotides of Formulas (IA) or (IB), where each of the four different nucleotides includes a different nucleobase (e.g. A, G, C, T/U) and a different $Z^1$ moiety. In other embodiments, the nucleotides are incorporated by introducing a pool of four different nucleotides, wherein a first nucleotide has the Formula (IC), a second nucleotide has Formula (ID), a third nucleotide has Formula (IE), and a fourth nucleotide has Formula (IF), provided that the reactive groups $Z^{1A}$, $Z^{1B}$, $Z^{1C}$, and $Z^{1D}$ are each different.

Next, different subsets of nucleotide-conjugate complexes are sequentially formed (e.g. formed within a nascent nucleic acid). In some embodiments, each formed nucleotide-conjugate complex within any single subset of nucleotide-conjugate complexes is derived from only one of the different nucleotides incorporated into the nascent nucleic acid copy strands. In some embodiments, the different subsets of nucleotide-conjugate complexes are sequentially formed by sequentially introducing a different conjugate including a detectable label, where each of the different conjugates introduced are orthogonally reactive with only one of the nucleotides incorporated within the nascent nucleic acid copy strands. For example, at least three different conjugates of any of Formulas (IIA) to (IIE) may be sequentially introduced, where each different conjugate of the at least three different conjugates of any of Formulas (IIA) to (IIE) react orthogonally with only one of the four incorporated nucleotides of Formulas (IA) or (IB). Given the sequential addition of the different conjugates of any of Formulas (IIA) to (IIE) and their orthogonal reactivity with the different incorporated nucleotides of Formulas (IA) or (IB), the sequential formation and detection of the different subsets of nucleotide-conjugate complexes facilitates the identification of the different nucleotides incorporated into the nascent nucleic acid copy strands. As a result, the sequences of each corresponding complementary target polynucleotide molecule may be determined. The skilled artisan will appreciate that the above process may be repeated for one or more cycles, i.e. one or more extensions of the nascent nucleic acid copy strands.

Figure 1B:
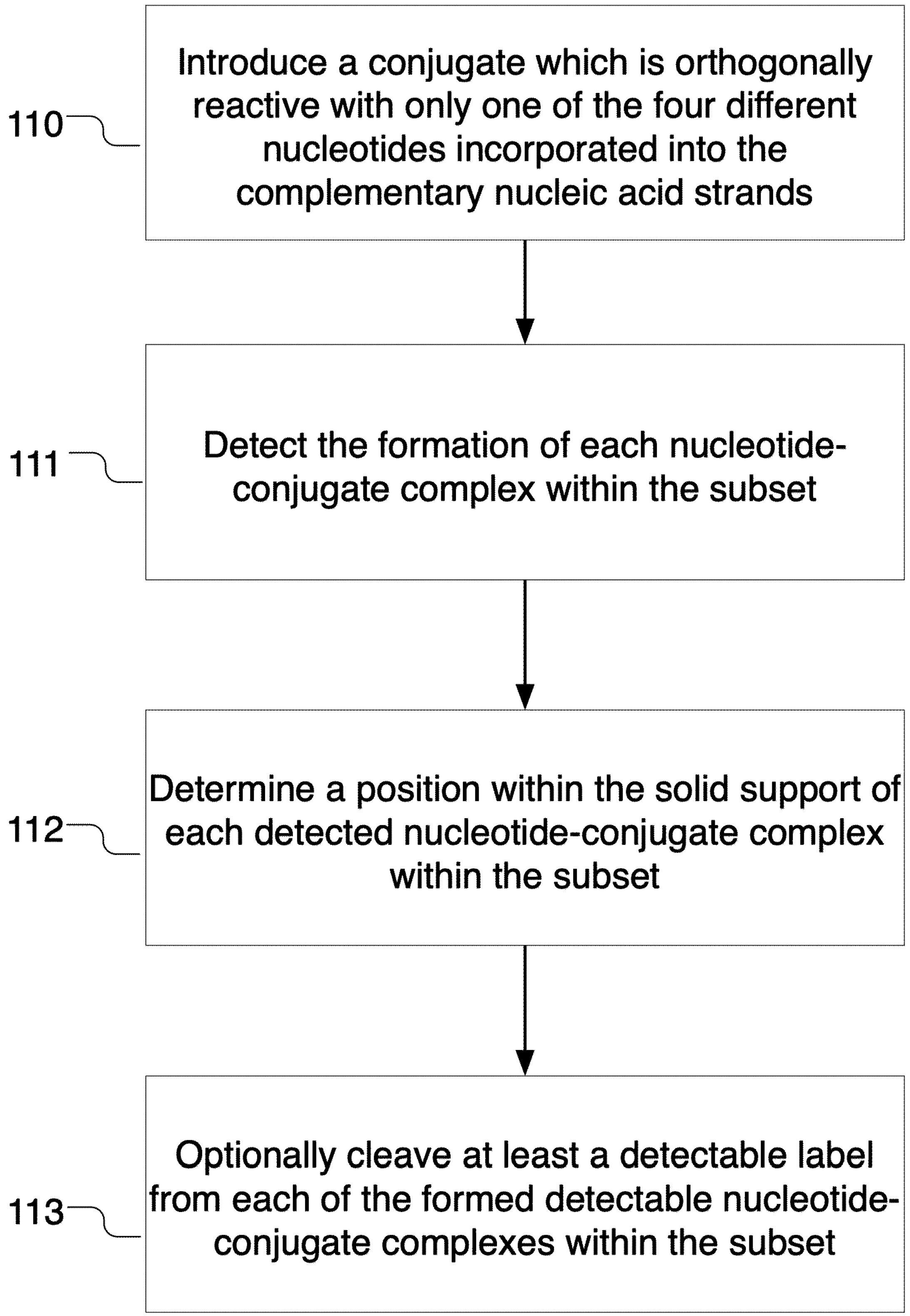
FIG. 1B provides a flowchart illustrating a method of sequentially forming different subsets of nucleotide-conjugate complexes in accordance with one embodiment of the present disclosure.

FIGS. 1A and 1B illustrate a method of sequencing a nucleic acid library including a plurality of target polynucleotide molecules. In some embodiments, sequencing by synthesis may be carried out with the plurality of different target polynucleotides arrayed on a solid support. For example, a plurality of target polynucleotides may be immobilized on the solid support through linker molecules or may be attached to particles which may be attached to the solid support. In some embodiments, sequencing by synthesis may utilize a flow cell loaded with a library of a plurality of different target polynucleotide molecules for sequencing. For example, a flow cell may include millions of target polynucleotide molecules for sequencing. In some embodiments, a nucleic acid sequencing library may be prepared by fragmenting a gDNA sample and ligating adapters to the ends of the generated fragments. The library may then be loaded into a flow cell and the fragments may be hybridized to the flow cell surface. In some embodiments, each bound fragment may be amplified into a clonal cluster through bridge amplification. Solid supports, flow cells, and the preparation of sequencing libraries are further disclosed in U.S. Publication No. 2010/00111768; and in PCT Publication Nos. WO/2019/126040, WO/2018/119053, and WO/2018/119101, the disclosures of which are incorporated by reference herein in their entireties.

After the nucleic acid library is prepared and arrayed onto a solid support, one of four different nucleotides are incorporated into each complementary nascent nucleic acid copy strand present on the solid support (step 101), wherein each of the four different nucleotides includes (i) a 3-hydroxyl protecting group, and (ii) a reactive group coupled to a nucleobase through a cleavable linker, and where each different nucleotide of the four different nucleotides includes a different nucleobase and a different reactive group. In some embodiments, the nucleotides are incorporated by introducing a pool of four different nucleotides of Formula (IA) to the flow cell, where each of the four different nucleotides includes a different nucleobase (e.g. A, G, C, T/U) and a different $Z^1$ moiety. In some embodiments, a first of the four different nucleotides has the structure of Formula (IC); a second of the four different nucleotides has the structure of Formula (ID); a third of the four different nucleotides has the structure of Formula (IE); and a fourth of the four different nucleotides has the structure of Formula (IF), provided that the reactive groups $Z^{1A}$, $Z^{1B}$, $Z^{1C}$, and $Z^{1D}$ are each different. In some embodiments, each of the reactive groups $Z^{1A}$, $Z^{1B}$, $Z^{1C}$, and $Z^{1D}$ may comprise a different oligonucleotide sequence.

After each nascent nucleic acid copy strand is extended with one of the four different nucleotides (step 101), different subsets of nucleotide-conjugate complexes are sequentially formed (step 102), where each nucleotide-conjugate complex within each different subset of sequentially formed nucleotide-conjugate complexes is derived from only one of the different nucleotides incorporated into the nascent nucleic acid copy strands (e.g. the nucleotide-conjugate complexes are incorporated within the nascent nucleic acids). In some embodiments, the step of sequentially forming different subsets of nucleotide-conjugate complexes is performed three times. In other embodiments, the step of sequentially forming different subsets of nucleotide-conjugate complexes is performed four times.

In some embodiments, the sequential formation (step 102) of different subsets of nucleotide-conjugate complexes comprises: introducing a conjugate including a detectable label and which is orthogonally reactive with only one of the four different nucleotides incorporated into the complementary nascent nucleic acid copy strands (step 110); detecting the formation of each nucleotide-conjugate complex within the subset by detecting the label of each introduced conjugate (step 111); determining a position within the solid support of each detected nucleotide-conjugate complex within the subset (step 112); and optionally cleaving at least a detectable label from each of the formed detectable nucleotide-conjugate complexes within the subset (step 113). In some embodiments, each introduced conjugate includes a reactive group including an oligonucleotide sequence which is complementary to an oligonucleotide sequence coupled to one of the incorporated nucleotides.

The skilled artisan will appreciate that the above process is for a single extension of the nascent nucleic acid copy strands complementary to the plurality of target polynucleotide molecules on the solid support. This process may then be repeated for each iterative extension of the nascent nucleic acid copy strands complementary to the plurality of target polynucleotide molecules on the solid support. Before the complementary nascent nucleic acid copy strand may be further extended (i.e. before another cycle may be performed), the 3-hydroxyl protecting groups must be cleaved (step 103) from the four different nucleotides incorporated at step 101. Additionally, if any detectable labels have not yet been cleaved, the detectable labels must be cleaved prior to the next extension. In some embodiments, the detectable labels and 3-hydroxyl protecting groups are cleaved at the same time and using the same reagent. In some embodiments, the sequential formation and detection of the different subsets of nucleotide-conjugate complexes facilitates determination of each nucleotide incorporated into each nascent nucleic acid strand during each iterative extension.

Figure 2A:
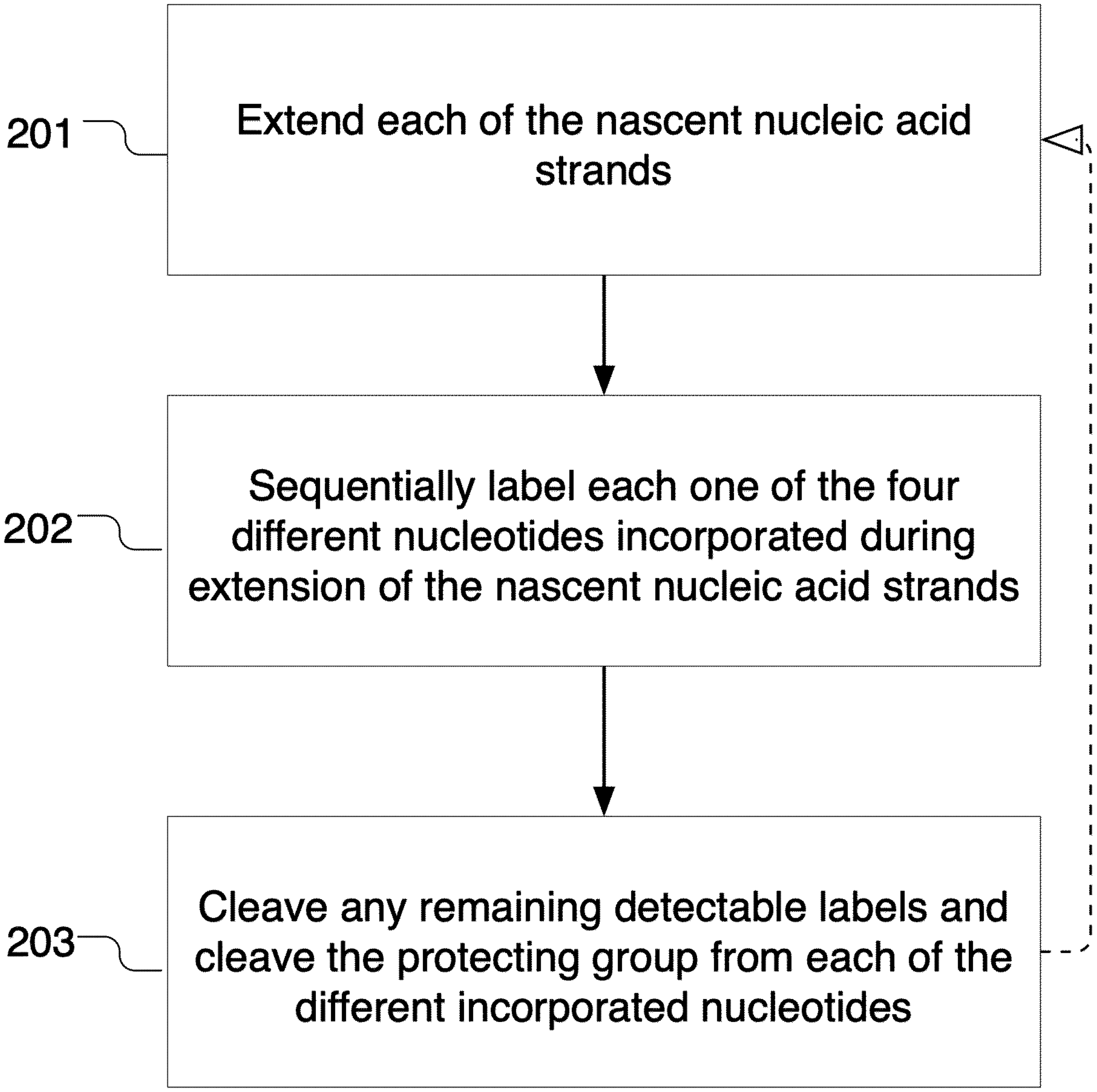
FIG. 2A provides a flowchart setting forth a method of sequencing in accordance with one embodiment of the present disclosure.
Figure 2B:
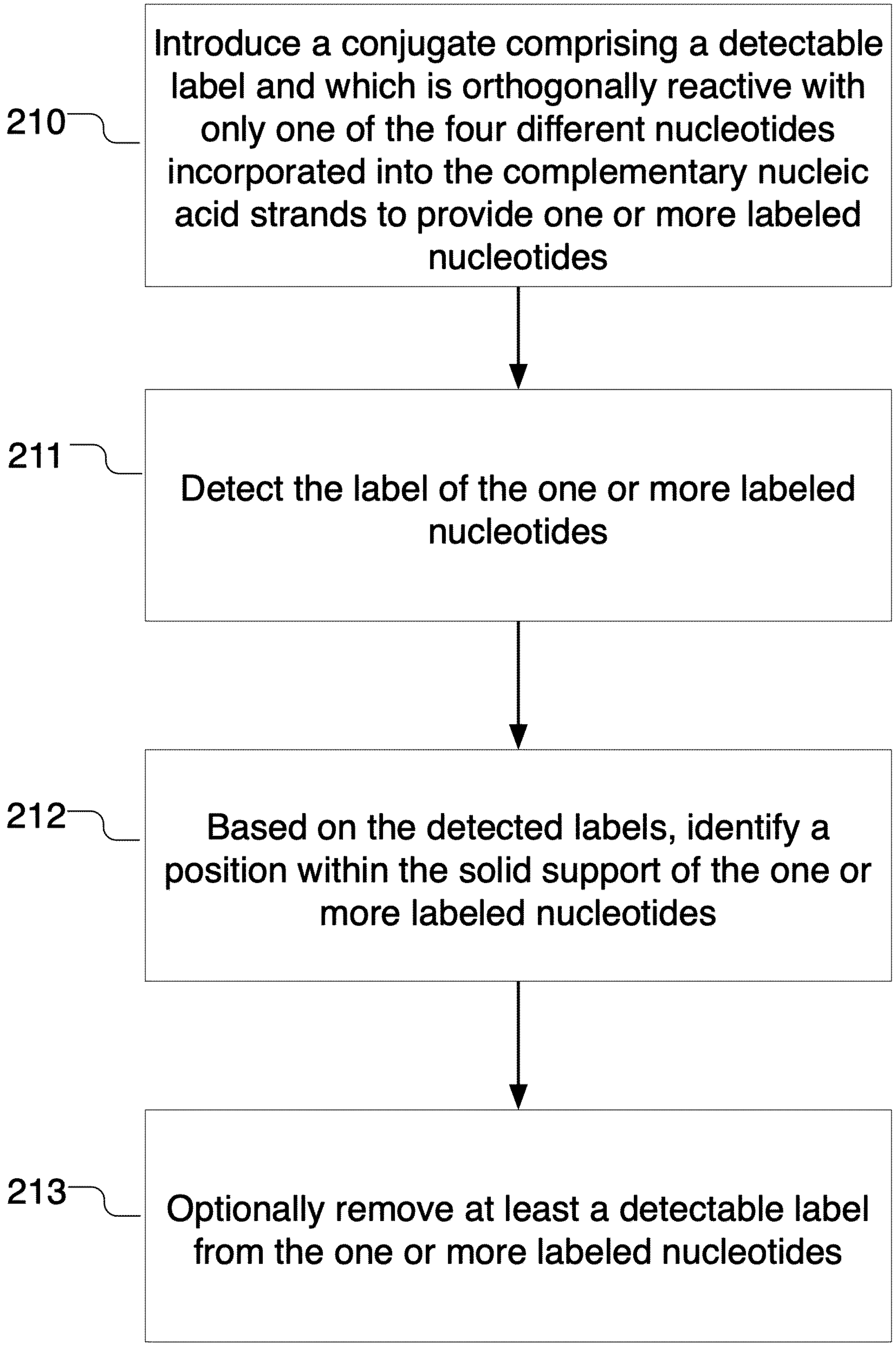
FIG. 2B provides a flowchart illustrating a method of sequentially labeling nucleotides incorporated into a nucleic acid strand in accordance with one embodiment of the present disclosure.

FIGS. 2A and 2B further illustrate the presently disclosed methods of sequencing a plurality of different target polynucleotide molecules, such as a plurality of different target polynucleotide molecules arrayed on a solid support, where the method comprises sequentially labeling different incorporated nucleotides with a different conjugate having a label. In some embodiments, the solid support is a flow cell loaded with a nucleic acid library to be sequenced. In some embodiments, one of four different nucleotides is first incorporated into each nascent nucleic acid copy strand present on the solid support (step 201), wherein each of the four different nucleotides includes (i) a 3-hydroxyl protecting group, and (ii) a reactive group coupled to a nucleobase through a cleavable linker, and where each different nucleotide of the four different nucleotides includes a different nucleobase and a different reactive group. In some embodiments, the nucleotides are incorporated by introducing a pool of four different nucleotides of Formulas (IA) or (IB) to the flow cell, where each of the four different nucleotides includes a different nucleobase (e.g. A, G, C, T/U) and a different $Z^1$ moiety.

In some embodiments, a first of the four different nucleotides has the structure of Formula (IC); a second of the four different nucleotides has the structure of Formula (ID); a third of the four different nucleotides has the structure of Formula (IE); and a fourth of the four different nucleotides has the structure of Formula (IF), provided that the reactive groups $Z^{1A}$, $Z^{1B}$, $Z^{1C}$, and $Z^{1D}$ are each different. In some embodiments, each of the $Z^{1A}$, $Z^{1B}$, $Z^{1C}$ and $Z^{1D}$ groups include a different oligonucleotide. In some embodiments, each of the $Z^{1A}$, $Z^{1B}$, $Z^{1C}$, and $Z^{1D}$ groups include a different LNA-modified oligonucleotide. In some embodiments, the different LNA-modified oligonucleotides of any one of the $Z^{1A}$, $Z^{1B}$, $Z^{1C}$, and $Z^{1D}$ groups have the sequence of any of SEQ ID NOS: 1 to 22 or SEQ ID NOS: 29 to 50 and are employed in its beta-L-configuration.

Subsequently, at least three of the four different nucleotides incorporated into each of the nascent nucleic acid strands are sequentially labeled (Step 202). In some embodiments, the at least three of the four different nucleotides incorporated into each of the nascent nucleic acid strands are sequentially labeled by sequentially introducing three different conjugates, such as three different conjugates having any of Formulas (IIA) to (IIE). In some embodiments, all four of the four different nucleotides incorporated into each of the nascent nucleic acid strands are sequentially labeled by sequentially introducing four different conjugates, such as four different conjugates having any of Formulas (IIA) to (IIE). In some embodiments, each different introduced conjugate of any of Formulas (IIA) to (IIE) reacts orthogonally with only one of the four different incorporated nucleotides. In some embodiments, each of the conjugates of any of Formulas (IIA) to (IIE) have a reactive moiety including an oligonucleotide. In some embodiments, each of the conjugates of any of Formulas (IIA) to (IIE) have a reactive moiety including an LNA-modified oligonucleotide. In some embodiments, the different LNA-modified oligonucleotides of the introduced conjugates have the sequence of any of SEQ ID NOS: 29 to 50 or SEQ ID NOS: 1 to 22, provided that any LNA-modified oligonucleotide sequence selected for a conjugate is complementary to one of the LNA-modified oligonucleotide sequences of the incorporated nucleotide.

For example, if $Z^{1A}$ includes an oligonucleotide having SEQ ID NO: 6, then the conjugate will include the complementary oligonucleotide having SEQ ID NO: 34. By way of another example, if $Z^{1B}$ includes an oligonucleotide having SEQ ID NO: 19, then the conjugate will include the complementary oligonucleotide having SEQ ID NO: 47. For example, if $Z^{1C}$ includes an oligonucleotide having SEQ ID NO: 4, then the conjugate will include the complementary oligonucleotide having SEQ ID NO: 32. For example, if $Z^{1D}$ includes an oligonucleotide having SEQ ID NO: 31, then the conjugate will include the complementary oligonucleotide having SEQ ID NO: 3. In some embodiments, each of the conjugates includes the same detectable label (e.g. the same magnetic nanoparticle). In other embodiments, at least one of the conjugates includes a detectable label which differs from the detectable label coupled to the other conjugates.

In this manner, different subsets of nucleotide-conjugate complexes (such as those having Formula (III)) are sequentially formed through the labeling process and independently detected. Given the sequential addition of the different conjugates and their orthogonal reactivity with the different incorporated nucleotides, the sequential labeling of the different incorporated nucleotides allows for the sequential determination of the positions within the solid support or flow cell of the different nucleotides incorporated into the nascent nucleic acid copy strands.

Turning to FIG. 2B, in some embodiments, each sequential labeling (step 202) comprises: introducing a conjugate including a detectable label and which is orthogonally reactive with only one of the four different nucleotides incorporated into the complementary nucleic acid strands to provide one or more labeled nucleotides (step 210); detecting the label of the one or more labeled nucleotides (step 211); based on the detected labels, identifying a position within the solid support or flow cell of the one or more labeled nucleotides (step 212); and optionally cleaving at least a detectable label from the one or more labeled nucleotides (step 213). In some embodiments, the steps of sequential labeling (step 202) are performed three times with three different conjugates (e.g. to form three different sets of detectable, labeled incorporated nucleotides). In other embodiments, the steps of sequential labeling (step 202) are performed four times with four different conjugates (e.g. to form four different sets of detectable, labeled incorporated nucleotides).

The skilled artisan will appreciate that the above process (steps 201 and 202) is for a single extension of the nascent nucleic acid copy strands complementary to the plurality of target polynucleotide molecules on the solid support or within the flow cell. This process may then be repeated for each iterative extension of the nascent nucleic acid copy strands complementary to the plurality of target polynucleotide molecules on the solid support. Before the complementary nascent nucleic acid copy strand may be further extended (i.e. before another cycle may be performed), the 3-hydroxyl protecting groups must be cleaved (step 203) from the four different nucleotides incorporated at step 201. Additionally, any remaining detectable labels that have not yet been cleaved must be removed prior to the next extension. In some embodiments, the 3-hydroxyl protecting groups and detectable labels are removed through the introduction of the same reagent.

Figure 3:
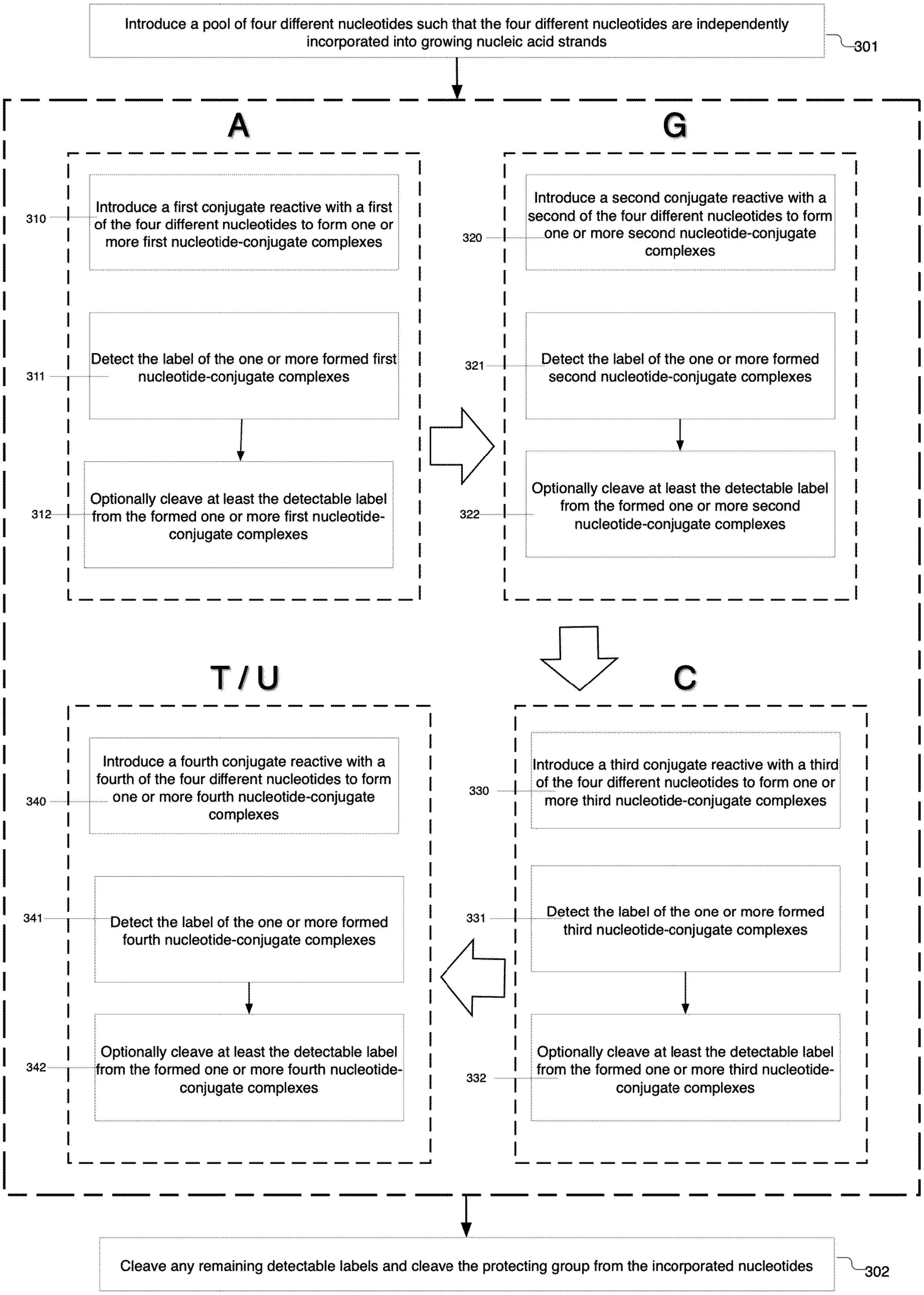
FIG. 3 provides a flowchart depicting a method of sequencing in accordance with one embodiment of the present disclosure.

With reference to FIG. 3, in some embodiments, the present disclosure provides for a method of sequencing a plurality of different target polynucleotide molecules on a solid support. In some embodiments, the method comprises (i) incorporating of one of four different nucleotides into a nucleic acid strand complementary of each of the plurality of target polynucleotides, wherein each of the four different nucleotides includes a reactive group coupled to a nucleobase through a cleavable linker and a 3-hydroxyl protecting group, and where each different nucleotide of the four different nucleotides includes a different nucleobase and a different reactive group (step 301). In some embodiments, the four different nucleotides have the structures provided in any of Formulas (IA) or (IB).

Subsequently, the method comprises (ii) labeling a first of the four different incorporated nucleotides by introducing a first conjugate having a detectable label, the first conjugate being orthogonally reactive with a first of the four different incorporated nucleotides (step 310). In some embodiments, the first conjugate has the structure of any of the conjugates of any of Formulas (IIA) to (IIE). As depicted in FIG. 3, the first of the four different nucleotides includes an adenine nucleobase, and a first conjugate is therefore reactive with only those incorporated adenine nucleotides. In some embodiments, the introduction of the first conjugate results in the formation of a first nucleotide-conjugate complex which is detectable.

Next, the method comprises (iii) determining the positions within the solid support of the complementary nucleic acid strands in which the first of the four different nucleotides was incorporated by detecting the labels of the first of the four different incorporated nucleotides (step 311). Then, the method comprises (iv) optionally cleaving the detectable label from the first of the four different incorporated nucleotides (step 312). This process is then repeated for at least two more of the different incorporated nucleotides, e.g. those nucleotides incorporated at step 301.

In some embodiments, the method comprises (v) labeling a second of the four different incorporated nucleotides by introducing a second conjugate having a detectable label, the second conjugate being orthogonally reactive with a second of the four different incorporated nucleotides (step 320). In some embodiments, the second conjugate has the structure of any of the conjugates of any of Formulas (IIA) to (IIE). As depicted in FIG. 3, the second of the four different nucleotides includes a guanine nucleobase, and a second conjugate is therefore reactive with only those incorporated guanine nucleotides. In some embodiments, the introduction of the second conjugate results in the formation of a second nucleotide-conjugate complex which is detectable.

Next, the method comprises (vi) determining positions within the solid support of the complementary nucleic acid strands in which the second of the four different nucleotides was incorporated by detecting the labels of the second of the four different incorporated nucleotides (step 321). The method then comprises (vii) optionally cleaving the detectable label from the second of the four different incorporated nucleotides (step 322).

In some embodiments, the method further comprises (viii) labeling a third of the four different incorporated nucleotides by introducing a third conjugate having a detectable label, the third conjugate being orthogonally reactive with a third of the four different incorporated nucleotides (step 330). In some embodiments, the third conjugate has the structure of any of the conjugates of any of Formulas (IIA) to (IIE). As depicted in FIG. 3, the third of the four different nucleotides includes a cytosine nucleobase, and a third conjugate is therefore reactive with only those incorporated cytosine nucleotides. In some embodiments, the introduction of the third conjugate results in the formation of a third nucleotide-conjugate complex which is detectable.

Next, the method comprises (ix) determining positions within the solid support of the complementary nucleic acid strands in which the third of the four different nucleotides have been incorporated by detecting the labels of the third of the four different incorporated nucleotides (step 331). In some embodiments, the method further comprises the steps of (x) optionally cleaving the detectable label from the third of the four different incorporated nucleotides (step 332).

In some embodiments, the positions within the solid support of the complementary nucleic acid strands in which the fourth of the four different nucleotides have been incorporated are determined by deduction. For example, by knowing the positions of the first, second, and third incorporated nucleotides (such as through the steps enumerated above), the position of the fourth incorporated nucleotides may be determined by identifying those positions which have not yet been detected.

In some embodiments, the method comprises (xi) labeling a fourth of the four different incorporated nucleotides by introducing a fourth conjugate having a detectable label, the fourth conjugate being orthogonally reactive with a fourth of the four different incorporated nucleotides (step 340). In some embodiments, the fourth conjugate has the structure of any of the conjugates of any of Formulas (IIA) to (IIE). As depicted in FIG. 3, the fourth of the four different nucleotides includes a thymine or uracil nucleobase, and a fourth conjugate is therefore reactive with only those incorporated thymine or uracil nucleotides. In some embodiments, the introduction of the fourth conjugate results in the formation of a fourth nucleotide-conjugate complex, which is detectable. In some embodiments the method next comprises (xii) determining positions within the solid support of the complementary nucleic acid strands in which the fourth of the four different nucleotides have been incorporated by detecting the labels of the fourth of the four different incorporated nucleotides (step 341). In some embodiments, the detectable labels may then be optionally cleaved (step 342).

In some embodiments, the method further comprises removing the 3'-hydroxyl protecting groups from each of the incorporated nucleotides (step 302), e.g. removing the 3-hydroxyl protecting groups from all of the nucleotides incorporated at step (i) (see step 302). In some embodiments, the method also includes removing any remaining detectable labels that have not yet been cleaved. In other embodiments, any remaining detectable labels are removed simultaneously with the 3-hydroxyl protecting group. In some embodiments, at least steps (i) through (ix) are repeated, such as for each cycle. In other embodiments, at least steps (i) through (x) are repeated, such as for each cycle. In other embodiments, steps (i) through (xii) are repeated.

Figure 4A:
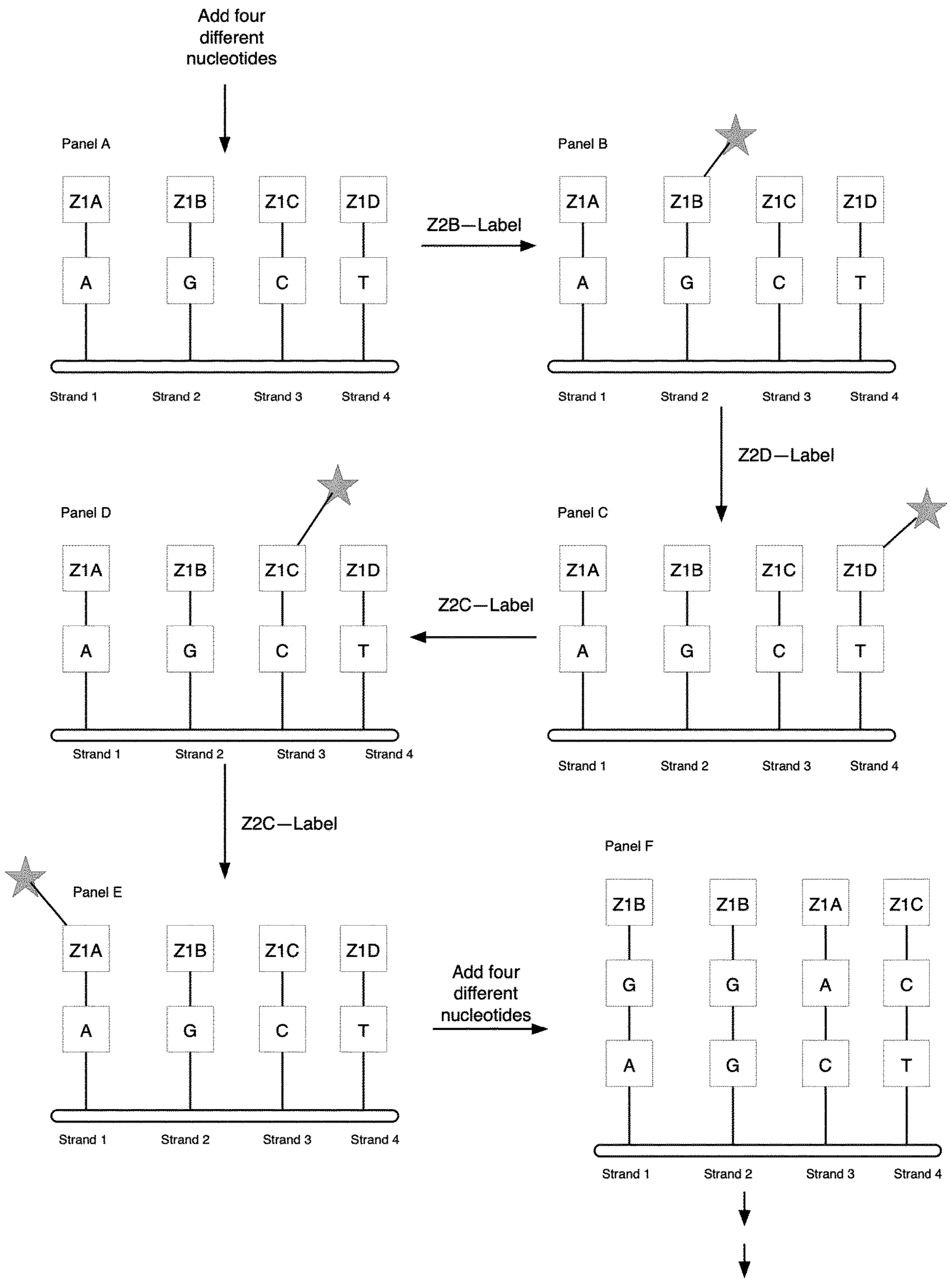
FIG. 4A illustrates a method of incorporating four different nucleotides of the present disclosure into four different nucleic acid strands, and then sequentially labeling each of the four different incorporated nucleotides in accordance with one embodiment of the present disclosure.

FIG. 4A illustrates the sequential identification of four different nucleotides incorporated during extension of nucleic acid copy strands. In particular, FIG. 4A illustrates the sequential labeling and detection of at least three of the four different nucleotides incorporated during nucleic acid copy strand extension. In some embodiments, the sequential labeling of the at least three of the four different incorporated nucleotides provides for the formation of at least three different nucleotide-conjugate complexes, where each different formed nucleotide-conjugate complex is derived from a different incorporated nucleotide.

In some embodiments, and with reference to Panel A of FIG. 4A, a pool of four different nucleotides (such as those of Formula (IA)) are first added to a flow cell. As depicted in Panel A, each of these four different nucleotides are incorporated into one of four different nascent nucleic acid strands (labeled "Strand 1," "Strand 2," "Strand 3," and "Strand 4"). As further depicted in Panel A, each of the four incorporated nucleotides includes a different $Z^1$ moiety ($Z^{1A}$, $Z^{1B}$, $Z^{1C}$, $Z^{ID}$) capable of orthogonally "reacting" with a different $Z^2$ moiety ($Z^{2A}$, $Z^{2B}$, $Z^{2C}$, $Z^{2D}$) of an introduced conjugate (such as those having Formula (IIA)). Additionally, each of the four different incorporated nucleotides includes a different nucleobase, here A, G, C, and T. For this particular example, assume that a $Z^{1A}$ moiety of a nucleotide is reactive with a $Z^{2A}$ moiety of a conjugate; that a $Z^{1B}$ moiety of a nucleotide is reactive with a $Z^{2B}$ moiety of a conjugate; that a $Z^{1C}$ moiety of a nucleotide is reactive with a $Z^{2C}$ moiety of a conjugate; and that a $Z^{1D}$ moiety of a nucleotide is reactive with a $Z^{2D}$ moiety of a conjugate.

Subsequently, a first conjugate (such as a first conjugate of Formula (IIA)) may be introduced to the flow cell which, in this example, is a first conjugate including a $Z^{2B}$ moiety. Given that the $Z^{2B}$ moiety of the first conjugate is reactive with only the $Z^{1B}$ moiety of the first nucleotide incorporated into Strand 2, only the first nucleotide incorporated at Strand 2 is labeled (see the "star" in Panel B of FIG. 4A). Said another way, a detectable first nucleotide-conjugate complex is formed, where the first nucleotide-conjugate complex corresponds to the first incorporated nucleotide having a guanine nucleobase and a $Z^{1B}$ moiety. This first labeled nucleotide (or first nucleotide-conjugate complex) may then be detected, allowing for the determination of the nucleotide incorporated into Strand 2. In some embodiments, after the first incorporated nucleotide is labeled (or first nucleotide-conjugate complex is formed), the detectable label is optionally cleaved from the first incorporated nucleotide (or first nucleotide-conjugate complex).

This process is then repeated such that at least two of the other nucleotides incorporated during extension are sequentially labeled. For example, a second conjugate of (such as a second conjugate of Formula (IIA)) may be introduced to the flow cell which, in this example, is a second conjugate including a $Z^{2D}$ moiety. Given that the $Z^{2D}$ moiety of the second conjugate is reactive with only the $Z^{1D}$ moiety of the second nucleotide incorporated into Strand 4, only the second nucleotide incorporated at Strand 4 is labeled (see the "star" in Panel C of FIG. 4A). Said another way, a detectable second nucleotide-conjugate complex is formed, where the second nucleotide-conjugate complex corresponds to the incorporated nucleotide of Formula (IA) having a thymine nucleobase and a $Z^{1D}$ moiety. This second labeled nucleotide (or second nucleotide-conjugate complex) may then be detected, allowing for the determination of the nucleotide incorporated into Strand 4. In some embodiments, the detectable label is optionally cleaved from the second incorporated nucleotide after the label of the second incorporated nucleotide is detected.

In some embodiments, a third conjugate (such as a third conjugate of Formula (IIA)) may be introduced to the flow cell which, in this example, is a third conjugate including a $Z^{2C}$ moiety. Given that the $Z^{2C}$ moiety of the third conjugate is reactive with only the $Z^{1C}$ moiety of the third nucleotide incorporated into Strand 3, only the third nucleotide incorporated at Strand 3 is labeled (see the "star" in Panel D of FIG. 4A). Said another way, a detectable third nucleotide-conjugate complex is formed, where the third nucleotide-conjugate complex corresponds to the third incorporated nucleotide having a cytosine nucleobase and a $Z^{1C}$ moiety. This third labeled nucleotide may then be detected, allowing for the determination of the nucleotide incorporated into Strand 3. In some embodiments, the detectable label is then optionally cleaved from the third incorporated nucleotide after the label of the third incorporated nucleotide is detected. In some embodiments, the process is performed a fourth time to label and detect the fourth nucleotide incorporated into Strand 1 (see Panel E of FIG. 4A where the "star" indicates the labeling of an incorporated adenine nucleotide). In other embodiments, the nucleotide incorporated into Strand 1 may be detected by means of deduction. In some embodiments, the detectable labels are not cleaved after each detection, but rather cleaved prior to the next extension at the same time the 3-hydroxyl protecting groups are removed.

Once all of the incorporated nucleotides in each nascent nucleic acid copy strand are identified, the 3-hydroxyl protecting groups present on any of the incorporated nucleotides of Formula (IA) may be removed such that each nascent nucleic acid copy strand may be further extended. Following the removal of all of the 3-hydroxyl protecting groups, a pool of four different nucleotides may subsequently be added so as to further extend each of the nascent nucleic acid copy strands. Once again, each of the four added nucleotides includes a different nucleobase and a different $Z^1$ moiety ($Z^{1A}$, $Z^{1B}$, $Z^{1C}$, $Z^{1D}$), capable of orthogonally "reacting" with a different $Z^2$ moiety ($Z^{2A}$, $Z^{2B}$, $Z^{2C}$, $Z^{2D}$) of an introduced conjugate having Formula (IIA). Panel F of FIG. 4A illustrates a second extension of the four nucleic acid copy strands and, in particular, the incorporation of different nucleotides into the four nucleic acid copy strands. In this example, the nucleotides of Formula (IA) incorporated into Strands 1 and 2 are both the same, while the nucleotides of Formula (IA) incorporated into Strands 3 and 4 are both different. Subsequently, the different conjugates of Formula (IIA) may then be sequentially added (such as in the same order as described above). This process may be repeated for a plurality of nucleic acid copy strand extension cycles.

The methods of sequencing by synthesis of the present disclosure are further illustrated with reference to a FIG. 4B, which illustrates the sequential formation and detection of different subsets of nucleotide-conjugate complexes (such as those nucleotide-conjugate complexes having Formula (III)). While FIG. 4A illustrates the sequential labeling and detection of different incorporated nucleotides (such as those of Formula (IA)) into four different nascent nucleic acid strands, B expands upon this concept and illustrates the utility of the present disclosure in parallel sequencing. In particular, FIG. 4B illustrates the sequential introduction of different conjugates of Formula (IIA) such that different populations of nucleic acid copy strands having different incorporated nucleotides of Formula (IA) may be sequentially labeled and detected.

Figure 4B:
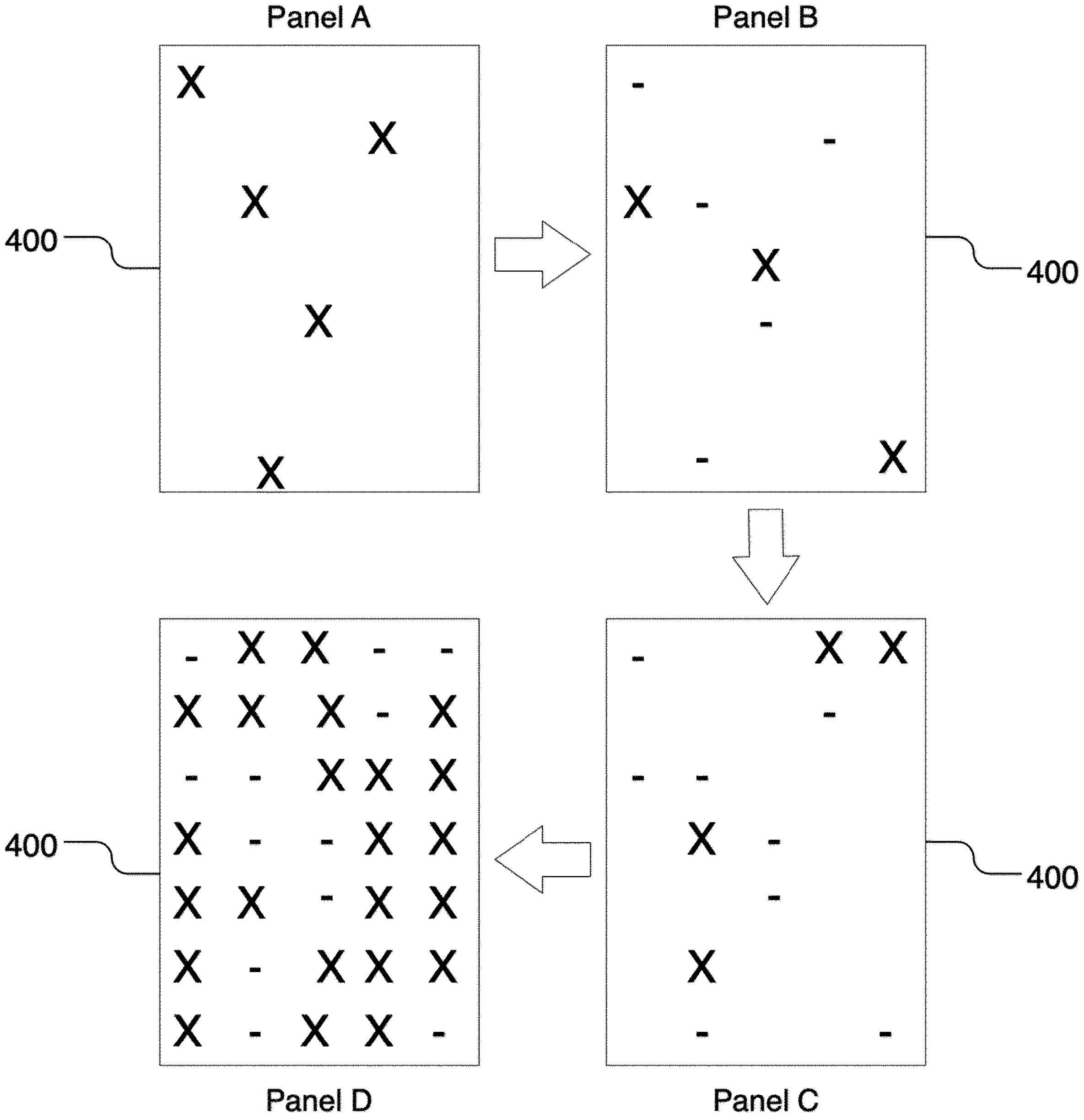
FIG. 4B depicts a method where sequentially formed subsets of nucleotide-conjugate complexes are sequentially detected in accordance with one embodiment of the present disclosure.

With reference to Panel A of FIG. 4B, assume that a pool of four different nucleotides of any of Formulas (IA) or (IB) is introduced to a flow cell 400 in admixture, where each of the four different nucleotides of Formula (IA) have a different nucleobase (e.g. A, G, C, T) and a different moiety $Z^1$. Here, each of the four different nucleotides of any of Formulas (IA) or (IB) provided to the flow cell 400 are independently incorporated as a first base in each individual nascent nucleic acid strand. The incorporation of the four different nucleotides of any of Formulas (IA) or (IB) in this example represents a first extension of each individual nascent nucleic acid strand.

Following the first extension, a first conjugate of any one of Formulas (IIA) to (IIE) is then added to the flow cell 400, where the first conjugate of any one of Formulas (IIA) to (IIE) includes a moiety $Z^2$ which is reactive with only a first of the four different nucleotides incorporated into the nascent nucleic acid. For example, a first conjugate of any one of Formulas (IIA) to (IIE) may include a $Z^{2B}$ moiety which is reactive only with the incorporated nucleotides of Formula (IA) having a $Z^{1B}$ moiety. The introduction of the first conjugate of any one of Formulas (IIA) to (IIE) results in formation of a first subset of detectable nucleotide-conjugates complex of Formula (III) (e.g. a first subset of nucleotide-conjugate complexes incorporated within a nascent nucleic acid). Given the orthogonal reactivity of the first conjugate of any one of Formulas (IIA) to (IIE), each of the formed detectable first nucleotide-conjugate complexes in the first subset of detectable nucleotide-conjugates complexes are derived from only one of the nucleotides of any of Formulas (IA) or (IB) incorporated into the nascent nucleic acid strands. By detecting the label of the one or more formed first nucleotide-conjugate complexes within the first subset of nucleotide-conjugate complexes, the positions of the nucleic acid copy strands within the flow cell 400 which had a first of the four different nucleotides incorporated may be determined (each represented by "X" in Panel A). In some embodiments, the detectable label of the each of the formed first detectable nucleotide-conjugate complexes in the first subset may be cleaved (these nucleotides are no longer detectable and are thus represented by "-" in Panel B of FIG. 4B). This process may then be repeated, e.g. repeated two more times or repeated three more times.

For example, a second conjugate of any one of Formulas (IIA) to (IIE) is then added to the flow cell 400, where the second conjugate of any one of Formulas (IIA) to (IIE) includes a moiety $Z^2$ which is reactive with only a second of the four different nucleotides incorporated into the nascent nucleic acid. For example, a second conjugate of any one of Formulas (IIA) to (IIE) may include a $Z^{2D}$ moiety which is reactive only with the incorporated nucleotides of Formula (IA) having a $Z^{1D}$ moiety. The introduction of the second conjugate of any one of Formulas (IIA) to (IIE) results in formation of a second subset of detectable nucleotide-conjugates complex of Formula (III). Given the orthogonal reactivity of the second conjugate of any one of Formulas (IIA) to (IIE), each of the formed detectable second nucleotide-conjugate complexes in the second subset of detectable nucleotide-conjugates complexes are derived from only one of the nucleotides of any of Formulas (IA) or (IB) incorporated into the nascent nucleic acid strands. By detecting the label of the one or more formed second nucleotide-conjugate complexes within the second subset of nucleotide-conjugate complexes, the positions of the nucleic acid copy strands within the flow cell 400 which had a second of the four different nucleotides incorporated may be determined (each represented by "X" in Panel B). In some embodiments, the detectable label of the each of the formed second detectable nucleotide-conjugate complexes in the second subset may be cleaved (these nucleotides are no longer detectable and are thus represented by "-" in Panel C of FIG. 4B).

With reference to Panels C and D of FIG. 4B, in some embodiments, the above recited steps are performed a third time and optionally performed a fourth time such that a third subset of nucleotide-conjugate complexes (derived from a third of the four different nucleotides incorporated into the nascent nucleic acid strand) and a fourth subset of nucleotide-conjugate complexes (derived from a fourth of the four different nucleotides incorporated into the nascent nucleic acid strand) may be sequentially formed and detected. Once the positions of all four bases incorporated into the nascent nucleic acid copy strands have been detected, any remaining detectable labels are removed. In addition, the 3-hydroxyl protecting groups of each of the four different incorporated nucleotides of any of Formulas (IA) or (IB) may then be removed to facilitate a second extension of each of the individual nascent nucleic acids within the flow cell 400.

In other embodiments, the process recited above is performed only a third time such that only a third subset of nucleotide-conjugate complexes (derived from a third of the four different nucleotides incorporated into the nascent nucleic acid strand) may be detected. In this particular embodiment, a fourth of the four different nucleotides incorporated into the nascent nucleic acid strand may be determined by deduction. For example, by knowing the positions of labels detected which correspond to the first, second, and third nucleotides incorporated within the nascent nucleic acid copy strands within the flow cell 400, the positions of the fourth nucleotides incorporated within the nascent nucleic acid copy strands may be determined by identifying those positions where no label has been detected.

In some embodiments, the method of sequencing a plurality of target polynucleotide molecules comprises: (a) binding a nucleic acid strand to a proximal wall within a fluid chamber; (b) in one or more rounds of addition, adding, to the fluid chamber, (i) an extendable primer, and (ii) a plurality of molecules of a nucleic acid polymerase; (c) adding, to the fluid chamber, four different nucleotides, where each of the four different nucleotides comprise (i) a 3-hydroxyl protecting group, and (ii) a reactive group coupled to a nucleobase through a cleavable linker, and where each different nucleotide of the four different nucleotides includes a different nucleobase and a different reactive group; (d) sequencing the plurality of target polynucleotide molecules, wherein the sequencing of the plurality of target polynucleotide molecules includes sequentially forming different subsets of nucleotide-conjugate complexes, where each nucleotide-conjugate complex within each different subset of formed nucleotide-conjugate complexes is derived from only one of the different nucleotides introduced to the fluid chamber and incorporated into nascent nucleic acid copy strands complementary to each of the plurality of target polynucleotide molecules.

In some embodiments, the sequential formation of different subsets of nucleotide-conjugate complexes comprises: introducing a conjugate including a detectable label and which is orthogonally reactive with only one of the four different nucleotides incorporated into the complementary nascent nucleic acid copy strands; detecting the formation of each nucleotide-conjugate complex within the subset by detecting the label of each introduced conjugate; determining a position within the solid support of each detected nucleotide-conjugate complex within the subset; and optionally cleaving at least a detectable label from each of the formed detectable nucleotide-conjugate complexes within the subset.

Some examples of a suitable polymerase include B-family (Type B) polymerases lacking the 3'-5' exonuclease activity.

In some embodiments, the polymerase is a thermostable polymerase. Thermostable nucleic acid polymerases include *Thermus aquaticus* Taq DNA polymerase, *Thermus* sp. Z05 polymerase, *Thermus flavus* polymerase, *Thermotoga maritima* polymerases, such as TMA-25 and TMA-30 polymerases, Tth DNA polymerase, *Thermococcus* Sp. 9° N (and variants Therminator DNA polymerase and Therminator II DNA polymerse), *Pyrococcus furiosus* (Pfu), *Pyrococcus woesei* (Pwo), *Thermatoga maritima* (Tma) and *Thermococcus Litoralis* (Tli or Vent), mutants thereof and the like.

In some embodiments, the polymerase lacks detectable 5'-3' exonuclease activity. Examples of DNA polymerases substantially lacking 5' to 3' nuclease activity include the Klenow fragment of *E. coli* DNA polymerase I; a *Thermus aquaticus* DNA polymerase (Taq) lacking the N-terminal 235 amino acids ("Stoffel fragment"), See U.S. Pat. No. 5,616,494. Other examples include a thermostable DNA polymerase having sufficient deletions (e.g., N-terminal deletions), mutations, or modifications so as to eliminate or inactivate the domain responsible for the 5'-3' nuclease activity. See, e.g., U.S. Pat. No. 5,795,762.

In some embodiments, the polymerase lacks detectable 3'-5' exonuclease activity. Examples of DNA polymerases substantially lacking the 3'-5' exonuclease activity include the Taq polymerase and its derivatives and any B-family (Type B) polymerase with naturally occurring or engineered deletion of the proofreading domain.

In some embodiments, the polymerase has been modified or engineered to enable or enhance incorporation of nucleotide analogs such as 3'-modified nucleotides; see, e.g., U.S. Pat. Nos. 10,150,454, 9,677,057, and 9,273,352.

In some embodiments, the polymerase has been modified or engineered to enable or enhance incorporation of nucleotide analogs such as 5'-phosphate-modified nucleotides; see, e.g., U.S. Pat. Nos. 10,167,455 and 8,999,676. In some embodiments, such polymerases are phi29 derived polymerases; see, e.g., U.S. Pat. Nos. 8,257,954 and 8,420,366. In some embodiments, such polymerases are phiCPV4 derived polymerases; see, e.g., U.S. Patent Publication No. US20180245147.

In some embodiments, the polymerase is modified or engineered by selection to successfully incorporate a desired modified nucleotide or to incorporate nucleotides and nucleotide analogs with desired accuracy and processivity. Methods of selecting such modified polymerases are known in the art; see, e.g., U.S. Patent Publication No US20180312904A1, entitled "Polymerase Compositions and Methods of Making and Using Same."

Synthesis of Nucleotides and Conjugates

Set forth below are examples of the synthesis of the nucleotides and conjugates described herein.

Example 1—Synthesis of 5'-thiol Modified ß-L-LNA oligonucleotides

5'-Thiol-modified ß-L-LNA oligonucleotides were synthesized in a 2×1 μmole scale synthesis on an ABI 394 DNA synthesizer using standard automated solid phase DNA synthesis procedure and applying phosphoramidite chemistry. Glen UnySupport PS (Glen Research cat no. 26-5040) and ß-L-LNA phosphoramidites as well as thiol-modifier C6 S—S (Glen Research cat. no. 10-1936) were used as building blocks. ß-L-LNA phosphoramidites were analogously synthesized as the ß-D-LNA phosphoramidites according to literature (Bioorg. Med. Chem. Lett. 2014, 24, 2699-2702; Tetrahedron 1998, 54, 3607-3630; Synthesis 2002, 6, 802-808) but starting from L-glucose instead of D-glucose, the disclosure of which is hereby incorporated by reference herein in its entirety. All phosphoramidites were applied at a concentration of 0.1 M in DNA grade acetonitrile. Standard DNA cycles with extended coupling time (180 sec), extended oxidation (45 sec) and detritylation time (85 sec) as well as standard synthesis reagents and solvents were used. The oligonucleotides were synthesized DMTon. A standard cleavage procedure was applied for the cleavage of the LNA oligonucleotides from the support by concentrated ammonia, residual protecting groups were also cleaved by treatment with concentrated ammonia (8 h at 56° C.). Crude 5'-disulfide modified ß-L-LNA oligonucleotides were evaporated and purified by RP HPLC (column: PRP-1, 7 μm, 250×21.5 mm (Hamilton, part no. 79352)) using a 0.1 M triethylammonium acetate pH 7/acetonitrile gradient. Product fractions were combined, desalted by dialysis (MWCO 1000, SpectraPor 6, part no. 132638) against water and concentrated. Thereafter, the disulfide was cleaved at room temperature in 30 minutes with 100 mM DTT pH 8.3-8.5 in phosphate buffer. Then the 5'-thiol-modified oligonucleotides were desalted by dialysis (MWCO 1000, SpectraPor 6, part no. 132638) against water, quantified and lyophilized.

Yields ranged from about 200 to 400 nmol.

5'-Thiol-modified ß-L-LNA oligonucleotides were analyzed by RP18 HPLC (Chromolith RP18e, Merck, part no. 1.02129.0001) using a 0.1 M triethylammonium acetate pH 7/acetonitrile gradient. Typical purities were >90%. Identity of 5'-thiol-modified ß-L-LNA oligonucleotides was confirmed by LC-MS analysis.

(SEQ ID NO: 19)
5'-HS-hexyl-β-LNA(TATCGC)-3'

(SEQ ID NO: 6)
5'-HS-hexyl-β-LNA(TCTTCC)-3'

(SEQ ID NO: 4)
5'-HS-hexyl-β-LNA(CTGTCA)-3'

(SEQ ID NO: 31)
5'-HS-hexyl-β-LNA(ACCAAC)-3'

Example 2—Synthesis of 5'-amino-modified ß-L-LNA oligonucleotides

5'-Amino-modified ß-L-LNA oligonucleotides were synthesized in a 2×1 μmole scale synthesis on an ABI 394 DNA synthesizer using standard automated solid phase DNA synthesis procedure and applying phosphoramidite chemistry. Glen UnySupport PS (Glen Research cat no. 26-5040) and ß-L-LNA phosphoramidites (see European Patent Application No. 19179046.8, filed on Jun. 7, 2019, entitled “Hybridizing all-LNA nucleotides,” the disclosures of which are hereby incorporated by reference herein in their entireties) as well as spacer phosphoramidite 18 (Sp18) (Glen Research cat. no. 10-1918) and 5'-amino-modifier C6 phosphoramidite (Glen Research cat. no. 10-1906) were used as building blocks. All phosphoramidites were applied at a concentration of 0.1 M in DNA grade acetonitrile. Standard DNA cycles with extended coupling time (240 sec) and extended oxidation (45 sec) as well as standard synthesis reagents and solvents were used for the assembly of 5'-amino-modified ß-L-LNA oligonucleotides which were synthesized MMTon. A standard cleavage procedure was applied for the cleavage of the LNA oligonucleotides from the support by concentrated ammonia, residual protecting groups were also cleaved by treatment with concentrated ammonia (8 h at 56° C.). Crude 5'-modified ß-L-LNA oligonucleotides were evaporated and purified by RP HPLC (column: PRP-1, 12-20 μm, 250×30 mm (Hamilton, part no. 79352)) using a 0.1 M triethylammonium acetate pH 7/acetonitrile gradient. Product fractions were combined and desalted by dialysis (MWCO 1000, SpectraPor 6, part no. 132638) against water, thereby also cleaving MMT group of MMTon purified oligonucleotides. Finally, the 5'-amino-modified oligonucleotides were quantified and lyophilized.

Typical yields: ca. 300 to 400 nmol.

5'-Amino-modified ß-L-LNA oligonucleotides were analyzed by RP18 HPLC (Chromolith RP18e, Merck, part no. 1.02129.0001) using a 0.1 M triethylammonium acetate pH 7/acetonitrile gradient. Typical purities were >90%.

The identity of 5'-amino-modified ß-L-LNA oligonucleotides was confirmed by LC-MS analysis.

(SEQ ID NO: 47)
5'-$H_2$N-hexyl-Sp18-β-LNA(GCGATA)-3'

(SEQ ID NO: 34)
5'-$H_2$N-hexyl-Sp18-β-LNA(GGAAGA)-3'

(SEQ ID NO: 32)
5'-$H_2$N-hexyl-Sp18-β-LNA(TGACAG)-3'

(SEQ ID NO: 3)
5'-$H_2$N-hexyl-Sp18-β-LNA(GTTGGT)-3'

Example 3—Synthesis of Nucleotides

Illustrated and described herein is a method of synthesizing the nucleotides of the present disclosure.

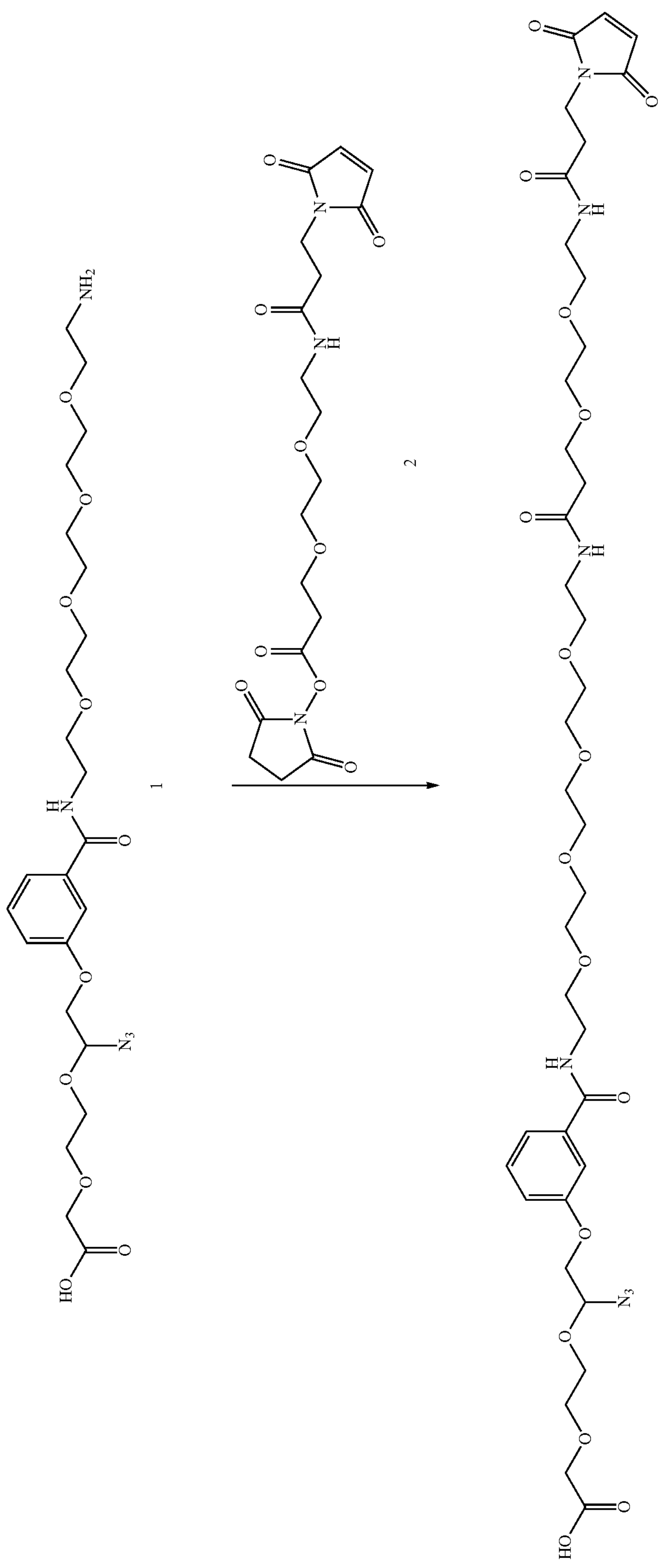
1
2
3

-continued
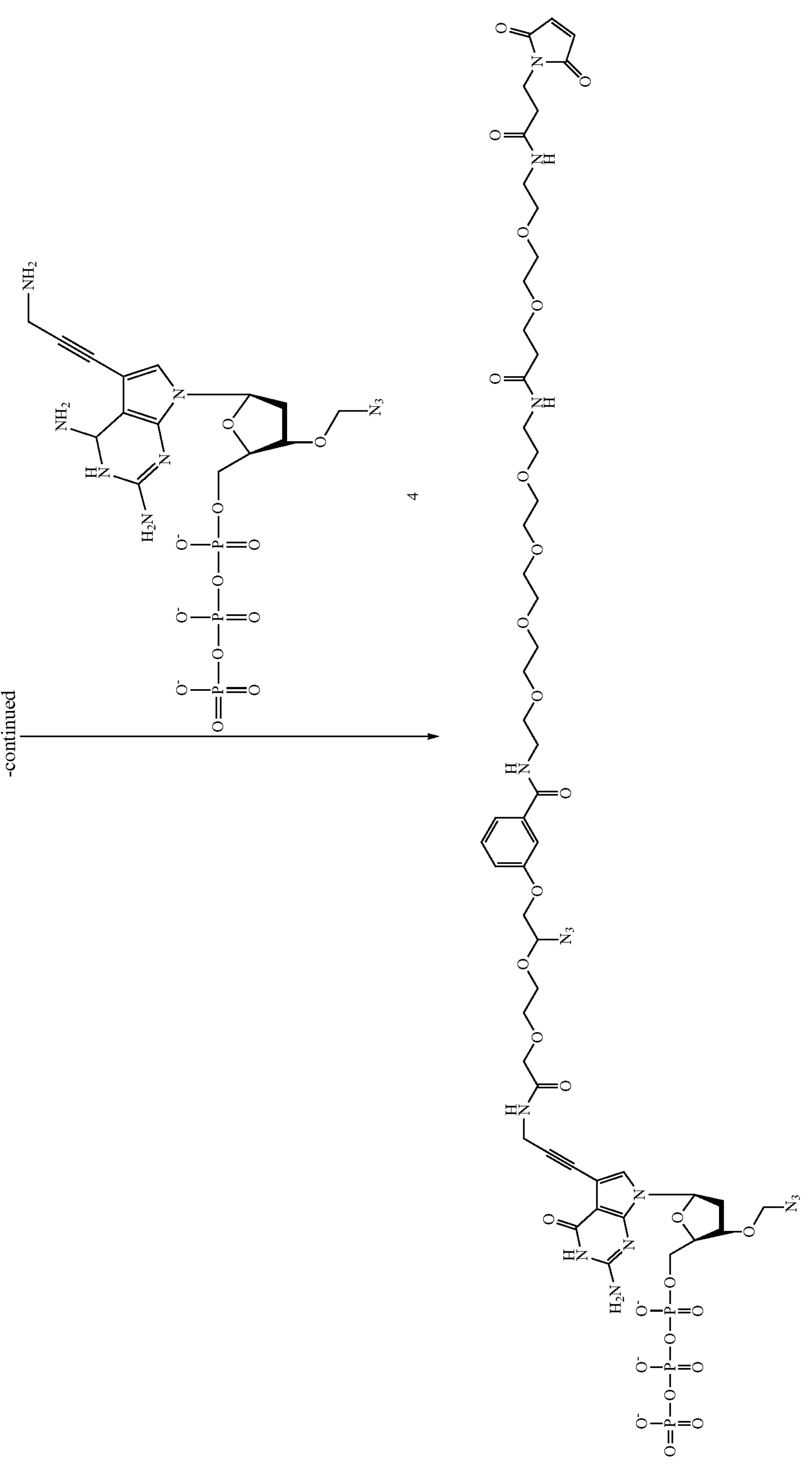
4
8

-continued
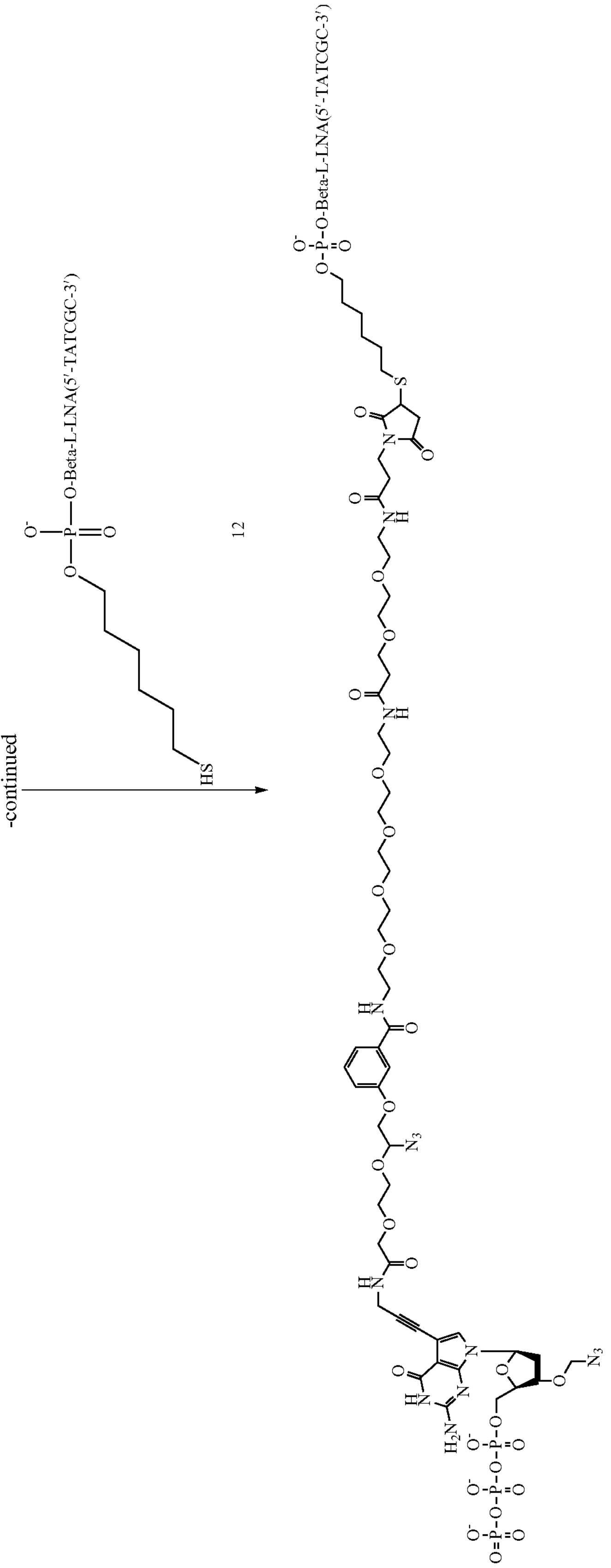
12
16

-continued
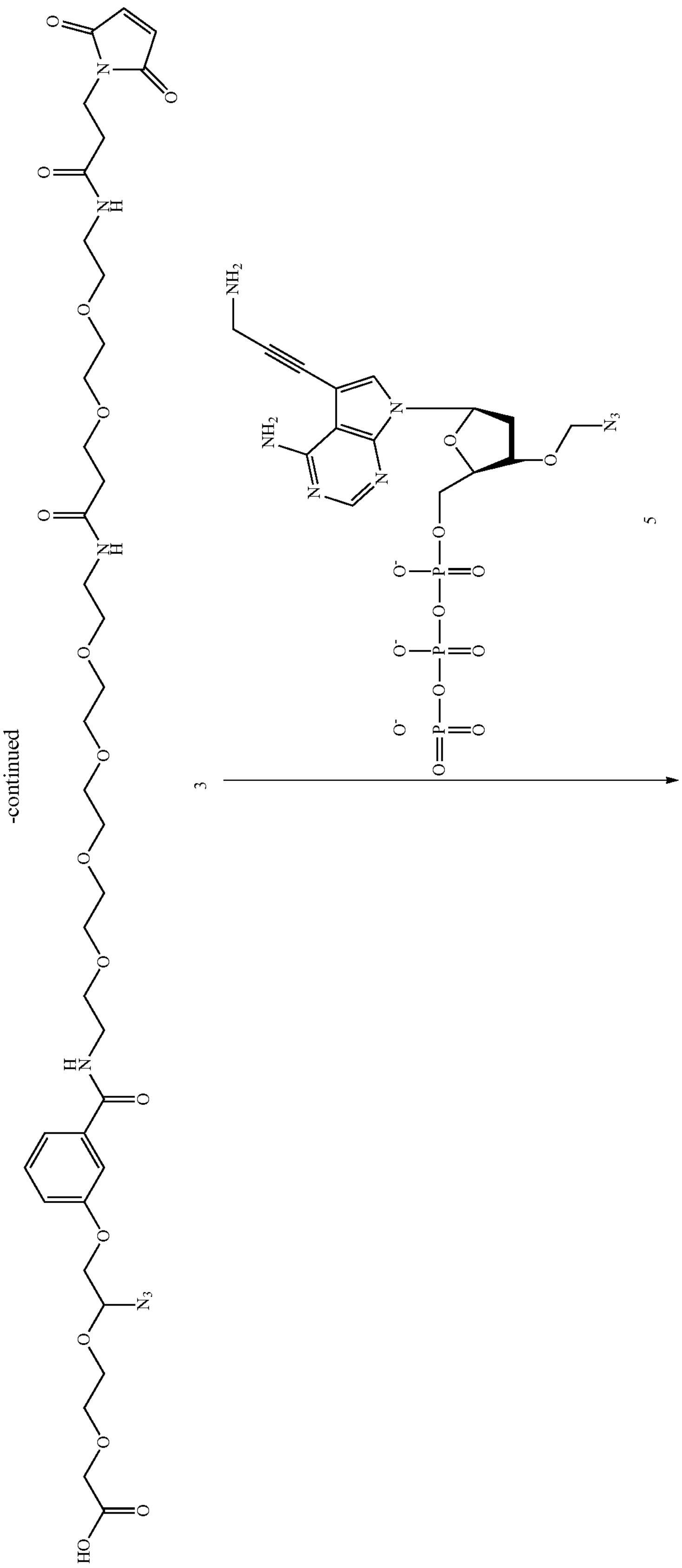
3
5

-continued
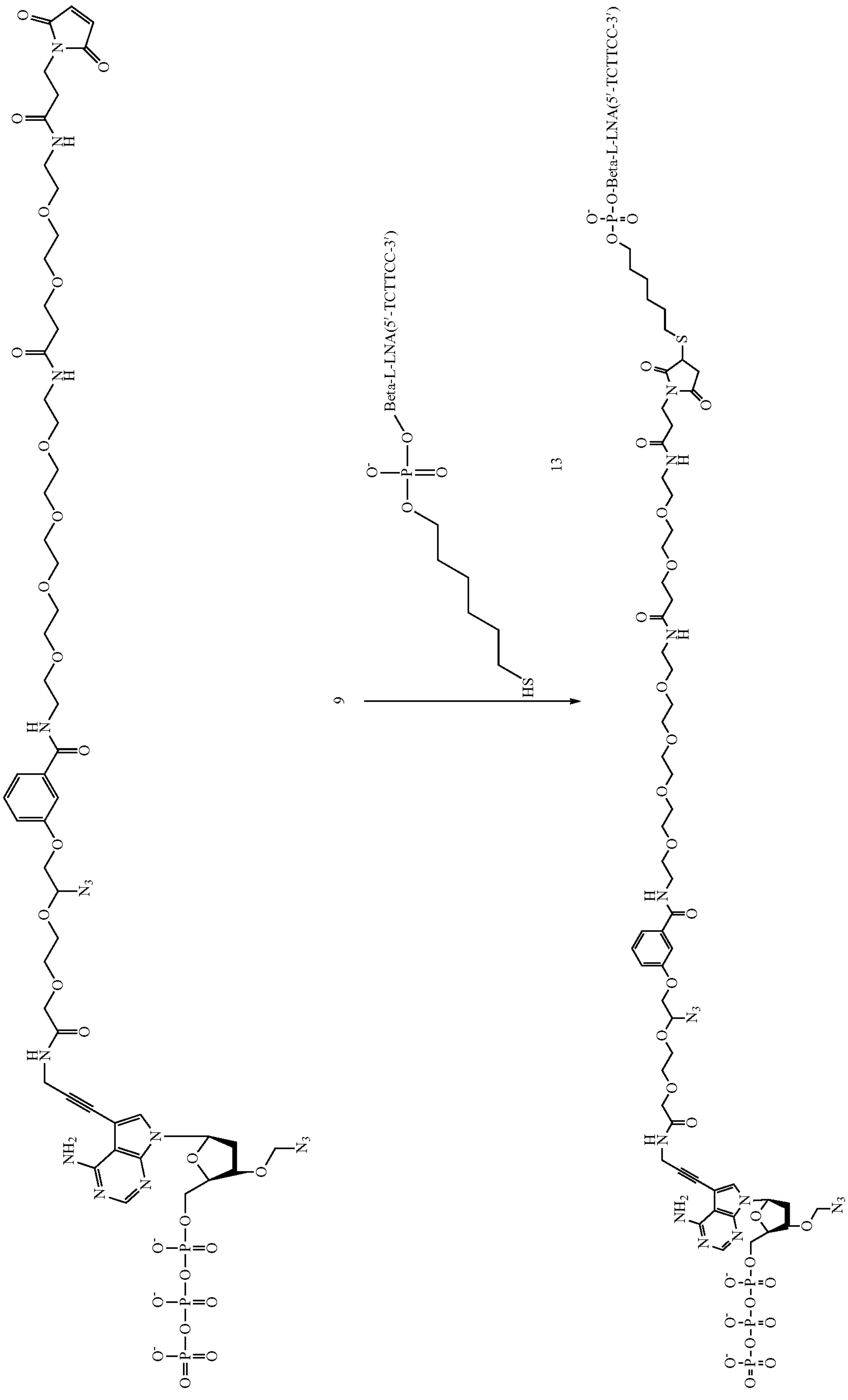
9
13
17

-continued
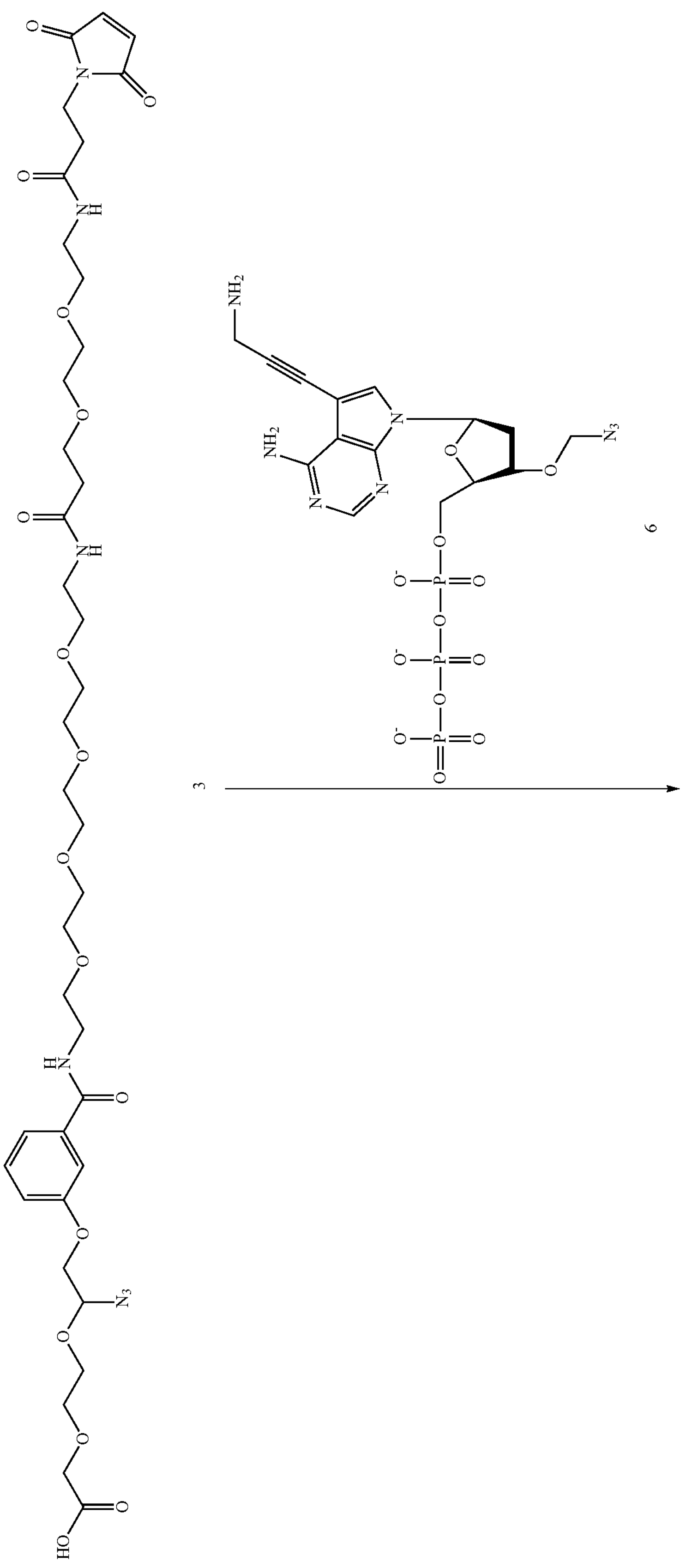
3
6

-continued
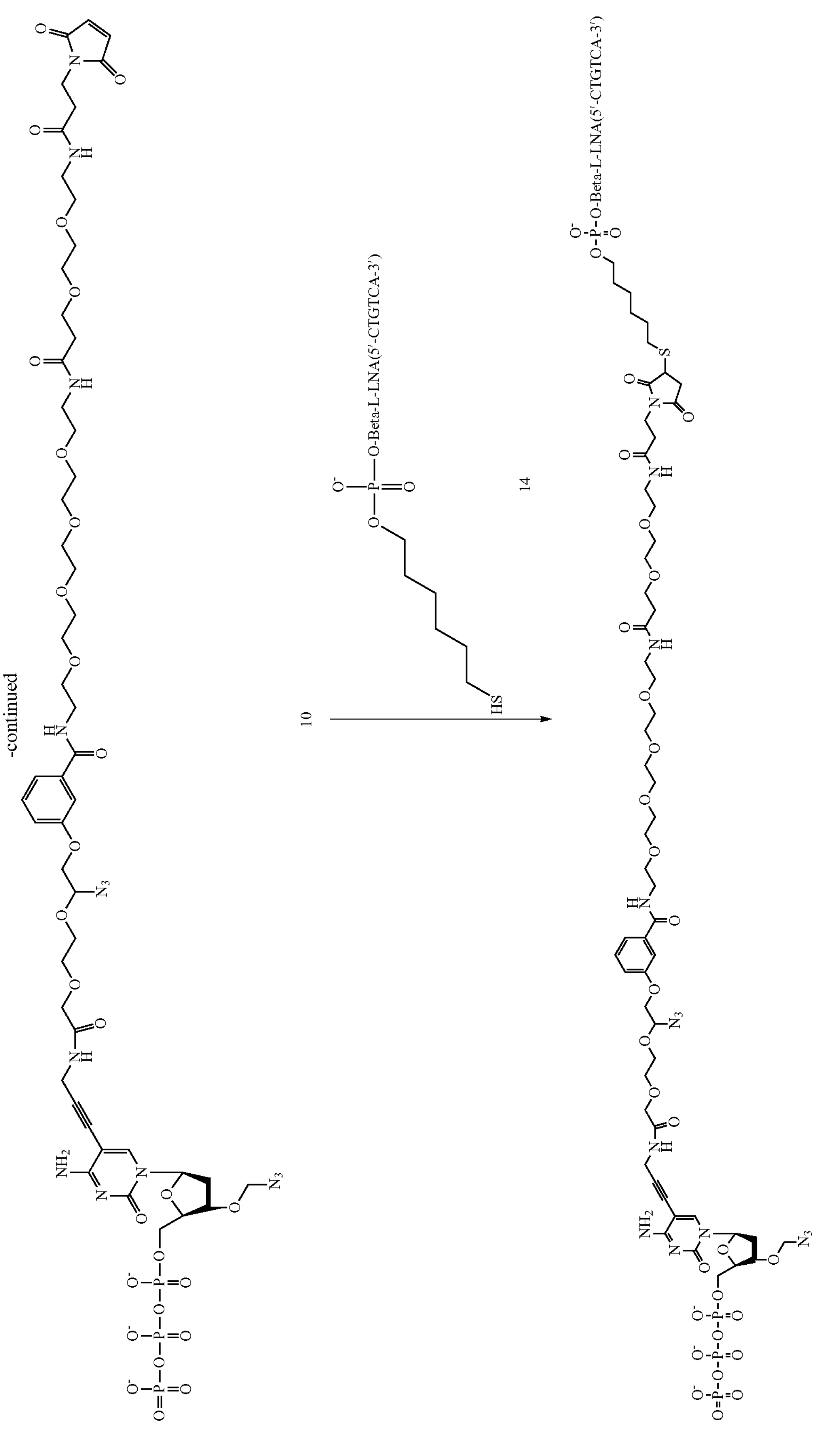
10
14
18

-continued
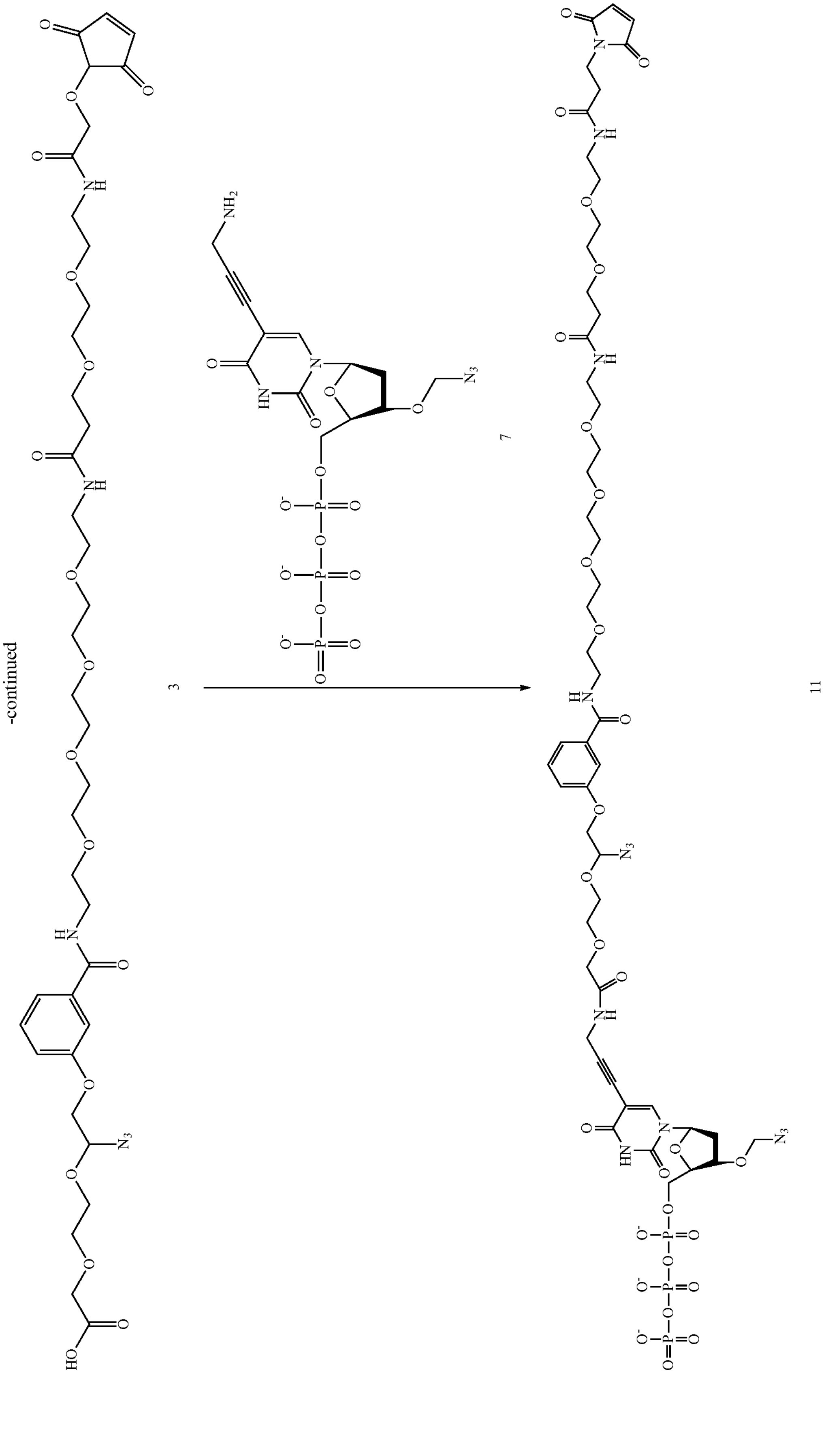
3
7
11

-continued
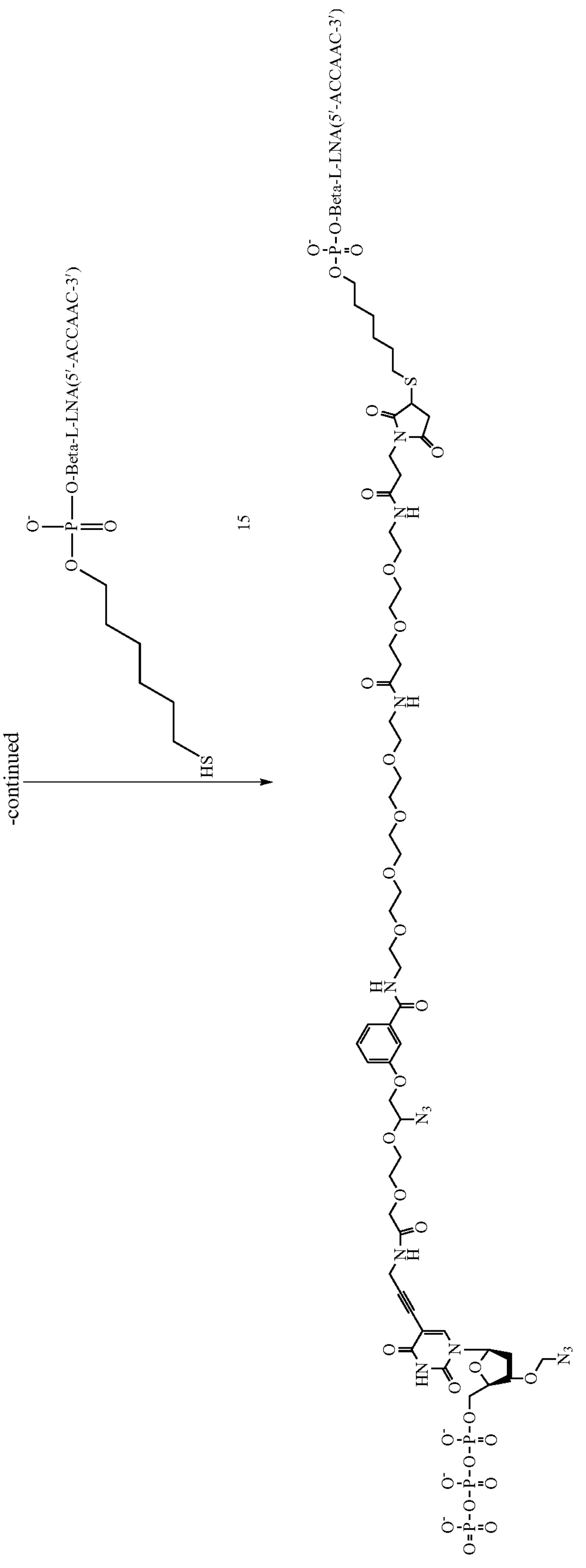
15
19

Linker molecule 1 was synthesized according to procedures described in US 2017/0240961 A1 with the difference that 3,6,9,12-tetraoxatetradecane-1,14-diamine (CAS 68960-97-4, e.g. from Carbosynth (FD164979)) instead of PEG12 diamine was used.

3'-O-Azidomethyl-nucleoside triphosphates modified by a 3-aminoprop-1-ynyl group at the 5-position of uracil and cytosine and 7-position of 7-deaza-adenine and 7-deazaguanine (compounds 4-7) were synthesized according to procedures described in WO 2004/018497. Propargyl-modified-3'-azidomethyl-dNTPs (compounds 4-7) can also be purchased from MyChem, LLC, San Diego, Cal.

Synthesis of Linker Molecule 3:

Linker molecule 1 (1 mmol, 534 mg) was dissolved in DMF (10 ml) and N-methylmorpholine (1.2 ml). To this solution a solution of maleimide-PEG2-succinimidyl ester 2 (Sigma Aldrich 746223) (1.1 mmol (468 mg)) in DMF (10 ml) was added slowly and then stirred for 16 h at ambient temperature. The solvent was removed under vacuum. The residue was acidified by addition of 1 M HCl and the product was extracted with ethyl acetate. The combined organic layers were washed with water and brine und dried (Na2SO4). The solvent was removed under reduced pressure and the crude product (0.8 g) was used in the next step.

Synthesis of Nucleotide Linker Conjugates 8-11:

To a stirred solution of linker molecule 3 (11.3 mg, 13.2 μmol) in dry DMF (2 ml) N,N'-disuccinimidyl carbonate (3.4 mg, 13.2 μmol) and 4-dimethylaminopyridine (1.6 mg, 13.2 μmol) were added. The reaction mixture was stirred at ambient temperature for 2 h. TLC indicated complete conversion. This solution was directly used to couple with nucleotides 4-7 (13 μmol) in 0.1 M $NaHCO_3$/Na2O3 buffer pH 8.7 (0.3 ml). The reaction mixture was stirred for 3 h at ambient temperature and purified by reversed phase HPLC to result nucleotide linker conjugates 8-11. Typical yields were 6 to 8 μmol.

Synthesis of Nucleotide ß-L-LNA Conjugates 16-19:

Nucleotide linker conjugates 8-11 (240 nmol) and 5'-thiol modified ß-L-LNA (12-15) (200 nmol) were each dissolved in 2 ml of Dulbecco's phosphate buffered saline (Sigma D8537) and mixed. After 10 min at ambient temperature the reaction was complete (controlled by RP-HPLC). Then the reaction mixture was dialyzed (MWCO 1000, SpectraPor 6, part no. 132638) against water, concentrated and purified by RP HPLC (column: XBridge prep C18 5 μm OBD, 19×250 mm (Waters, P/N 186004021) using a 0.1 M triethylammonium acetate pH 7/acetonitrile gradient. Product fractions were combined, desalted by dialysis (MWCO 1000, SpectraPor 6, part no. 132638) against water, quantified and lyophilized.

Yields ranged from about 120 to 160 nmol.

Nucleotide 13-L-LNA conjugates 16-19 were analyzed by RP18 HPLC (Chromolith RP18e, Merck, part no. 1.02129.0001) using a 0.1 M triethylammonium acetate pH 7/acetonitrile gradient. Typical purities were >95%. Identity of nucleotide 13-L-LNA conjugates 16-19 was confirmed by LC-MS analysis.

Example 4—Synthesis of Conjugates

Illustrated and described herein is a method of synthesizing the conjugates of the present disclosure.

24
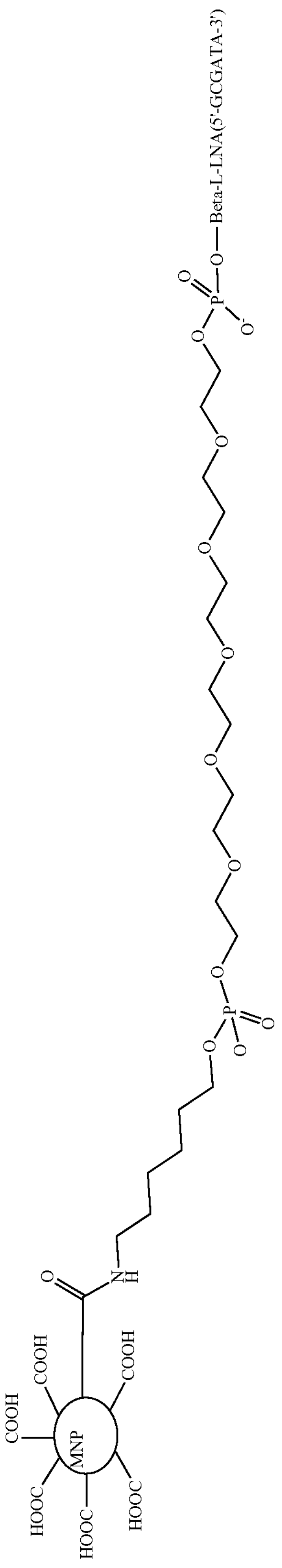
25
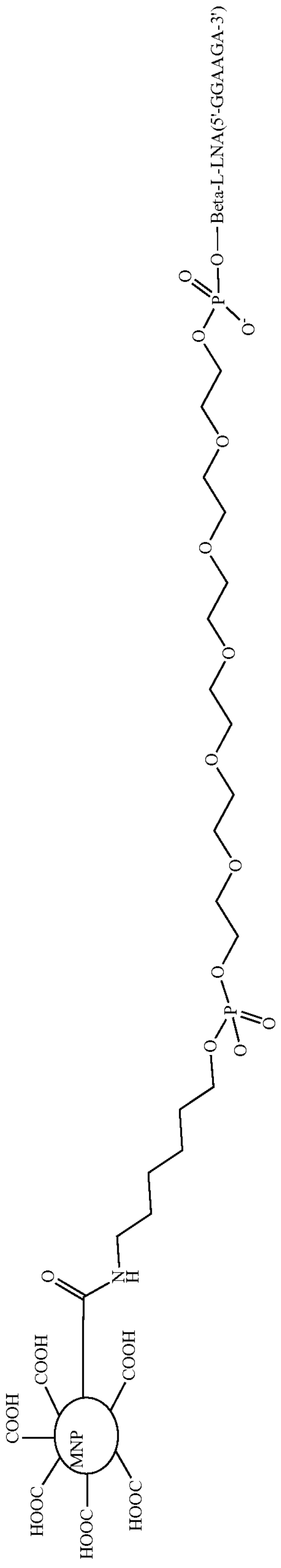
26
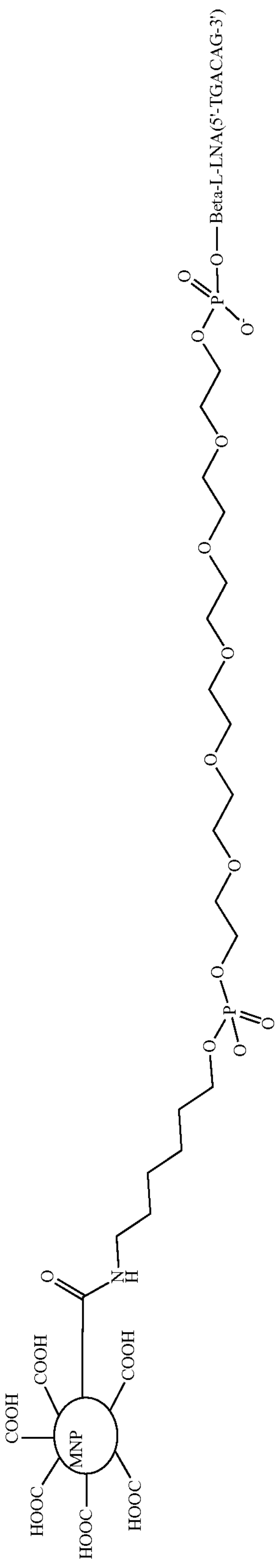

-continued
27
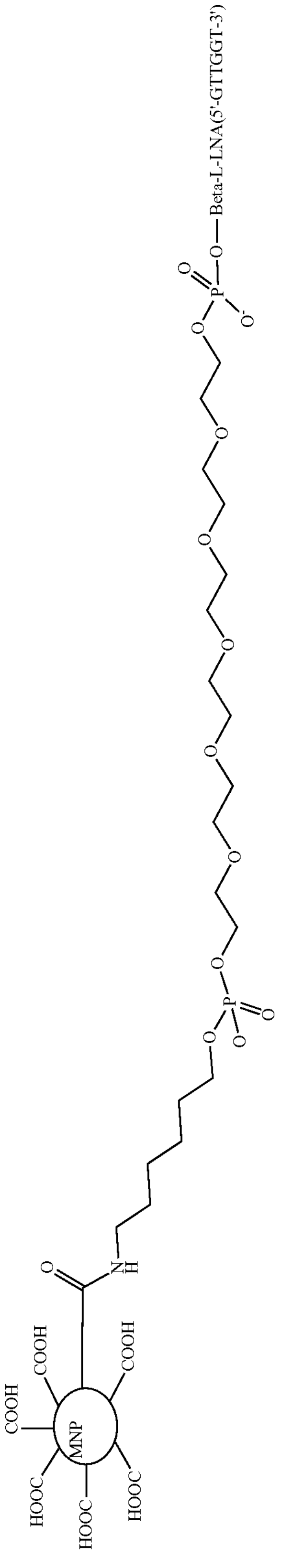

Carboxyl Iron Oxide Nanoparticles (diameter from 5 to 30 nm, e.g. from Ocean NanoTech) were activated using EDC/sulfo-NHS followed by conjugation to 5'-amino modified ß-L-LNA oligonucleotides using different ratios to yield magnetic nanoparticles with low oligonucleotide loading (24-27).

0.2 mL of resuspended (DI water) magnetic nanoparticles (5 mg/mL) were aliquoted into a 1.5 mL microcentrifuge tube and then 0.2 mL of activation buffer (25 mM MES, pH 6.0) were added. Thereafter, 0.01 mL of sulfo-NHS solution (10 mg/mL DI water) and 0.01 mL of EDC solution (10 mg/mL DI water) were added. The suspension was continuously mixed for 15 min at room temperature. Then unreacted EDC/sulfo-NHS was separated by NAP-10 column (GE 17-0854-02). The 5'-amino-modified oligonucleotide in 10 mM PBS buffer pH 7.4 (5 nmol and lower per 1 mg nanoparticles) was added to the magnetic nanoparticles eluted from the column and reacted for 2.5 h at room temperature with continuous mixing. Thereafter, 0.1 mL of quenching buffer (100 mM Tris-HCl, pH 7.4) were added to the magnetic nanoparticles suspension and reacted for 30 min at room temperature with continuous mixing. Then unconjugated oligonucleotide was removed by magnetic separation. The magnetic nanoparticles were resuspended in storage buffer (10 mM PBS, pH 7.4). Anion exchange HPLC or gel electrophoresis may be employed to separate the magnetic nanoparticles with different stoichiometries and isolate magnetic nanoparticles monofunctionalized with an oligonucleotide.

If oligonucleotide is multiply conjugated:

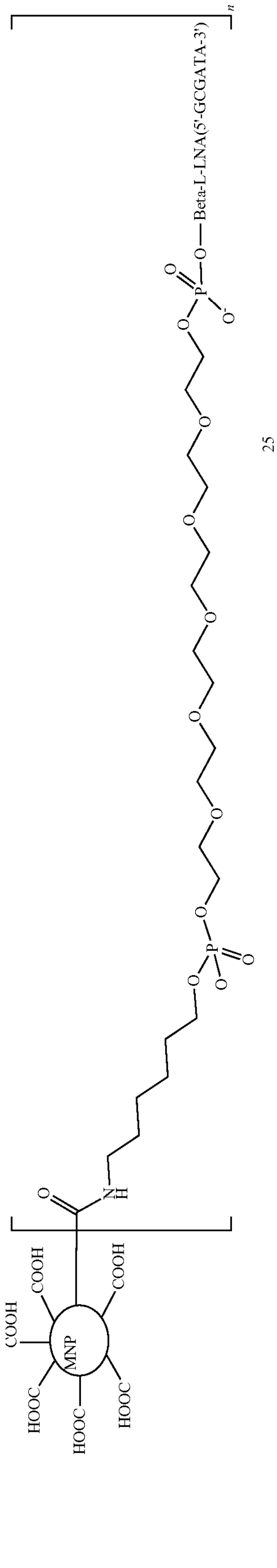
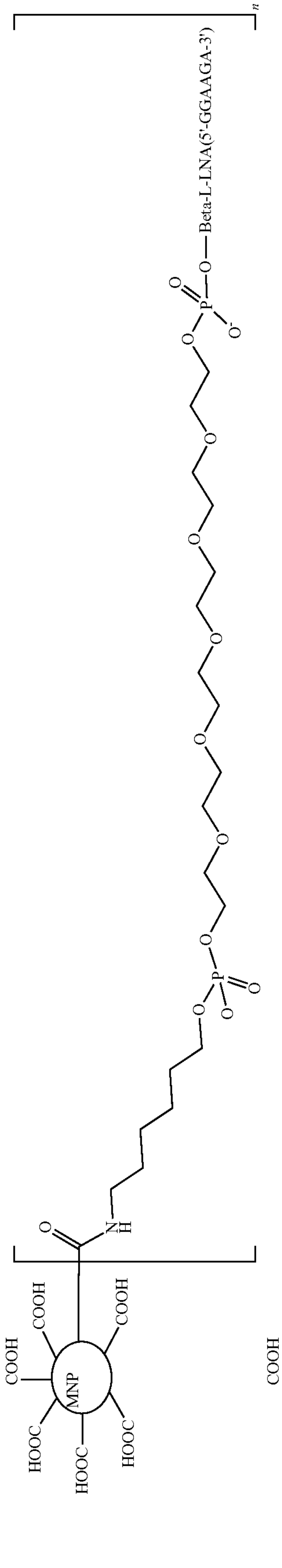
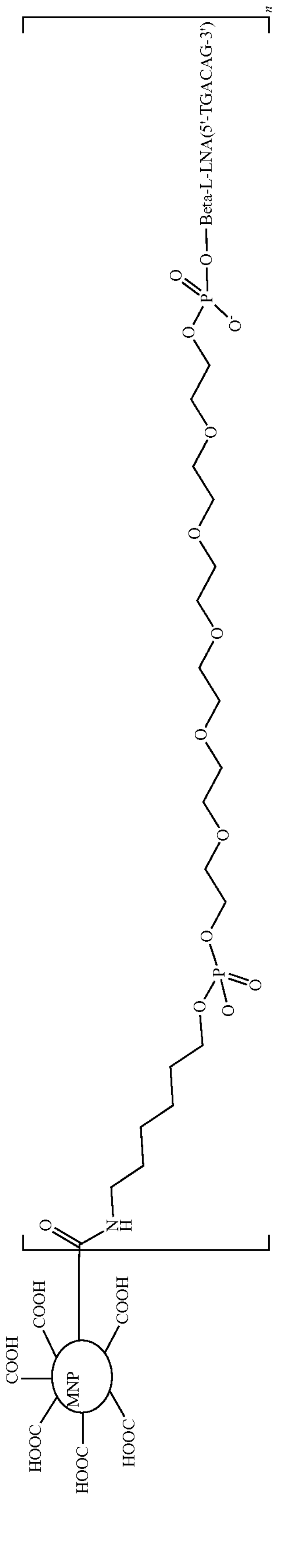

-continued
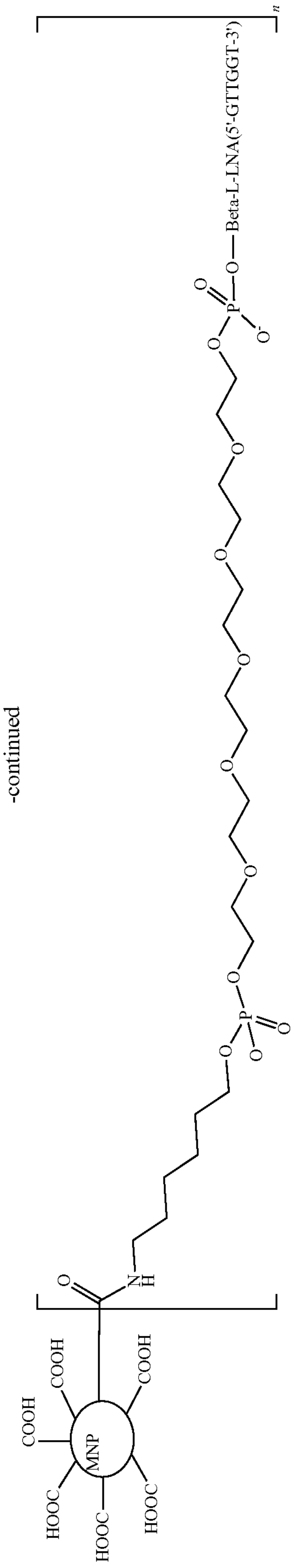

Example 5

Reaction conditions for reacting nucleotide or oligo-/polynucleotide including $Z^1$ with a conjugate including $Z^2$ (conjugate in excess, e.g. 1 pM-1 mM, preferred 0.1-25 µM (depending on sensors on chip and excess applied):

Incubation time at r.t. 10 s to 600 s, preferred 10 to 60 sec

1) Reactive Group: Oligonucleotide

Conjugate is applied in a buffered solution, containing e.g. Tris, Hepes, sodium phosphate, sodium chloride, potassium acetate (preferred pH 6-8; preferred salt conc. 10-100 mM (monovalent) and/or 0-10 mM divalent ions (Mg2+); detergent, e.g. polidocanol (Thesit) may be added.

2) Reactive Group: Hapten Antibody

Conjugate is applied in a buffered solution, containing e.g. Tris, Hepes, sodium phosphate, sodium chloride, potassium acetate (preferred pH 6-8; preferred salt conc. 10-100 mM; detergent, e.g. polidocanol (Thesit) may be added.

3) Reactive Group: Host Guest

Conjugate is applied in a buffered solution, containing e.g. Tris, Hepes, sodium phosphate, sodium chloride, potassium acetate (preferred pH 6-8; preferred salt conc. 10-100 mM; detergent, e.g. polidocanol (Thesit) may be added.

4) click

4a) CuAAC

Conjugate is applied in a buffered solution, containing e.g. Tris, Hepes, sodium phosphate, sodium chloride, potassium acetate (preferred pH 6-8; preferred salt conc. 10-100 mM and click reagents (0.25 mM copper(II) sulfate, 1.25 mM THPTA ligand, 5 mM sodium ascorbate, 5 mM aminoguanidine); detergent, e.g. polidocanol (Thesit) may be added.

4b) Copper-Free Click

Conjugate is applied in a buffered solution, containing e.g. Tris, Hepes, sodium phosphate, sodium chloride, potassium acetate (preferred pH 6-8; preferred salt conc. 10-100 mM; detergent, e.g. polidocanol (Thesit) may be added.

4c) TCO/Tetrazine Click (Inverse-Demand Diels-Alder Cycloaddition Reaction)

Conjugate is applied in a buffered solution, containing e.g. Tris, Hepes, sodium phosphate, sodium chloride, potassium acetate (preferred pH 6-8; preferred salt conc. 10-100 mM; detergent, e.g. polidocanol (Thesit) may be added.

Example 6—Synthesis of 5'-biotinylated 13-L-LNA oligonucleotides

5'-Biotinylated ß-L-LNA oligonucleotides were synthesized in a 2×1 µmole scale synthesis on an ABI 394 DNA synthesizer using standard automated solid phase DNA synthesis procedure and applying phosphoramidite chemistry. Glen UnySupport PS (Glen Research cat no. 26-5040) and ß-L-LNA phosphoramidites (see European Patent Application No. 19179046.8, filed on Jun. 7, 2019, entitled “Hybridizing all-LNA nucleotides,” the disclosures of which are hereby incorporated by reference herein in their entireties) as well as spacer phosphoramidite 18 (Sp18) (Glen Research cat. no. 10-1918) and 5'-biotin phosphoramidite (Glen Research cat. no. 10-5950) were used as building blocks. All phosphoramidites were applied at a concentration of 0.1 M in DNA grade acetonitrile. Standard DNA cycles with extended coupling time (240 sec) and extended oxidation (45 sec) as well as standard synthesis reagents and solvents were used for the assembly of 5'-biotinylated ß-L-LNA oligonucleotides which were synthesized DMToff. A standard cleavage procedure was applied for the cleavage of the LNA oligonucleotides from the support by concentrated ammonia, residual protecting groups were also cleaved by treatment with concentrated ammonia (8 h at 56° C.). Crude 5'-biotinylated ß-L-LNA oligonucleotides were evaporated and purified by RP HPLC (column: PRP-1, 12-20 µm, 250×30 mm (Hamilton, part no. 79352)) using a 0.1 M triethylammonium acetate pH 7/acetonitrile gradient. Product fractions were combined and desalted by dialysis (MWCO 1000, SpectraPor 6, part no. 132638) against water. Finally, the 5'-biotinylated oligonucleotides were quantified and lyophilized.

Typical yields ranged from about 200 to about 400 nmol.

5'-Biotinylated ß-L-LNA oligonucleotides were analyzed by RP18 HPLC (Chromolith RP18e, Merck, part no. 1.02129.0001) using a 0.1 M triethylammonium acetate pH 7/acetonitrile gradient. Typical purities were >90%.

The identity of 5'-biotinylated ß-L-LNA oligonucleotides was confirmed by LC-MS analysis.

```
                                    (SEQ ID NO: 47)
5'-Biotin-Sp18-β-LNA(GCGATA)-3'

                                    (SEQ ID NO: 34)
5'-Biotin-Sp18-β-LNA(GGAAGA)-3'

                                    (SEQ ID NO: 57)
5'-Biotin-Sp18-β-LNA(TGAGTG)-3'

                                    (SEQ ID NO: 3)
5'-Biotin-Sp18-β-LNA(GTTGGT)-3'
```

Example 7—Conjugation of Streptavidin-Coated Nanoparticles (NP10 nm; NP20 nm) with Different Biotinylated L-LNAs Materials

| |
|---|
| NP10 (SHS-10, LOT# 19313SHS) (available from Ocean Nanotech (San Diego, CA 92126, US)) |
| NP20 (SHS-20, LOT# 20027SHS) (available from Ocean Nanotech (San Diego, CA 92126, US)) |
| L-LNA1 5’-Bi-Sp18-gttggt-3’(L-LNA) |
| L-LNA2 5’-Bi-Sp18-gcg ata-3’(L-LNA) |
| L-LNA3 5’-Bi-Sp18-ggaaga-3’ (L-LNA) |
| L-LNA4 5’-Bi-Sp18-tgagtg-3’(L-LNA) |
| KP (Kaliumphosphate buffer) pH 7.4 (50 mM $K_2HPO_4$/$KH_2PO_4$ and 150 mM KCl) |

Equipment:

1.5 mL LB-Eppendorf Vials

Spinfilter system from Vivaspin (Sartorius 500): 10K MWCO, filter volume 100 µL, volume supernatant ca. 500 µL Centrifuge: Eppendorf 5415D; 13 200 rpm/16 100 ref max Centrifuge: Eppendorf 5417R; 25 000 ref max, Temp: (21° C.)

Thermo-Shaker

Vortex

EXPERIMENTAL 3 different experiments were performed with 8 samples each, (2 NP×4 L-LNAs) as set forth below:

(A) 0.5 mg NP; Purification: Centrifugation: Eppendorf 5417R; 25,000 rcf max, (21-∞C)

(B) 0.1 mg NP; Purification: Spinfilter 10K, 0.5 mL, Centrifuge: Eppendorf 5415D, 8000 rpm (C) 0.3 mg NP; Purification: Spinfilter 10K, 0.5 mL, Centrifuge: Eppendorf 5417R, 5000 ref Experiment (A)

0.5 mg (500 μL) of nanoparticles were transferred into a 1.5 mL LB-eppendorf vial (see table 2)

Buffer exchange: The samples were centrifuged (15 min (NP20); 60 min (NP10), 25 000 rcf) until the supernatant is colorless, the supernatant (10 mM PBS, pH 7.4, 0.02% NaN3, 0.01% BSA) was removed and 500 μL of reaction buffer KP buffer (pH 7.4) was added, the samples were resuspended by vortex and centrifuged again, KP buffer was removed and finally 50 μL KP buffer was added (cNP=10 mg/mL)

Depending on the Biotin-binding capacity of streptavidin nanoparticle (hereinafter "BiKA for NP10 and NP20, an 40-fold excess of the respective L-LNA was added (100 nmol/mL in KP-buffer pH 7.4) to the nanoparticle suspension resulting in reaction concentrations of 0.9 and 1.7 mg/mL respectively The conjugation was conducted using a thermo shaker: 1 h, 21∞C, 1000 rpm Purification: To remove free L-LNA the samples were centrifuged (15 min (NP20); 60 min (NP10), 25000 rcf) until the supernatant is colorless, supernatant was removed and 500 μL of KP buffer (pH 7.4) was added. This washing procedure was repeated twice.

Finally, the nanoparticle pellet was resuspended in 50 μL of KP buffer pH 7.4 (c=10 mg/mL)

Experiments (B) and (C)

Pretreatment of spin filters for wetting the membrane: centrifugation using 2 times 500 μL of KP buffer pH 7.4

For Experiment (B) 0.1 mg (100 μL) of nanoparticles were transferred into the spin filter For Experiment (C) 0.3 mg (300 μL) of nanoparticles were transferred into the spin filter Buffer exchange: 500 μL of reaction buffer KP buffer pH 7.4 was added into the spin filter and centrifuged (3 min; 8000 rpm (NP10, NP20)), this procedure was repeated twice The NP-suspension in the filter was transferred into 1.5 mL LB-Eppendorf vials using 100-200 μL of KP buffer pH 7.4

Depending on the BiKA for NP10 and NP20, a 40-fold excess of the respective L-LNA was added (B: 100 nmol/mL; C: 250 nmol/mL in KP-buffer pH 7.4) to the nanoparticle suspension, resulting in reaction concentrations of 0.5 and 0.7 mg/mL, respectively, for experiment B; and 0.9 and 1.2 mg/mL for experiment C.

The conjugation was conducted using a thermo shaker: 1 h, 21° C., 1000 rpm

Purification: To remove free L-LNA the samples were washed 3-6 times with 500 μL of KP-buffer pH 7.4 using the spin filter system (5-10 min, 8000 rpm). After each centrifugation step the NP were resuspended within the filter by pipetting. The filtrates were collected to check L-LNA amounts/washing efficacy via UV/Vis spectroscopy (260 nm).

Finally, the nanoparticle pellet was resuspended in ~100 μL of KP buffer pH 7.4 (c=1 mg/mL)

Results

DLS

Samples of reaction series A were analyzed by DLS measurements (5 μL NP suspension in water)

| Sample | Z-Average (d. nm) | Distribution |
|---|---|---|
| 10 nm Iron Oxide LOT#19170SHP-COOH1 (Probe KP: Carboxy NP10 von Ocean Nanotech) | 27.9 | 12 nm-21 nm |
| 10 nm Iron Oxide LOT#19313SHS-Streptavidin (Probe KP: SA-NP10 von Ocean Nanotech) | 183 | 24 nm-38 nm |
| 1) SB41A:10NP-LNA1 | 95 | 18 nm-33 nm |
| 2) SB41A:20NP-LNA1 | 276 | — |
| 3) SB41A:10NP-LNA2 | 98 | 24 nm-43 nm |
| 4) SB41A:20NP-LNA2 | 147 | 24 nm-44 nm |
| 5) SB41A:10NP-LNA3 | 120 | 15 nm-24 nm |
| 6) SB41A:20NP-LNA3 | 168 | — |
| 7) SB41A:10NP-LNA4 | 98 | 24 nm-44 nm |
| 8) SB41A:20NP-LNA4 | 243 | — |

DLS-measurements of samples 1, 3, 5, 7 (NP10) showed a size distribution of about 20 to about 40 nm for the LNA-coated particles. These diameters were similar to the precursor particles (10 nm Carboxyl particle and streptavidin particle).

No detectable increases in size by conjugation L-LNA (2700 g/mol) were observed

DLS-measurements of samples 2, 4, 6, 8 (NP20) were mostly not measurable. This was likely attributed to the agglomeration issue of NP20 conjugates.

Both streptavidin-coated particles (NP10 and NP20) showed different material characteristics.

The application of centrifugation processes (with and without spinfilters) lead to an agglomeration of NP20 particles. It is believed that the NP20 particles stuck on the filter membrane. Both facts lead to reduced yields of NP20 samples in the conjugation reaction with L-LNA. This could be observed by comparing the brownish color intensity of NP10 vs. NP20 samples.

BiKA Assay Using Biotin Fluorescein

NP10: BiKA 3030-3060 μmol/mg (~3.0 nmol/mg)

NP20: BiKA 10.400-11.500 μmol/mg (~10.4-11.5 nmol/mg)

Unexpectedly, the NP20 particle showed an about 3 to about 4 times higher BiKa than the NP10 particle.

The empirically determined BiKa of NP10 and NP20 in the experiments was determined to be:

NP 10: 2.5 nmol/mg Bead

NP 20: 1.25 nmol/mg Bead

For NP10 there is nearly a total match (2.5 nmol/mg vs. 3.0 nmol/mg).

For NP20 the experimentally determined Bika is about 10 times higher (1.25 nmol/mg vs. 11 nmol/mg).

Nevertheless, the 40-fold excess of L-LNA used in all experiments must be sufficient to generate 100% loading and this could be confirmed by the biotin-fluorescein assay (90-100% L-LNA loading).

ADDITIONAL EMBODIMENTS

A method of sequencing a plurality of target polynucleotides arrayed on a solid support including: incorporating of one of four different nucleotides into nucleic acid copy strands complementary to each of the plurality of target polynucleotides, wherein each of the four different nucleotides comprise (i) a 3'-hydroxyl protecting group, and (ii) a reactive group coupled to a nucleobase through a cleavable linker, and where each different nucleotide of the four different nucleotides includes a different nucleobase and a different reactive group; sequentially forming different subsets of nucleotide-conjugate complexes of the nascent nucleic acid strand, where each nucleotide-conjugate complex within each different subset of formed nucleotide-conjugate complexes is derived from only one of the different nucleotides incorporated into the nascent nucleic acid copy strands, wherein the sequential formation of each different subset of nucleotide-conjugate complexes includes: introducing a conjugate including a detectable label and which is orthogonally reactive with only one of the four different nucleotides incorporated into the complementary nucleic acid strands; detecting the formation of each nucleotide-conjugate complex within the subset by detecting the label of each introduced conjugate; determining a position within the solid support of each detected nucleotide-conjugate complex within the subset; and optionally cleaving at least a detectable label from each of the formed detectable nucleotide-conjugate complexes within the subset.

All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary, to employ concepts of the various patents, applications and publications to provide yet further embodiments.

Although the present disclosure has been described with reference to a number of illustrative embodiments, it should be understood that numerous other modifications and embodiments can be devised by those skilled in the art that will fall within the spirit and scope of the principles of this disclosure. More particularly, reasonable variations and modifications are possible in the component parts and/or arrangements of the subject combination arrangement within the scope of the foregoing disclosure, the drawings, and the appended claims without departing from the spirit of the disclosure. In addition to variations and modifications in the component parts and/or arrangements, alternative uses will also be apparent to those skilled in the art.

The invention claimed is:

1. A kit comprising:

(i) compounds or salts thereof having the structure of Formula (IB):

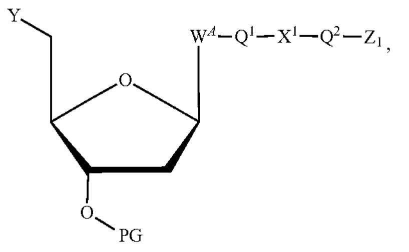

wherein

Y is —O—P(O)(OH)[—O—P(O)(OH)—]$_z$—OH or —O—P(O)(OH)-oligonucleotide, where z ranges from 2-about 5;

PG is a protecting group;

W is a nucleobase;

$Q^1$ is a straight chain or branched, substituted or unsubstituted, saturated or unsaturated aliphatic moiety having between 1 and about 25 carbon atoms and comprising one or more heteroatoms;

$Q^2$ is a straight chain or branched, substituted or unsubstituted, saturated or unsaturated, aliphatic or aromatic moiety having between 1 and 45 carbon atoms and comprising one or more heteroatoms;

$X^1$ is a cleavable group;

$Z^1$ is an oligonucleotide; and (ii) a conjugate having the structure of any of Formulas (IIA) or (IIB):

(IIA)

$$D—L^2—Z^2, \quad \text{or}$$

(IIB)

$$D\left[L^2—Z^2\right]_p,$$

D is a detectable label or a conjugate including a detectable label;

$L^2$ is a straight chain or branched, substituted or unsubstituted, saturated or unsaturated, aliphatic or aromatic moiety having between 1 and about 60 carbon atoms and comprising one or more heteroatoms;

$Z^2$ is an oligonucleotide which is complementary to the oligonucleotide of $Z^1$; and p is an integer ranging from 2 to about 1000.

2. The kit of claim 1, wherein $Z^1$ comprises an LNA- or PNA-modified oligonucleotide.

3. The kit of claim 1, wherein $Z^1$ comprises L-configured monomers.

4. The kit of claim 1, wherein the $Z^1$ oligonucleotide comprises a sequence having SEQ ID NO. 1.

5. The kit of claim 1, wherein the at least one cleavable group is selected from the group consisting of a chemically cleavable group, an enzymatically cleavable group, and a photocleavable group.

6. The kit of claim 1, wherein $Q^1$ comprises a $C_1$-$C_{10}$ straight chain or branched, substituted or unsubstituted alkyl or heteroalkyl group.

7. The kit of claim 1, wherein $Q^2$ comprises a $C_1$-$C_{20}$ straight chain or branched, substituted or unsubstituted alkyl or heteroalkyl group.

8. The kit of claim 1, wherein $X^1$ is selected from the group consisting of a photocleavable group, an enzymatically cleavable group, a chemically cleavable, and a pH sensitive group.

9. A nucleotide-conjugate complex, wherein the nucleotide-conjugate complex is produced by a process comprising: reacting (i) a nucleotide having Formula (IB):

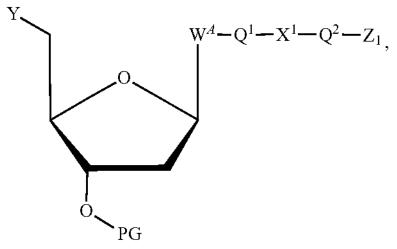

wherein

Y is —O—P(O)(OH)[—O—P(O)(OH)]z-OH or —O—P(O)(OH)-oligonucleotide;

where z ranges from 2 to about 5;

PG is a protecting group;

W is a nucleobase;

$Q^1$ is a straight chain or branched, substituted or unsubstituted, saturated or unsaturated aliphatic moiety having between 1 and about 25 carbon atoms and comprising one or more heteroatoms;

$Q^2$ is a straight chain or branched, substituted or unsubstituted, saturated or unsaturated, aliphatic or aromatic moiety having between 1 and 45 carbon atoms and comprising one or more heteroatoms;

$X^1$ is a cleavable group and $Z^1$ is an oligonucleotide;

with (ii) a conjugate having any one of Formulas (IIA) or (IIB):

(IIA)

$$D—L^2—Z^2, \quad \text{or}$$

-continued (IIB)

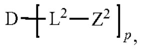

wherein

D is a detectable label or a conjugate including a detectable label;

$L^2$ is a straight chain or branched, substituted or unsubstituted, saturated or unsaturated, aliphatic or aromatic moiety having between 1 and about 60 carbon atoms and comprising one or more heteroatoms;

$Z^2$ is an oligonucleotide which is complementary to the oligonucleotide of $Z^1$; and p is an integer ranging from 2 to about 1000.

10. An assembly comprising a solid support of:

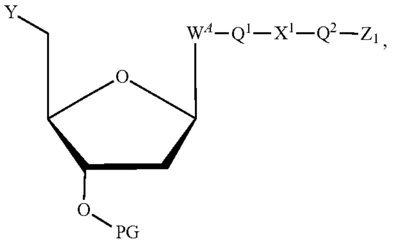

wherein

Y is —O—P(O)(OH)[—O—P(O)(OH)—]$_z$—OH or —O—P(O)(OH)-oligonucleotide, where z ranges from 2- about 5;

PG is a protecting group;

W is a nucleobase;

$Q^1$ is a straight chain or branched, substituted or unsubstituted, saturated or unsaturated aliphatic moiety having between 1 and about 25 carbon atoms and comprising one or more heteroatoms;

$Q^2$ is a straight chain or branched, substituted or unsubstituted, saturated or unsaturated, aliphatic or aromatic moiety having between 1 and 45 carbon atoms and comprising one or more heteroatoms;

$X^1$ is a cleavable group;

$Z^1$ is an oligonucleotide;

and a magnetic sensor array suitable for sequentially detecting different formed subsets of nucleotide-conjugate complexes comprising a magnetic nanoparticle and a conjugate having any one of Formulas (IIA) or (IIB):

(IIA)

$D—L^2—Z^2$, or (IIB)

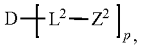

wherein

D is a detectable label or a conjugate including a detectable label;

$L^2$ is a straight chain or branched, substituted or unsubstituted, saturated or unsaturated, aliphatic or aromatic moiety having between 1 and about 60 carbon atoms and comprising one or more heteroatoms;

$Z^2$ is an oligonucleotide which is complementary to the oligonucleotide of $Z^1$; and p is an integer ranging from 2 to about 1000.

* * * * *

SEQUENCE LISTING

```
<160> NUMBER OF SEQ ID NOS: 58

<210> SEQ ID NO 1
<211> LENGTH: 5
<212> TYPE: DNA
<213> ORGANISM: Artificial Sequence
<220> FEATURE:
<223> OTHER INFORMATION: Synthetic

<400> SEQUENCE: 1

cttcc                                                                 5


<210> SEQ ID NO 2
<211> LENGTH: 5
<212> TYPE: DNA
<213> ORGANISM: Artificial Sequence
<220> FEATURE:
<223> OTHER INFORMATION: Synthetic

<400> SEQUENCE: 2

gctcc                                                                 5


<210> SEQ ID NO 3
<211> LENGTH: 6
<212> TYPE: DNA
<213> ORGANISM: Artificial Sequence
<220> FEATURE:
<223> OTHER INFORMATION: Synthetic

<400> SEQUENCE: 3

gttggt                                                                6


<210> SEQ ID NO 4
<211> LENGTH: 6
<212> TYPE: DNA
<213> ORGANISM: Artificial Sequence
<220> FEATURE:
<223> OTHER INFORMATION: Synthetic

<400> SEQUENCE: 4

ctgtca                                                                6


<210> SEQ ID NO 5
<211> LENGTH: 6
<212> TYPE: DNA
<213> ORGANISM: Artificial Sequence
```

<220> FEATURE:
<223> OTHER INFORMATION: Synthetic

<400> SEQUENCE: 5 tgctcc 6

<210> SEQ ID NO 6
<211> LENGTH: 6
<212> TYPE: DNA
<213> ORGANISM: Artificial Sequence
<220> FEATURE:
<223> OTHER INFORMATION: Synthetic

<400> SEQUENCE: 6 tcttcc 6

<210> SEQ ID NO 7
<211> LENGTH: 8
<212> TYPE: DNA
<213> ORGANISM: Artificial Sequence
<220> FEATURE:
<223> OTHER INFORMATION: Synthetic

<400> SEQUENCE: 7 gttggtgt 8

<210> SEQ ID NO 8
<211> LENGTH: 7
<212> TYPE: DNA
<213> ORGANISM: Artificial Sequence
<220> FEATURE:
<223> OTHER INFORMATION: Synthetic

<400> SEQUENCE: 8 gttggtg 7

<210> SEQ ID NO 9
<211> LENGTH: 8
<212> TYPE: DNA
<213> ORGANISM: Artificial Sequence
<220> FEATURE:
<223> OTHER INFORMATION: Synthetic

<400> SEQUENCE: 9 tgctcctg 8

<210> SEQ ID NO 10
<211> LENGTH: 8
<212> TYPE: DNA
<213> ORGANISM: Artificial Sequence
<220> FEATURE:
<223> OTHER INFORMATION: Synthetic

<400> SEQUENCE: 10 gtgcgtct 8

<210> SEQ ID NO 11
<211> LENGTH: 8
<212> TYPE: DNA
<213> ORGANISM: Artificial Sequence
<220> FEATURE:
<223> OTHER INFORMATION: Synthetic

<400> SEQUENCE: 11 gttggtgt 8

<210> SEQ ID NO 12
<211> LENGTH: 9
<212> TYPE: DNA
<213> ORGANISM: Artificial Sequence
<220> FEATURE:
<223> OTHER INFORMATION: Synthetic

<400> SEQUENCE: 12 tgctcctgt 9

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 gttggtgtg 9

<210> SEQ ID NO 14
<211> LENGTH: 9
<212> TYPE: DNA
<213> ORGANISM: Artificial Sequence
<220> FEATURE:
<223> OTHER INFORMATION: Synthetic

<400> SEQUENCE: 14 ttctcttcc 9

<210> SEQ ID NO 15
<211> LENGTH: 12
<212> TYPE: DNA
<213> ORGANISM: Artificial Sequence
<220> FEATURE:
<223> OTHER INFORMATION: Synthetic

<400> SEQUENCE: 15
gttggtgtgt tg 12

<210> SEQ ID NO 16
<211> LENGTH: 15
<212> TYPE: DNA
<213> ORGANISM: Artificial Sequence
<220> FEATURE:
<223> OTHER INFORMATION: Synthetic

<400> SEQUENCE: 16
gttggtgtgt tggtg 15

<210> SEQ ID NO 17
<211> LENGTH: 9
<212> TYPE: DNA
<213> ORGANISM: Artificial Sequence
<220> FEATURE:
<223> OTHER INFORMATION: Synthetic

<400> SEQUENCE: 17 aaaaaaaaa 9

<210> SEQ ID NO 18
<211> LENGTH: 6
<212> TYPE: DNA
<213> ORGANISM: Artificial Sequence
<220> FEATURE:
<223> OTHER INFORMATION: Synthetic

<400> SEQUENCE: 18 aaaaaa 6

<210> SEQ ID NO 19
<211> LENGTH: 6
<212> TYPE: DNA
<213> ORGANISM: Artificial Sequence
<220> FEATURE:
<223> OTHER INFORMATION: Synthetic

<400> SEQUENCE: 19 tatcgc 6

<210> SEQ ID NO 20
<211> LENGTH: 6
<212> TYPE: DNA
<213> ORGANISM: Artificial Sequence
<220> FEATURE:
<223> OTHER INFORMATION: Synthetic

<400> SEQUENCE: 20 tctgac 6

<210> SEQ ID NO 21
<211> LENGTH: 6
<212> TYPE: DNA
<213> ORGANISM: Artificial Sequence
<220> FEATURE:
<223> OTHER INFORMATION: Synthetic

<400> SEQUENCE: 21 agagag 6

<210> SEQ ID NO 22
<211> LENGTH: 6
<212> TYPE: DNA
<213> ORGANISM: Artificial Sequence
<220> FEATURE:
<223> OTHER INFORMATION: Synthetic

<400> SEQUENCE: 22 cacaca 6

<210> SEQ ID NO 23
<211> LENGTH: 20
<212> TYPE: DNA
<213> ORGANISM: Artificial Sequence
<220> FEATURE:
<223> OTHER INFORMATION: Synthetic

<400> SEQUENCE: 23
cagtggacga cgatagacat 20

<210> SEQ ID NO 24
<211> LENGTH: 20
<212> TYPE: DNA
<213> ORGANISM: Artificial Sequence
<220> FEATURE:
<223> OTHER INFORMATION: Synthetic

<400> SEQUENCE: 24
agaggatcga ggagtacagg 20

<210> SEQ ID NO 25

<211> LENGTH: 20
<212> TYPE: DNA
<213> ORGANISM: Artificial Sequence
<220> FEATURE:
<223> OTHER INFORMATION: Synthetic

<400> SEQUENCE: 25
agaaatggac gagatgctaa 20

<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26
actgaacttg tgagaaacgc 20

<210> SEQ ID NO 27
<211> LENGTH: 20
<212> TYPE: DNA
<213> ORGANISM: Artificial Sequence
<220> FEATURE:
<223> OTHER INFORMATION: Synthetic

<400> SEQUENCE: 27
atggagagtc aggcaagttt 20

<210> SEQ ID NO 28
<211> LENGTH: 20
<212> TYPE: DNA
<213> ORGANISM: Artificial Sequence
<220> FEATURE:
<223> OTHER INFORMATION: Synthetic

<400> SEQUENCE: 28
tgaagatgcg agtgatgaac 20

<210> SEQ ID NO 29
<211> LENGTH: 5
<212> TYPE: DNA
<213> ORGANISM: Artificial Sequence
<220> FEATURE:
<223> OTHER INFORMATION: Synthetic

<400> SEQUENCE: 29 ggaag 5

<210> SEQ ID NO 30
<211> LENGTH: 5
<212> TYPE: DNA
<213> ORGANISM: Artificial Sequence
<220> FEATURE:
<223> OTHER INFORMATION: Synthetic

<400> SEQUENCE: 30 ggagc 5

<210> SEQ ID NO 31
<211> LENGTH: 6
<212> TYPE: DNA
<213> ORGANISM: Artificial Sequence
<220> FEATURE:
<223> OTHER INFORMATION: Synthetic

<400> SEQUENCE: 31 accaac 6

<210> SEQ ID NO 32
<211> LENGTH: 6
<212> TYPE: DNA
<213> ORGANISM: Artificial Sequence
<220> FEATURE:
<223> OTHER INFORMATION: Synthetic

<400> SEQUENCE: 32 tgacag 6

<210> SEQ ID NO 33
<211> LENGTH: 6
<212> TYPE: DNA
<213> ORGANISM: Artificial Sequence
<220> FEATURE:
<223> OTHER INFORMATION: Synthetic

<400> SEQUENCE: 33 ggagca 6

<210> SEQ ID NO 34
<211> LENGTH: 6
<212> TYPE: DNA
<213> ORGANISM: Artificial Sequence
<220> FEATURE:
<223> OTHER INFORMATION: Synthetic

<400> SEQUENCE: 34 ggaaga 6

<210> SEQ ID NO 35
<211> LENGTH: 8
<212> TYPE: DNA
<213> ORGANISM: Artificial Sequence
<220> FEATURE:
<223> OTHER INFORMATION: Synthetic

<400> SEQUENCE: 35 acaccaac 8

<210> SEQ ID NO 36
<211> LENGTH: 7
<212> TYPE: DNA
<213> ORGANISM: Artificial Sequence
<220> FEATURE:
<223> OTHER INFORMATION: Synthetic

<400> SEQUENCE: 36 caccaac 7

<210> SEQ ID NO 37
<211> LENGTH: 8
<212> TYPE: DNA
<213> ORGANISM: Artificial Sequence
<220> FEATURE:
<223> OTHER INFORMATION: Synthetic

<400> SEQUENCE: 37 caggagca 8

<210> SEQ ID NO 38
<211> LENGTH: 8
<212> TYPE: DNA

<213> ORGANISM: Artificial Sequence
<220> FEATURE:
<223> OTHER INFORMATION: Synthetic

<400> SEQUENCE: 38 agacgcac 8

<210> SEQ ID NO 39
<211> LENGTH: 8
<212> TYPE: DNA
<213> ORGANISM: Artificial Sequence
<220> FEATURE:
<223> OTHER INFORMATION: Synthetic

<400> SEQUENCE: 39 acaccaac 8

<210> SEQ ID NO 40
<211> LENGTH: 9
<212> TYPE: DNA
<213> ORGANISM: Artificial Sequence
<220> FEATURE:
<223> OTHER INFORMATION: Synthetic

<400> SEQUENCE: 40 acaggagca 9

<210> SEQ ID NO 41
<211> LENGTH: 9
<212> TYPE: DNA
<213> ORGANISM: Artificial Sequence
<220> FEATURE:
<223> OTHER INFORMATION: Synthetic

<400> SEQUENCE: 41 cacaccaac 9

<210> SEQ ID NO 42
<211> LENGTH: 9
<212> TYPE: DNA
<213> ORGANISM: Artificial Sequence
<220> FEATURE:
<223> OTHER INFORMATION: Synthetic

<400> SEQUENCE: 42 ggaagagaa 9

<210> SEQ ID NO 43
<211> LENGTH: 12
<212> TYPE: DNA
<213> ORGANISM: Artificial Sequence
<220> FEATURE:
<223> OTHER INFORMATION: Synthetic

<400> SEQUENCE: 43
caacacacca ac 12

<210> SEQ ID NO 44
<211> LENGTH: 15
<212> TYPE: DNA
<213> ORGANISM: Artificial Sequence
<220> FEATURE:
<223> OTHER INFORMATION: Synthetic

<400> SEQUENCE: 44
caccaacaca ccaac 15

<210> SEQ ID NO 45
<211> LENGTH: 9
<212> TYPE: DNA
<213> ORGANISM: Artificial Sequence
<220> FEATURE:
<223> OTHER INFORMATION: Synthetic

<400> SEQUENCE: 45 ttttttttt 9

<210> SEQ ID NO 46
<211> LENGTH: 6
<212> TYPE: DNA
<213> ORGANISM: Artificial Sequence
<220> FEATURE:
<223> OTHER INFORMATION: Synthetic

<400> SEQUENCE: 46 tttttt 6

<210> SEQ ID NO 47
<211> LENGTH: 6
<212> TYPE: DNA
<213> ORGANISM: Artificial Sequence
<220> FEATURE:
<223> OTHER INFORMATION: Synthetic

<400> SEQUENCE: 47 gcgata 6

<210> SEQ ID NO 48
<211> LENGTH: 6
<212> TYPE: DNA
<213> ORGANISM: Artificial Sequence
<220> FEATURE:
<223> OTHER INFORMATION: Synthetic

<400> SEQUENCE: 48 gtcaga 6

<210> SEQ ID NO 49
<211> LENGTH: 6
<212> TYPE: DNA
<213> ORGANISM: Artificial Sequence
<220> FEATURE:
<223> OTHER INFORMATION: Synthetic

<400> SEQUENCE: 49 ctctct 6

<210> SEQ ID NO 50
<211> LENGTH: 6
<212> TYPE: DNA
<213> ORGANISM: Artificial Sequence
<220> FEATURE:
<223> OTHER INFORMATION: Synthetic

<400> SEQUENCE: 50 tgtgtg 6

<210> SEQ ID NO 51
<211> LENGTH: 20
<212> TYPE: DNA
<213> ORGANISM: Artificial Sequence
<220> FEATURE:

<223> OTHER INFORMATION: Synthetic

<400> SEQUENCE: 51
atgtctatcg tcgtccactg 20

<210> SEQ ID NO 52
<211> LENGTH: 20
<212> TYPE: DNA
<213> ORGANISM: Artificial Sequence
<220> FEATURE:
<223> OTHER INFORMATION: Synthetic

<400> SEQUENCE: 52
cctgtactcc tcgatcctct 20

<210> SEQ ID NO 53
<211> LENGTH: 20
<212> TYPE: DNA
<213> ORGANISM: Artificial Sequence
<220> FEATURE:
<223> OTHER INFORMATION: Synthetic

<400> SEQUENCE: 53
ttagcatctc gtccatttct 20

<210> SEQ ID NO 54
<211> LENGTH: 20
<212> TYPE: DNA
<213> ORGANISM: Artificial Sequence
<220> FEATURE:
<223> OTHER INFORMATION: Synthetic

<400> SEQUENCE: 54
gcgtttctca caagttcagt 20

<210> SEQ ID NO 55
<211> LENGTH: 20
<212> TYPE: DNA
<213> ORGANISM: Artificial Sequence
<220> FEATURE:
<223> OTHER INFORMATION: Synthetic

<400> SEQUENCE: 55
aaacttgcct gactctccat 20

<210> SEQ ID NO 56
<211> LENGTH: 20
<212> TYPE: DNA
<213> ORGANISM: Artificial Sequence
<220> FEATURE:
<223> OTHER INFORMATION: Synthetic

<400> SEQUENCE: 56
gttcatcact cgcatcttca 20

<210> SEQ ID NO 57
<211> LENGTH: 6
<212> TYPE: DNA
<213> ORGANISM: Artificial Sequence
<220> FEATURE:
<223> OTHER INFORMATION: Synthetic

<400> SEQUENCE: 57 tgagtg 6

-continued

```
<210> SEQ ID NO 58
<211> LENGTH: 6
<212> TYPE: DNA
<213> ORGANISM: Artificial Sequence
<220> FEATURE:
<223> OTHER INFORMATION: Synthetic

<400> SEQUENCE: 58

cactca                                                               6
```